United States Patent
Chung et al.

(10) Patent No.: US 11,939,609 B2
(45) Date of Patent: Mar. 26, 2024

(54) REWIRING ABERRANT CANCER SIGNALING TO A THERAPEUTIC EFFECTOR RESPONSE WITH A SYNTHETIC TWO-COMPONENT SYSTEM

(71) Applicant: The Board of Trustees of the Leland Stanford Junior University, Stanford, CA (US)

(72) Inventors: Hokyung Chung, Mountain View, CA (US); Michael Z. Lin, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1091 days.

(21) Appl. No.: 16/400,976

(22) Filed: May 1, 2019

(65) Prior Publication Data
US 2019/0256833 A1  Aug. 22, 2019

Related U.S. Application Data

(63) Continuation-in-part of application No. 16/044,131, filed on Jul. 24, 2018.

(60) Provisional application No. 62/536,165, filed on Jul. 24, 2017.

(51) Int. Cl.
| | | |
|---|---|---|
| *A61K 48/00* | (2006.01) | |
| *A61P 35/00* | (2006.01) | |
| *C07K 14/47* | (2006.01) | |
| *C07K 14/535* | (2006.01) | |
| *C12N 9/22* | (2006.01) | |
| *C12N 9/50* | (2006.01) | |
| *C12N 15/11* | (2006.01) | |
| *C12N 15/86* | (2006.01) | |
| *A61K 38/00* | (2006.01) | |
| *C12N 15/113* | (2010.01) | |

(52) U.S. Cl.
CPC .............. *C12N 9/506* (2013.01); *A61P 35/00* (2018.01); *C07K 14/4702* (2013.01); *C07K 14/4747* (2013.01); *C07K 14/535* (2013.01); *C12N 9/22* (2013.01); *C12N 15/11* (2013.01); *C12N 15/86* (2013.01); *C12Y 304/21098* (2013.01); *A61K 38/00* (2013.01); *C07K 2319/01* (2013.01); *C07K 2319/50* (2013.01); *C07K 2319/70* (2013.01); *C12N 15/1136* (2013.01); *C12N 2310/20* (2017.05); *C12N 2740/15033* (2013.01); *C12N 2740/15043* (2013.01); *C12N 2800/80* (2013.01)

(58) Field of Classification Search
None
See application file for complete search history.

(56) References Cited

U.S. PATENT DOCUMENTS

| | | |
|---|---|---|
| 5,728,868 A | 3/1998 | Springer et al. |
| 7,638,127 B2 | 12/2009 | Gengrinovitch et al. |
| 8,314,060 B2 | 11/2012 | Gengrinovitch et al. |
| 9,090,640 B2 | 7/2015 | Bierbach et al. |
| 9,102,759 B2 | 8/2015 | Pieczykolan et al. |

FOREIGN PATENT DOCUMENTS

| | | |
|---|---|---|
| WO | 2013/142965 A1 | 10/2013 |
| WO | 2016/149274 A1 | 9/2016 |

OTHER PUBLICATIONS

Fukazawa et al., J.B.C., 2003, 278: 25428-25434.*
Naso et al., BioDrugs, Jul. 1, 2017, 31: 317-334.*
Yang et al., Clin. Cancer Res., 2009, 15: 752-757.*
Barnea et al., (2008) "The genetic design of signaling cascades to record receptor activation", PNAS, 105(1)64-69.
Brown et al., (2004) "Exploiting tumour hypoxia in cancer treatment", Nature Review Cancer, 4:437-447.
Hong et al., (2012) "Inhibition of Akt/FOXO3a signaling by constitutively active FOXO3a suppresses growth of follicular thyroid cancer cell lines", Cancer Letter, 314:34-40.
Jiang et al., (2013) "Characterization of mammalian N-degrons and development of heterovalent inhibitors of the N-end rule pathway", Chemical Science, 3339-3346.
Margolis et al., (1992) "Tyrosine phosphorylation of vav proto-oncogene product containing SH2 domain and transcription factor motifs", Nature, 356:71-74.
Qi et al., (2011) "Tumor suppressor FOXO3 mediates signals from the EGF receptor to regulate proliferation of colonic cells", American Journal of Physiology-Gastrointestinal, 300:G264-G272.
Ruan et al., (2001) "A Hypoxia-Regulated Adeno-Associated Virus Vector for Cancer-Specific Gene Therapy", Neoplasia, 3(3): 255-263.
Srinivas et al., (1999) "Characterization of an oxygen/redox-dependent degradation domain of hypoxia-inducible factor alpha (HIF-alpha) proteins", Biochemical Biophysical Research Communications, 260:557-561.

(Continued)

*Primary Examiner* — Ileana Popa
(74) *Attorney, Agent, or Firm* — Jenny L. Buchbinder; Bozicevic, Field & Francis LLP

(57) ABSTRACT

Compositions and methods for targeted treatment of cancer are disclosed. In particular, the invention relates to methods of targeting anti-cancer therapy to cells exhibiting aberrant signaling associated with cancer pathogenesis by administering synthetic signaling proteins that couple detection of an oncogenic signal to release of therapeutic agents into cancerous cells.

36 Claims, 86 Drawing Sheets

Specification includes a Sequence Listing.

(56) References Cited

OTHER PUBLICATIONS

Tang et al., (2000) "Epidermal Growth Factor Receptor vIII Enhances Tumorigenicity in Human Breast Cancer", Cancer Research, 60:3081-3087.
Yaffe, Michael B., (2002) "Phosphotyrosine-Binding Domains in Signal Transduction", Nature Review, Molecular Cell Biology, 3:177-186.
Cleland et al., (2001) "Emerging protein delivery methods", Current Opinion in Biotechnology, 12:212-219.
Koval et al., (2012) "A novel pro-apoptotic effector lactaptin inhibits tumor growth in mice models", BioChimie, 94:2467-2474.
Levi et al., (2004) "EGF-Receptor Related Protein Causes Cell Cycle Arrest and Induces Apoptosis of Colon Cancer Cells In Vitro and In Vivo", Anticancer Research, 24:2885-2892.
Perrin, (2014) "Make mouse studies work", Nature, 507:423-425.
Rivas et al. (2001) BCR-ABL-expressing cells transduced with the HSV-tk gene die by apoptosis upon treatment with ganciclovir. Mol. Ther. 3(5 Pt 1): 642-652.
Denmeade et al. (1998) Enzymatic activation of a doxorubicin-peptide prodrug by prostate-specific antigen. Cancer Res. 58(12):2537-2540.
Aloysius et al. (2015) Targeted prodrug approaches for hormone refractory prostate cancer.Med Res Rev. 35 (3):554-585.
Brennen et al. (2014) Pharmacokinetics and toxicology of a fibroblast activation protein (FAP)-activated prodrug in murine xenograft models of human cancer. Prostate 74(13):1308-1319.
Tai et al. (2011) Development of a peptide-drug conjugate for prostate cancer therapy. Mol. Pharm. 8(3):901-912.
Sandersjoo et al. (2015) A new prodrug form of Affibody molecules (pro-Affibody) is selectively activated by cancer-associated proteases. Cell Mol. Life Sci. 72(7): 1405-1415.
Chung et al. (2015) Tunable and reversible drug control of protein production via a self-excising degron. Nat Chem Biol. 11(9):713-720.
Barnea et al., (2008) "Supporting Information", PNAS, 105:1-2.
Lee et al., (2013) "High-Throughput Screening (HTS) and Hit Validation to Identify Small Molecule Inhibitors with Activity against NS3/4A proteases from Multiple Hepatitis C Virus Genotypes", Plos One, 8(10):1-12, e75144.
"Sequence Alignment", Office Action dated Jun. 14, 2022 under U.S. Appl. No. 16/044,131, 2 pages.

* cited by examiner

FIG. 11B

| Model parameter | Value or source |
|---|---|
| ShcPTB-phosphoErbB dissociation constant | 47 nM (11) |
| ShcPTB-protease synthesis rate | fig. S2H |
| ShcPTB-protease degradation rate | fig. S2E, S5D |
| cargo-substrate-CAAX synthesis rate | fig. S2H, S4E |
| cargo-substrate-CAAX degradation rate | fig. S2E, S4D |
| cargo degradation rate | fig. S2E |
| substrate-CAAX degradation rate | fig. S2E |
| protease-substrate Michaelis constant | fig. S1E |
| protease catalytic turnover rate | fig. S1E |
| phosphoErbB molecules/cell | fig. S1F |
| juxtamembrane volume | fig. S1B, Fig. 1C |

FIG. 12D

| Substrate | Protease | $k_{cat}$ (s$^{-1}$) | $K_M$ (µM) | Ref. |
|---|---|---|---|---|
| EDVVCC | NS3(54A) | 0.018 | 135 | (16, 17) |
| DEMEEC | NS3(54A) | 0.005 | 403 | (16, 17) |
| EDVVCC | NS3 | 0.18 | 270 | (16) |
| DEMEEC | NS3 | 0.05 | 805 | (16) |

FIG. 12E

| Cell line | Origin | ErbB activation mechanism | pErbB1 # per cell | pErbB2 # per cell | mAb/TKI-sensitive | Ref. |
|---|---|---|---|---|---|---|
| MCF-7 | breast | none | NA | NA | no | (13) |
| BT-474 | breast | overexpression | 4330 | 2360 | yes | (12, 13) |
| SK-BR-3 | breast | overexpression | 7520 | 2760 | yes | (12, 13) |
| SK-OV-3 | ovary | overexpression | 38700 | 2860 | yes | (12, 13) |
| NCI-H1975 | lung | overexpression, point mutation | 130000 | ND | yes | (12, 14, 15) |
| LN-229:EGFRvIII | brain | overexpression, deletion mutation | ND | ND | yes | (20) |

FIG. 12F

| Component | $t_{1/2}$ (h) | $K_{deg}$ (h$^{-1}$) |
|---|---|---|
| ShcPTB-NS3protease (PTB-pro) | 5.6 | 0.117 |
| OFP | 26.5 | 0.026 |
| OFP-DEMEEC-CAAX | 7.6 | 0.096 |

FIG. 13E

| binding domain | $K_D$ with ErbB1/EGFR | pTyr binding site (aa) | $K_D$ with ErbB2/HER2 | pTyr binding site (aa) |
|---|---|---|---|---|
| PIK3R1 SH2 (NT) | 646 nM | 1016 | 508 nM | 1139 |
| PIK3R2 SH2 (NT) | 425 nM | 1016 | 281 nM | |
| PIK3R3 SH2 (CT) | 193 nM | 1016 | 304 nM | |
| SYK SH2 (CT) | 934 nM | 1016 | 240 nM | |
| VAV1 SH2 | 1 μM | 1016 | 206 nM | |
| PLCG1 SH2 (CT) | 2 μM | 1016 | 1.9 μM | |
| CRK SH2 | 407 nM | 1016 | 848 nM | 1196 |

FIG. 14A

SEQUENCE LISTING

<160> NUMBER OF SEQ ID NOS: 24

<210> SEQ ID NO 1
<211> LENGTH: 186
<212> TYPE: PRT
<213> ORGANISM: Hepatitis C virus

<400> SEQUENCE: 1

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Thr Gln Thr Phe Leu Ala Thr Cys Ile
        35                  40                  45

Asn Gly Val Cys Trp Ala Val Tyr His Gly Ala Gly Thr Arg Thr Ile
    50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp
            180                 185

<210> SEQ ID NO 2
<211> LENGTH: 10
<212> TYPE: PRT
<213> ORGANISM: Artificial Sequence
<220> FEATURE:
<223> OTHER INFORMATION: HCV NS4A/4B protease cleavage site

<400> SEQUENCE: 2

Asp Glu Met Glu Glu Cys Ser Gln His Leu
1               5                   10

<210> SEQ ID NO 3
<211> LENGTH: 9
<212> TYPE: PRT
<213> ORGANISM: Artificial Sequence
<220> FEATURE:
<223> OTHER INFORMATION: HCV NS5A/5B protease cleavage site

<400> SEQUENCE: 3

Glu Asp Val Val Pro Cys Ser Met Gly
1               5

<210> SEQ ID NO 4
<211> LENGTH: 185
<212> TYPE: PRT
<213> ORGANISM: Artificial Sequence
<220> FEATURE:
<223> OTHER INFORMATION: phosphotyrosine binding domain

<400> SEQUENCE: 4

```
Met Gly Lys Pro Leu His Pro Asn Asp Lys Val Met Gly Pro Gly Val
1               5                   10                  15

Ser Tyr Leu Val Arg Tyr Met Gly Cys Val Glu Val Leu Gln Ser Met
            20                  25                  30

Arg Ala Leu Asp Phe Asn Thr Arg Thr Gln Val Thr Arg Glu Ala Ile
        35                  40                  45

Ser Leu Val Cys Glu Ala Val Pro Gly Ala Lys Gly Ala Thr Arg Arg
    50                  55                  60

Arg Lys Pro Cys Ser Arg Pro Leu Ser Ser Ile Leu Gly Arg Ser Asn
65                  70                  75                  80

Leu Lys Phe Ala Gly Met Pro Ile Thr Leu Thr Val Ser Thr Ser Ser
                85                  90                  95

Leu Asn Leu Met Ala Ala Asp Cys Lys Gln Ile Ile Ala Asn His His
            100                 105                 110

Met Gln Ser Ile Ser Phe Ala Ser Gly Gly Asp Pro Asp Thr Ala Glu
        115                 120                 125

Tyr Val Ala Tyr Val Ala Lys Asp Pro Val Asn Gln Arg Ala Cys His
    130                 135                 140

Ile Leu Glu Cys Pro Glu Gly Leu Ala Gln Asp Val Ile Ser Thr Ile
145                 150                 155                 160

Gly Gln Ala Phe Glu Leu Arg Phe Lys Gln Tyr Leu Arg Asp Ile Glu
                165                 170                 175

Gln Val Pro Gln Gln Pro Thr Leu Lys
            180                 185
```

<210> SEQ ID NO 5
<211> LENGTH: 7
<212> TYPE: PRT
<213> ORGANISM: Artificial Sequence
<220> FEATURE:
<223> OTHER INFORMATION: HIF1a degron

<400> SEQUENCE: 5

```
Met Leu Ala Pro Tyr Ile Pro
1               5
```

<210> SEQ ID NO 6
<211> LENGTH: 186
<212> TYPE: PRT
<213> ORGANISM: Artificial Sequence
<220> FEATURE:
<223> OTHER INFORMATION: phosphotyrosine binding domain with HIF1a
      degron

<400> SEQUENCE: 6

```
Met Gly Lys Pro Leu His Pro Asn Asp Lys Val Met Gly Pro Gly Val
1               5                   10                  15

Ser Tyr Leu Val Arg Tyr Met Gly Cys Val Glu Val Leu Gln Ser Met
            20                  25                  30

Arg Ala Leu Asp Phe Asn Thr Arg Thr Gln Val Thr Arg Glu Ala Ile
        35                  40                  45

Ser Leu Val Cys Glu Ala Val Pro Gly Ala Lys Gly Ala Thr Arg Arg
    50                  55                  60

Arg Lys Pro Cys Ser Arg Pro Leu Ser Ser Ile Leu Gly Arg Ser Asn
65                  70                  75                  80

Leu Lys Phe Ala Gly Met Pro Ile Thr Leu Thr Val Ser Thr Ser Ser
```

```
                    85                  90                  95

Leu Asn Leu Met Ala Ala Asp Cys Lys Gln Ile Ile Ala Asn His His
                100                 105                 110

Met Gln Ser Ile Ser Phe Ala Ser Gly Met Leu Ala Pro Tyr Ile Pro
            115                 120                 125

Glu Tyr Val Ala Tyr Val Ala Lys Asp Pro Val Asn Gln Arg Ala Cys
        130                 135                 140

His Ile Leu Glu Cys Pro Glu Gly Leu Ala Gln Asp Val Ile Ser Thr
145                 150                 155                 160

Ile Gly Gln Ala Phe Glu Leu Arg Phe Lys Gln Tyr Leu Arg Asp Ile
                165                 170                 175

Glu Gln Val Pro Gln Gln Pro Thr Leu Lys
            180                 185

<210> SEQ ID NO 7
<211> LENGTH: 20
<212> TYPE: DNA
<213> ORGANISM: Artificial Sequence
<220> FEATURE:
<223> OTHER INFORMATION: gRNA 1
<220> FEATURE:
<221> NAME/KEY: source
<222> LOCATION: (1)..(20)
<223> OTHER INFORMATION: sequence is synthesized

<400> SEQUENCE: 7
gtgaccacaa aatgccaggg                                              20

<210> SEQ ID NO 8
<211> LENGTH: 20
<212> TYPE: DNA
<213> ORGANISM: Artificial Sequence
<220> FEATURE:
<223> OTHER INFORMATION: gRNA 2
<220> FEATURE:
<221> NAME/KEY: source
<222> LOCATION: (1)..(20)
<223> OTHER INFORMATION: sequence is synthesized

<400> SEQUENCE: 8
cgggggaact acctgaactg                                              20

<210> SEQ ID NO 9
<211> LENGTH: 20
<212> TYPE: DNA
<213> ORGANISM: Artificial Sequence
<220> FEATURE:
<223> OTHER INFORMATION: gRNA 3
<220> FEATURE:
<221> NAME/KEY: source
<222> LOCATION: (1)..(20)
<223> OTHER INFORMATION: sequence is synthesized

<400> SEQUENCE: 9
ggcccttatc agccacacat                                              20

<210> SEQ ID NO 10
<211> LENGTH: 20
<212> TYPE: DNA
<213> ORGANISM: Artificial Sequence
<220> FEATURE:
<223> OTHER INFORMATION: gRNA 4
<220> FEATURE:
<221> NAME/KEY: source
<222> LOCATION: (1)..(20)
<223> OTHER INFORMATION: sequence is synthesized
```

<400> SEQUENCE: 10
cggtgagcct tttccctagg                                                20

<210> SEQ ID NO 11
<211> LENGTH: 20
<212> TYPE: DNA
<213> ORGANISM: Artificial Sequence
<220> FEATURE:
<223> OTHER INFORMATION: gRNA 5
<220> FEATURE:
<221> NAME/KEY: source
<222> LOCATION: (1)..(20)
<223> OTHER INFORMATION: sequence is synthesized

<400> SEQUENCE: 11
ttatcagcca cacatgggaa                                                20

<210> SEQ ID NO 12
<211> LENGTH: 20
<212> TYPE: DNA
<213> ORGANISM: Artificial Sequence
<220> FEATURE:
<223> OTHER INFORMATION: gRNA 6
<220> FEATURE:
<221> NAME/KEY: source
<222> LOCATION: (1)..(20)
<223> OTHER INFORMATION: sequence is synthesized

<400> SEQUENCE: 12
gccaggagat tccacagttc                                                20

<210> SEQ ID NO 13
<211> LENGTH: 20
<212> TYPE: DNA
<213> ORGANISM: Artificial Sequence
<220> FEATURE:
<223> OTHER INFORMATION: gRNA 7
<220> FEATURE:
<221> NAME/KEY: source
<222> LOCATION: (1)..(20)
<223> OTHER INFORMATION: sequence is synthesized

<400> SEQUENCE: 13
tgggctgtcg gttcttggaa                                                20

<210> SEQ ID NO 14
<211> LENGTH: 20
<212> TYPE: DNA
<213> ORGANISM: Artificial Sequence
<220> FEATURE:
<223> OTHER INFORMATION: gRNA 8
<220> FEATURE:
<221> NAME/KEY: source
<222> LOCATION: (1)..(20)
<223> OTHER INFORMATION: sequence is synthesized

<400> SEQUENCE: 14
ccacccaccc gccttcctga                                                20

<210> SEQ ID NO 15
<211> LENGTH: 20
<212> TYPE: DNA
<213> ORGANISM: Artificial Sequence
<220> FEATURE:
<223> OTHER INFORMATION: gRNA 9
<220> FEATURE:
<221> NAME/KEY: source
<222> LOCATION: (1)..(20)

-continued

<223> OTHER INFORMATION: sequence is synthesized

<400> SEQUENCE: 15
tggagagccc tcaggaaggc                                         20

<210> SEQ ID NO 16
<211> LENGTH: 20
<212> TYPE: DNA
<213> ORGANISM: Artificial Sequence
<220> FEATURE:
<223> OTHER INFORMATION: gRNA 10
<220> FEATURE:
<221> NAME/KEY: source
<222> LOCATION: (1)..(20)
<223> OTHER INFORMATION: sequence is synthesized

<400> SEQUENCE: 16
ggctgccccc tccctctgag                                         20

<210> SEQ ID NO 17
<211> LENGTH: 400
<212> TYPE: PRT
<213> ORGANISM: Artificial Sequence
<220> FEATURE:
<223> OTHER INFORMATION: PTBHIF-NS3 protein sequence (protease component
      of ErbB-RASER system)

<400> SEQUENCE: 17

Met Gly Lys Pro Leu His Pro Asn Asp Lys Val Met Gly Pro Gly Val
1               5                   10                  15

Ser Tyr Leu Val Arg Tyr Met Gly Cys Val Glu Val Leu Gln Ser Met
            20                  25                  30

Arg Ala Leu Asp Phe Asn Thr Arg Thr Gln Val Thr Arg Glu Ala Ile
        35                  40                  45

Ser Leu Val Cys Glu Ala Val Pro Gly Ala Lys Gly Ala Thr Arg Arg
    50                  55                  60

Arg Lys Pro Cys Ser Arg Pro Leu Ser Ser Ile Leu Gly Arg Ser Asn
65                  70                  75                  80

Leu Lys Phe Ala Gly Met Pro Ile Thr Leu Thr Val Ser Thr Ser Ser
                85                  90                  95

Leu Asn Leu Met Ala Ala Asp Cys Lys Gln Ile Ile Ala Asn His His
            100                 105                 110

Met Gln Ser Ile Ser Phe Ala Ser Gly Met Leu Ala Pro Tyr Ile Pro
        115                 120                 125

Glu Tyr Val Ala Tyr Val Ala Lys Asp Pro Val Asn Gln Arg Ala Cys
    130                 135                 140

His Ile Leu Glu Cys Pro Glu Gly Leu Ala Gln Asp Val Ile Ser Thr
145                 150                 155                 160

Ile Gly Gln Ala Phe Glu Leu Arg Phe Lys Gln Tyr Leu Arg Asp Ile
                165                 170                 175

Glu Gln Val Pro Gln Pro Thr Leu Lys Met Asp Tyr Lys Asp Asp
            180                 185                 190

Asp Asp Lys Gly Ser Ser Gly Thr Gly Ser Gly Ser Gly Thr Ser Ala
        195                 200                 205

Pro Ile Thr Ala Tyr Ala Gln Gln Thr Arg Gly Leu Leu Gly Cys Ile
    210                 215                 220

Ile Thr Ser Leu Thr Gly Arg Asp Lys Asn Gln Val Glu Gly Glu Val
225                 230                 235                 240

Gln Ile Val Ser Thr Ala Thr Gln Thr Phe Leu Ala Thr Cys Ile Asn

```
                   245                 250                 255
Gly Val Cys Trp Thr Val Tyr His Gly Ala Gly Thr Arg Thr Ile Ala
            260                 265                 270

Ser Pro Lys Gly Pro Val Ile Gln Met Tyr Thr Asn Val Asp Gln Asp
        275                 280                 285

Leu Val Gly Trp Pro Ala Pro Gln Gly Ser Arg Ser Leu Thr Pro Cys
    290                 295                 300

Thr Cys Gly Ser Ser Asp Leu Tyr Leu Val Thr Arg His Ala Asp Val
305                 310                 315                 320

Ile Pro Val Arg Arg Arg Gly Asp Ser Arg Gly Ser Leu Leu Ser Pro
                325                 330                 335

Arg Pro Ile Ser Tyr Leu Lys Gly Ser Ser Gly Pro Leu Leu Cys
            340                 345                 350

Pro Ala Gly His Ala Val Gly Leu Phe Arg Ala Ala Val Cys Thr Arg
        355                 360                 365

Gly Val Ala Lys Ala Val Asp Phe Ile Pro Val Glu Asn Leu Glu Thr
    370                 375                 380

Thr Met Arg Ser Pro Val Phe Ser Asp Asn Ser Ser Pro Pro Ala Val
385                 390                 395                 400

<210> SEQ ID NO 18
<211> LENGTH: 755
<212> TYPE: PRT
<213> ORGANISM: Artificial Sequence
<220> FEATURE:
<223> OTHER INFORMATION: TM-SH2-substrate-BID-OFP protein

<400> SEQUENCE: 18

Met His Leu Arg Ile His Ala Arg Arg Ser Pro Pro Arg Arg Pro Ala
1               5                   10                  15

Trp Thr Leu Gly Ile Trp Phe Leu Phe Trp Gly Cys Ile Val Ser Ser
            20                  25                  30

Val Trp Ser Gln Leu Ser Ser Asn Val Ala Ser Ser Ser Thr Ser
        35                  40                  45

Ser Ser Pro Gly Ser His Tyr Pro Tyr Asp Val Pro Asp Tyr Ala Asn
    50                  55                  60

Pro Thr Glu Pro Gly Ile Arg Arg Val Pro Gly Ala Ser Glu Val Ile
65                  70                  75                  80

Arg Glu Ser Ser Ser Thr Thr Gly Met Val Val Gly Ile Val Ala Ala
                85                  90                  95

Ala Ala Leu Cys Ile Leu Ile Leu Leu Tyr Ala Met Tyr Lys Tyr Arg
            100                 105                 110

Asn Arg Asp Glu Gly Ser Gly Ser Thr Ser Gly Ser Gly Ser Gly Gly
        115                 120                 125

Ser Gly Gly Ser Gly Gly Ser Ser Gly Gly Met Asn Gly Ala Ile Gly
    130                 135                 140

Gly Asp Leu Leu Leu Asn Phe Pro Asp Met Ser Val Leu Glu Arg Gln
145                 150                 155                 160

Arg Ala His Leu Lys Tyr Leu Asn Pro Thr Phe Asp Ser Pro Leu Ala
                165                 170                 175

Gly Phe Phe Ala Asp Ser Ser Met Ile Thr Gly Gly Glu Met Asp Ser
            180                 185                 190

Tyr Leu Ser Thr Ala Gly Leu Asn Leu Pro Met Met Tyr Gly Glu Thr
        195                 200                 205

Thr Val Glu Gly Asp Ser Arg Leu Ser Ile Ser Pro Glu Thr Thr Leu
```

```
            210                 215                 220
Gly Thr Gly Asn Phe Lys Ala Ala Lys Phe Asp Thr Glu Thr Lys Asp
225                 230                 235                 240

Cys Asn Glu Ala Ala Lys Lys Met Thr Met Asn Arg Asp Asp Leu Val
                    245                 250                 255

Glu Glu Gly Glu Glu Lys Ser Lys Ile Thr Glu Gln Asn Asn Gly
                260                 265                 270

Ser Thr Lys Ser Ile Lys Lys Met Lys His Lys Ala Lys Lys Glu Glu
        275                 280                 285

Asn Asn Phe Ser Asn Asp Ser Ser Lys Val Thr Lys Glu Leu Glu Lys
        290                 295                 300

Thr Asp Tyr Ile His Ser Gly Ser Gly Gly Ser Gly Gly Ser Gly
305                 310                 315                 320

Gly Ser Gly Gly Ser Gly Gly Pro Pro Gln Asp Leu Ser Val His Leu
                325                 330                 335

Trp Tyr Ala Gly Pro Met Glu Arg Ala Gly Ala Glu Ser Ile Leu Ala
                340                 345                 350

Asn Arg Ser Asp Gly Thr Phe Leu Val Arg Gln Arg Val Lys Asp Ala
                355                 360                 365

Ala Glu Phe Ala Ile Ser Ile Lys Tyr Asn Val Glu Val Lys His Ile
        370                 375                 380

Lys Ile Met Thr Ala Glu Gly Leu Tyr Arg Ile Thr Glu Lys Lys Ala
385                 390                 395                 400

Phe Arg Gly Leu Thr Glu Leu Val Glu Phe Tyr Gln Gln Asn Ser Leu
                405                 410                 415

Lys Asp Cys Phe Lys Ser Leu Asp Thr Thr Leu Gln Phe Pro Phe Lys
                420                 425                 430

Glu Pro Glu Lys Arg Gly Ser Arg Gly Gly Ser Gly Ser Gly Gly
                435                 440                 445

Ser Gly Gly Ser Gly Gly Pro Ala Gly Ser Ser Gly Ser Ser Ile Ile
        450                 455                 460

Pro Asp Arg Glu Val Leu Tyr Gln Glu Phe Asp Glu Met Glu Glu Cys
465                 470                 475                 480

Ser Gln His Leu Pro Gly Ala Pro Met Glu Asp Ile Ile Arg Asn Ile
                485                 490                 495

Ala Arg His Leu Ala Val Gly Asp Asn Leu Asp Arg Ser Ile Trp Gly
                500                 505                 510

Gly Ser Gly Gly Ser Met Val Ser Val Ile Lys Pro Glu Met Lys Met
        515                 520                 525

Arg Tyr Tyr Met Asp Gly Ser Val Asn Gly His Glu Phe Thr Ile Glu
530                 535                 540

Gly Glu Gly Thr Gly Arg Pro Tyr Glu Gly His Gln Glu Met Thr Leu
545                 550                 555                 560

Arg Val Thr Met Ala Glu Gly Gly Pro Met Pro Phe Ala Phe Asp Leu
                565                 570                 575

Val Ser His Val Phe Cys Tyr Gly His Arg Val Phe Thr Lys Tyr Pro
                580                 585                 590

Glu Glu Ile Pro Asp Tyr Phe Lys Gln Ala Phe Pro Glu Gly Leu Ser
        595                 600                 605

Trp Glu Arg Ser Leu Glu Phe Glu Asp Gly Gly Ser Ala Ser Val Ser
        610                 615                 620

Ala His Ile Ser Leu Arg Gly Asn Thr Phe Tyr His Lys Ser Lys Phe
625                 630                 635                 640
```

```
Thr Gly Val Asn Phe Pro Ala Asp Gly Pro Ile Met Gln Asn Gln Ser
            645                 650                 655

Val Asp Trp Glu Pro Ser Thr Glu Lys Ile Thr Ala Ser Asp Gly Val
            660                 665                 670

Leu Lys Gly Asp Val Thr Met Tyr Leu Lys Leu Glu Gly Gly Gly Asn
            675                 680                 685

His Lys Cys Gln Met Lys Thr Thr Tyr Lys Ala Ala Lys Glu Ile Leu
            690                 695                 700

Glu Met Pro Gly Asp His Tyr Ile Gly His Arg Leu Val Arg Lys Thr
705                 710                 715                 720

Glu Gly Asn Ile Thr Glu Gln Val Glu Asp Ala Val Ala His Leu Lys
            725                 730                 735

Gly Ser Gly Lys Pro Ile Pro Asn Pro Leu Leu Gly Leu Asp Ser Thr
            740                 745                 750

Leu Ile Asn
            755

<210> SEQ ID NO 19
<211> LENGTH: 779
<212> TYPE: PRT
<213> ORGANISM: Artificial Sequence
<220> FEATURE:
<223> OTHER INFORMATION: TM-SH2-substrate-BID-mCardinal protein

<400> SEQUENCE: 19

Met His Leu Arg Ile His Ala Arg Arg Ser Pro Pro Arg Arg Pro Ala
1               5                   10                  15

Trp Thr Leu Gly Ile Trp Phe Leu Phe Trp Gly Cys Ile Val Ser Ser
            20                  25                  30

Val Trp Ser Gln Leu Ser Ser Asn Val Ala Ser Ser Ser Thr Ser
            35                  40                  45

Ser Ser Pro Gly Ser His Tyr Pro Tyr Asp Val Pro Asp Tyr Ala Asn
            50                  55                  60

Pro Thr Glu Pro Gly Ile Arg Arg Val Pro Gly Ala Ser Glu Val Ile
65                  70                  75                  80

Arg Glu Ser Ser Ser Thr Thr Gly Met Val Val Gly Ile Val Ala Ala
            85                  90                  95

Ala Ala Leu Cys Ile Leu Ile Leu Leu Tyr Ala Met Tyr Lys Tyr Arg
            100                 105                 110

Asn Arg Asp Glu Gly Ser Gly Ser Thr Ser Gly Ser Gly Ser Gly Gly
            115                 120                 125

Ser Gly Gly Ser Gly Gly Ser Ser Gly Gly Met Asn Gly Ala Ile Gly
            130                 135                 140

Gly Asp Leu Leu Leu Asn Phe Pro Asp Met Ser Val Leu Glu Arg Gln
145                 150                 155                 160

Arg Ala His Leu Lys Tyr Leu Asn Pro Thr Phe Asp Ser Pro Leu Ala
            165                 170                 175

Gly Phe Phe Ala Asp Ser Ser Met Ile Thr Gly Gly Glu Met Asp Ser
            180                 185                 190

Tyr Leu Ser Thr Ala Gly Leu Asn Leu Pro Met Met Tyr Gly Glu Thr
            195                 200                 205

Thr Val Glu Gly Asp Ser Arg Leu Ser Ile Ser Pro Glu Thr Thr Leu
            210                 215                 220

Gly Thr Gly Asn Phe Lys Ala Ala Lys Phe Asp Thr Glu Thr Lys Asp
225                 230                 235                 240
```

```
Cys Asn Glu Ala Ala Lys Lys Met Thr Met Asn Arg Asp Asp Leu Val
            245                 250                 255

Glu Glu Gly Glu Glu Lys Ser Lys Ile Thr Glu Gln Asn Asn Gly
            260                 265                 270

Ser Thr Lys Ser Ile Lys Lys Met Lys His Lys Ala Lys Lys Glu Glu
            275                 280                 285

Asn Asn Phe Ser Asn Asp Ser Ser Lys Val Thr Lys Glu Leu Glu Lys
            290                 295                 300

Thr Asp Tyr Ile His Ser Gly Ser Gly Gly Ser Gly Gly Ser Gly
305                 310                 315                 320

Gly Ser Gly Gly Ser Gly Gly Pro Pro Gln Asp Leu Ser Val His Leu
            325                 330                 335

Trp Tyr Ala Gly Pro Met Glu Arg Ala Gly Ala Glu Ser Ile Leu Ala
            340                 345                 350

Asn Arg Ser Asp Gly Thr Phe Leu Val Arg Gln Arg Val Lys Asp Ala
            355                 360                 365

Ala Glu Phe Ala Ile Ser Ile Lys Tyr Asn Val Glu Val Lys His Ile
            370                 375                 380

Lys Ile Met Thr Ala Glu Gly Leu Tyr Arg Ile Thr Glu Lys Lys Ala
385                 390                 395                 400

Phe Arg Gly Leu Thr Glu Leu Val Glu Phe Tyr Gln Gln Asn Ser Leu
            405                 410                 415

Lys Asp Cys Phe Lys Ser Leu Asp Thr Thr Leu Gln Phe Pro Phe Lys
            420                 425                 430

Glu Pro Glu Lys Arg Gly Ser Arg Gly Gly Ser Gly Ser Gly Gly
            435                 440                 445

Ser Gly Gly Ser Gly Gly Pro Ala Gly Ser Ser Gly Ser Ser Ile Ile
450                 455                 460

Pro Asp Arg Glu Val Leu Tyr Gln Glu Phe Asp Glu Met Glu Glu Cys
465                 470                 475                 480

Ser Gln His Leu Pro Gly Ala Pro Met Glu Asp Ile Ile Arg Asn Ile
            485                 490                 495

Ala Arg His Leu Ala Val Gly Asp Asn Leu Asp Arg Ser Ile Trp Gly
            500                 505                 510

Gly Ser Gly Gly Ser Val Ser Lys Gly Glu Glu Leu Ile Lys Glu Asn
            515                 520                 525

Met His Met Lys Leu Tyr Met Glu Gly Thr Val Asn Asn His His Phe
            530                 535                 540

Lys Cys Thr Thr Glu Gly Glu Gly Lys Pro Tyr Glu Gly Thr Gln Thr
545                 550                 555                 560

Gln Arg Ile Lys Val Val Glu Gly Gly Pro Leu Pro Phe Ala Phe Asp
            565                 570                 575

Ile Leu Ala Thr Cys Phe Met Tyr Gly Ser Lys Thr Phe Ile Asn His
            580                 585                 590

Thr Gln Gly Ile Pro Asp Phe Phe Lys Gln Ser Phe Pro Glu Gly Phe
            595                 600                 605

Thr Trp Glu Arg Val Thr Thr Tyr Glu Asp Gly Gly Val Leu Thr Val
            610                 615                 620

Thr Gln Asp Thr Ser Leu Gln Asp Gly Cys Leu Ile Tyr Asn Val Lys
625                 630                 635                 640

Leu Arg Gly Val Asn Phe Pro Ser Asn Gly Pro Val Met Gln Lys Lys
            645                 650                 655
```

```
Thr Leu Gly Trp Glu Ala Thr Thr Glu Thr Leu Tyr Pro Ala Asp Gly
            660                 665                 670

Gly Leu Glu Gly Arg Cys Asp Met Ala Leu Lys Leu Val Gly Gly Gly
        675                 680                 685

His Leu His Cys Asn Leu Lys Thr Thr Tyr Arg Ser Lys Lys Pro Ala
    690                 695                 700

Lys Asn Leu Lys Met Pro Gly Val Tyr Phe Val Asp Arg Arg Leu Glu
705                 710                 715                 720

Arg Ile Lys Glu Ala Asp Asn Glu Thr Tyr Val Glu Gln His Glu Val
                725                 730                 735

Ala Val Ala Arg Tyr Cys Asp Leu Pro Ser Lys Leu Gly His Lys Leu
            740                 745                 750

Asn Gly Met Asp Glu Leu Tyr Lys Gly Ser Gly Lys Pro Ile Pro Asn
        755                 760                 765

Pro Leu Leu Gly Leu Asp Ser Thr Leu Ile Asn
    770                 775
```

```
<210> SEQ ID NO 20
<211> LENGTH: 1961
<212> TYPE: PRT
<213> ORGANISM: Artificial Sequence
<220> FEATURE:
<223> OTHER INFORMATION: TM-SH2-substrate-Cas9VP64 protein

<400> SEQUENCE: 20

Met His Leu Arg Ile His Ala Arg Arg Ser Pro Pro Arg Arg Pro Ala
1               5                   10                  15

Trp Thr Leu Gly Ile Trp Phe Leu Phe Trp Gly Cys Ile Val Ser Ser
            20                  25                  30

Val Trp Ser Gln Leu Ser Ser Asn Val Ala Ser Ser Ser Ser Thr Ser
        35                  40                  45

Ser Ser Pro Gly Ser His Tyr Pro Tyr Asp Val Pro Asp Tyr Ala Asn
    50                  55                  60

Pro Thr Glu Pro Gly Ile Arg Arg Val Pro Gly Ala Ser Glu Val Ile
65                  70                  75                  80

Arg Glu Ser Ser Ser Thr Thr Gly Met Val Val Gly Ile Val Ala Ala
                85                  90                  95

Ala Ala Leu Cys Ile Leu Ile Leu Leu Tyr Ala Met Tyr Lys Tyr Arg
            100                 105                 110

Asn Arg Asp Glu Gly Ser Gly Ser Thr Ser Gly Ser Gly Ser Gly Gly
        115                 120                 125

Ser Gly Gly Ser Gly Gly Ser Ser Gly Gly Met Asn Gly Ala Ile Gly
    130                 135                 140

Gly Asp Leu Leu Leu Asn Phe Pro Asp Met Ser Val Leu Glu Arg Gln
145                 150                 155                 160

Arg Ala His Leu Lys Tyr Leu Asn Pro Thr Phe Asp Ser Pro Leu Ala
                165                 170                 175

Gly Phe Phe Ala Asp Ser Ser Met Ile Thr Gly Gly Glu Met Asp Ser
            180                 185                 190

Tyr Leu Ser Thr Ala Gly Leu Asn Leu Pro Met Met Tyr Gly Glu Thr
        195                 200                 205

Thr Val Glu Gly Asp Ser Arg Leu Ser Ile Ser Pro Glu Thr Thr Leu
    210                 215                 220

Gly Thr Gly Asn Phe Lys Ala Ala Lys Phe Asp Thr Glu Thr Lys Asp
225                 230                 235                 240
```

-continued

Cys Asn Glu Ala Ala Lys Lys Met Thr Met Asn Arg Asp Asp Leu Val
            245                 250                 255

Glu Glu Gly Glu Glu Glu Lys Ser Lys Ile Thr Glu Gln Asn Asn Gly
            260                 265                 270

Ser Thr Lys Ser Ile Lys Lys Met Lys His Lys Ala Lys Lys Glu Glu
            275                 280                 285

Asn Asn Phe Ser Asn Asp Ser Ser Lys Val Thr Lys Glu Leu Glu Lys
            290                 295                 300

Thr Asp Tyr Ile His Ser Gly Ser Gly Gly Ser Gly Gly Ser Gly
305                 310                 315                 320

Gly Ser Gly Gly Ser Gly Gly Pro Pro Gln Asp Leu Ser Val His Leu
            325                 330                 335

Trp Tyr Ala Gly Pro Met Glu Arg Ala Gly Ala Glu Ser Ile Leu Ala
            340                 345                 350

Asn Arg Ser Asp Gly Thr Phe Leu Val Arg Gln Arg Val Lys Asp Ala
            355                 360                 365

Ala Glu Phe Ala Ile Ser Ile Lys Tyr Asn Val Glu Val Lys His Ile
            370                 375                 380

Lys Ile Met Thr Ala Glu Gly Leu Tyr Arg Ile Thr Glu Lys Lys Ala
385                 390                 395                 400

Phe Arg Gly Leu Thr Glu Leu Val Glu Phe Tyr Gln Gln Asn Ser Leu
            405                 410                 415

Lys Asp Cys Phe Lys Ser Leu Asp Thr Thr Leu Gln Phe Pro Phe Lys
            420                 425                 430

Glu Pro Glu Lys Arg Gly Ser Arg Gly Gly Ser Gly Gly Ser Gly Gly
            435                 440                 445

Ser Gly Gly Ser Gly Gly Pro Ala Gly Ser Ser Gly Ser Ser Ile Ile
450                 455                 460

Pro Asp Arg Glu Val Leu Tyr Gln Glu Phe Asp Glu Met Glu Glu Cys
465                 470                 475                 480

Ser Gln His Leu Pro Gly Ala Pro Lys Arg Pro Ala Ala Thr Lys Lys
            485                 490                 495

Ala Gly Gln Ala Lys Lys Lys Asp Lys Lys Tyr Ser Ile Gly Leu
            500                 505                 510

Ala Ile Gly Thr Asn Ser Val Gly Trp Ala Val Ile Thr Asp Glu Tyr
            515                 520                 525

Lys Val Pro Ser Lys Lys Phe Lys Val Leu Gly Asn Thr Asp Arg His
            530                 535                 540

Ser Ile Lys Lys Asn Leu Ile Gly Ala Leu Leu Phe Asp Ser Gly Glu
545                 550                 555                 560

Thr Ala Glu Ala Thr Arg Leu Lys Arg Thr Ala Arg Arg Arg Tyr Thr
            565                 570                 575

Arg Arg Lys Asn Arg Ile Cys Tyr Leu Gln Glu Ile Phe Ser Asn Glu
            580                 585                 590

Met Ala Lys Val Asp Asp Ser Phe Phe His Arg Leu Glu Glu Ser Phe
            595                 600                 605

Leu Val Glu Glu Asp Lys Lys His Glu Arg His Pro Ile Phe Gly Asn
            610                 615                 620

Ile Val Asp Glu Val Ala Tyr His Glu Lys Tyr Pro Thr Ile Tyr His
625                 630                 635                 640

Leu Arg Lys Lys Leu Val Asp Ser Thr Asp Lys Ala Asp Leu Arg Leu
            645                 650                 655

Ile Tyr Leu Ala Leu Ala His Met Ile Lys Phe Arg Gly His Phe Leu

```
                660             665             670
Ile Glu Gly Asp Leu Asn Pro Asp Asn Ser Asp Val Asp Lys Leu Phe
            675             680             685

Ile Gln Leu Val Gln Thr Tyr Asn Gln Leu Phe Glu Glu Asn Pro Ile
            690             695             700

Asn Ala Ser Gly Val Asp Ala Lys Ala Ile Leu Ser Ala Arg Leu Ser
705             710             715             720

Lys Ser Arg Arg Leu Glu Asn Leu Ile Ala Gln Leu Pro Gly Glu Lys
                725             730             735

Lys Asn Gly Leu Phe Gly Asn Leu Ile Ala Leu Ser Leu Gly Leu Thr
            740             745             750

Pro Asn Phe Lys Ser Asn Phe Asp Leu Ala Glu Asp Ala Lys Leu Gln
            755             760             765

Leu Ser Lys Asp Thr Tyr Asp Asp Asp Leu Asp Asn Leu Leu Ala Gln
            770             775             780

Ile Gly Asp Gln Tyr Ala Asp Leu Phe Leu Ala Ala Lys Asn Leu Ser
785             790             795             800

Asp Ala Ile Leu Leu Ser Asp Ile Leu Arg Val Asn Thr Glu Ile Thr
                805             810             815

Lys Ala Pro Leu Ser Ala Ser Met Ile Lys Arg Tyr Asp Glu His His
                820             825             830

Gln Asp Leu Thr Leu Leu Lys Ala Leu Val Arg Gln Gln Leu Pro Glu
            835             840             845

Lys Tyr Lys Glu Ile Phe Phe Asp Gln Ser Lys Asn Gly Tyr Ala Gly
            850             855             860

Tyr Ile Asp Gly Gly Ala Ser Gln Glu Glu Phe Tyr Lys Phe Ile Lys
865             870             875             880

Pro Ile Leu Glu Lys Met Asp Gly Thr Glu Glu Leu Leu Val Lys Leu
                885             890             895

Asn Arg Glu Asp Leu Leu Arg Lys Gln Arg Thr Phe Asp Asn Gly Ser
                900             905             910

Ile Pro His Gln Ile His Leu Gly Glu Leu His Ala Ile Leu Arg Arg
            915             920             925

Gln Glu Asp Phe Tyr Pro Phe Leu Lys Asp Asn Arg Glu Lys Ile Glu
            930             935             940

Lys Ile Leu Thr Phe Arg Ile Pro Tyr Tyr Val Gly Pro Leu Ala Arg
945             950             955             960

Gly Asn Ser Arg Phe Ala Trp Met Thr Arg Lys Ser Glu Glu Thr Ile
                965             970             975

Thr Pro Trp Asn Phe Glu Glu Val Val Asp Lys Gly Ala Ser Ala Gln
            980             985             990

Ser Phe Ile Glu Arg Met Thr Asn Phe Asp Lys Asn Leu Pro Asn Glu
            995             1000            1005

Lys Val Leu Pro Lys His Ser Leu Leu Tyr Glu Tyr Phe Thr Val
        1010            1015            1020

Tyr Asn Glu Leu Thr Lys Val Lys Tyr Val Thr Glu Gly Met Arg
        1025            1030            1035

Lys Pro Ala Phe Leu Ser Gly Glu Gln Lys Lys Ala Ile Val Asp
        1040            1045            1050

Leu Leu Phe Lys Thr Asn Arg Lys Val Thr Val Lys Gln Leu Lys
        1055            1060            1065

Glu Asp Tyr Phe Lys Lys Ile Glu Cys Phe Asp Ser Val Glu Ile
        1070            1075            1080
```

-continued

Ser Gly Val Glu Asp Arg Phe Asn Ala Ser Leu Gly Thr Tyr His
1085                1090                1095

Asp Leu Leu Lys Ile Ile Lys Asp Lys Asp Phe Leu Asp Asn Glu
1100                1105                1110

Glu Asn Glu Asp Ile Leu Glu Asp Ile Val Leu Thr Leu Thr Leu
1115                1120                1125

Phe Glu Asp Arg Glu Met Ile Glu Glu Arg Leu Lys Thr Tyr Ala
1130                1135                1140

His Leu Phe Asp Asp Lys Val Met Lys Gln Leu Lys Arg Arg Arg
1145                1150                1155

Tyr Thr Gly Trp Gly Arg Leu Ser Arg Lys Leu Ile Asn Gly Ile
1160                1165                1170

Arg Asp Lys Gln Ser Gly Lys Thr Ile Leu Asp Phe Leu Lys Ser
1175                1180                1185

Asp Gly Phe Ala Asn Arg Asn Phe Met Gln Leu Ile His Asp Asp
1190                1195                1200

Ser Leu Thr Phe Lys Glu Asp Ile Gln Lys Ala Gln Val Ser Gly
1205                1210                1215

Gln Gly Asp Ser Leu His Glu His Ile Ala Asn Leu Ala Gly Ser
1220                1225                1230

Pro Ala Ile Lys Lys Gly Ile Leu Gln Thr Val Lys Val Val Asp
1235                1240                1245

Glu Leu Val Lys Val Met Gly Arg His Lys Pro Glu Asn Ile Val
1250                1255                1260

Ile Glu Met Ala Arg Glu Asn Gln Thr Thr Gln Lys Gly Gln Lys
1265                1270                1275

Asn Ser Arg Glu Arg Met Lys Arg Ile Glu Glu Gly Ile Lys Glu
1280                1285                1290

Leu Gly Ser Gln Ile Leu Lys Glu His Pro Val Glu Asn Thr Gln
1295                1300                1305

Leu Gln Asn Glu Lys Leu Tyr Leu Tyr Tyr Leu Gln Asn Gly Arg
1310                1315                1320

Asp Met Tyr Val Asp Gln Glu Leu Asp Ile Asn Arg Leu Ser Asp
1325                1330                1335

Tyr Asp Val Asp His Ile Val Pro Gln Ser Phe Leu Lys Asp Asp
1340                1345                1350

Ser Ile Asp Asn Lys Val Leu Thr Arg Ser Asp Lys Ala Arg Gly
1355                1360                1365

Lys Ser Asp Asn Val Pro Ser Glu Glu Val Val Lys Lys Met Lys
1370                1375                1380

Asn Tyr Trp Arg Gln Leu Leu Asn Ala Lys Leu Ile Thr Gln Arg
1385                1390                1395

Lys Phe Asp Asn Leu Thr Lys Ala Glu Arg Gly Gly Leu Ser Glu
1400                1405                1410

Leu Asp Lys Ala Gly Phe Ile Lys Arg Gln Leu Val Glu Thr Arg
1415                1420                1425

Gln Ile Thr Lys His Val Ala Gln Ile Leu Asp Ser Arg Met Asn
1430                1435                1440

Thr Lys Tyr Asp Glu Asn Asp Lys Leu Ile Arg Glu Val Lys Val
1445                1450                1455

Ile Thr Leu Lys Ser Lys Leu Val Ser Asp Phe Arg Lys Asp Phe
1460                1465                1470

-continued

```
Gln Phe Tyr Lys Val Arg Glu Ile Asn Asn Tyr His His Ala His
1475                1480                1485

Asp Ala Tyr Leu Asn Ala Val Val Gly Thr Ala Leu Ile Lys Lys
1490                1495                1500

Tyr Pro Lys Leu Glu Ser Glu Phe Val Tyr Gly Asp Tyr Lys Val
1505                1510                1515

Tyr Asp Val Arg Lys Met Ile Ala Lys Ser Glu Gln Glu Ile Gly
1520                1525                1530

Lys Ala Thr Ala Lys Tyr Phe Phe Tyr Ser Asn Ile Met Asn Phe
1535                1540                1545

Phe Lys Thr Glu Ile Thr Leu Ala Asn Gly Glu Ile Arg Lys Arg
1550                1555                1560

Pro Leu Ile Glu Thr Asn Gly Glu Thr Gly Glu Ile Val Trp Asp
1565                1570                1575

Lys Gly Arg Asp Phe Ala Thr Val Arg Lys Val Leu Ser Met Pro
1580                1585                1590

Gln Val Asn Ile Val Lys Lys Thr Glu Val Gln Thr Gly Gly Phe
1595                1600                1605

Ser Lys Glu Ser Ile Leu Pro Lys Arg Asn Ser Asp Lys Leu Ile
1610                1615                1620

Ala Arg Lys Lys Asp Trp Asp Pro Lys Lys Tyr Gly Gly Phe Asp
1625                1630                1635

Ser Pro Thr Val Ala Tyr Ser Val Leu Val Val Ala Lys Val Glu
1640                1645                1650

Lys Gly Lys Ser Lys Lys Leu Lys Ser Val Lys Glu Leu Leu Gly
1655                1660                1665

Ile Thr Ile Met Glu Arg Ser Ser Phe Glu Lys Asn Pro Ile Asp
1670                1675                1680

Phe Leu Glu Ala Lys Gly Tyr Lys Glu Val Lys Lys Asp Leu Ile
1685                1690                1695

Ile Lys Leu Pro Lys Tyr Ser Leu Phe Glu Leu Glu Asn Gly Arg
1700                1705                1710

Lys Arg Met Leu Ala Ser Ala Gly Glu Leu Gln Lys Gly Asn Glu
1715                1720                1725

Leu Ala Leu Pro Ser Lys Tyr Val Asn Phe Leu Tyr Leu Ala Ser
1730                1735                1740

His Tyr Glu Lys Leu Lys Gly Ser Pro Glu Asp Asn Glu Gln Lys
1745                1750                1755

Gln Leu Phe Val Glu Gln His Lys His Tyr Leu Asp Glu Ile Ile
1760                1765                1770

Glu Gln Ile Ser Glu Phe Ser Lys Arg Val Ile Leu Ala Asp Ala
1775                1780                1785

Asn Leu Asp Lys Val Leu Ser Ala Tyr Asn Lys His Arg Asp Lys
1790                1795                1800

Pro Ile Arg Glu Gln Ala Glu Asn Ile Ile His Leu Phe Thr Leu
1805                1810                1815

Thr Asn Leu Gly Ala Pro Ala Ala Phe Lys Tyr Phe Asp Thr Thr
1820                1825                1830

Ile Asp Arg Lys Arg Tyr Thr Ser Thr Lys Glu Val Leu Asp Ala
1835                1840                1845

Thr Leu Ile His Gln Ser Ile Thr Gly Leu Tyr Glu Thr Arg Ile
1850                1855                1860

Asp Leu Ser Gln Leu Gly Gly Asp Ser Ala Gly Gly Gly Gly Ser
```

```
                    1865                1870                1875

Gly Gly Gly Gly Ser Gly Gly Gly Ser Gly Pro Lys Lys Lys
            1880                1885            1890

Arg Lys Val Ala Ala Gly Ser Gly Arg Ala Asp Ala Leu Asp
    1895            1900                1905

Asp Phe Asp Leu Asp Met Leu Gly Ser Asp Ala Leu Asp Phe
        1910            1915            1920

Asp Leu Asp Met Leu Gly Ser Asp Ala Leu Asp Phe Asp Leu
    1925            1930            1935

Asp Met Leu Gly Ser Asp Ala Leu Asp Asp Phe Asp Leu Asp Met
1940            1945            1950

Leu Ile Asn Cys Thr Gly Ser Gly
        1955            1960

<210> SEQ ID NO 21
<211> LENGTH: 382
<212> TYPE: PRT
<213> ORGANISM: Artificial Sequence
<220> FEATURE:
<223> OTHER INFORMATION: BAX-substrate-SH2-CAAX

<400> SEQUENCE: 21

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
        50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

Gly Ser Gly Lys Pro Ile Pro Asn Pro Leu Leu Gly Leu Asp Ser Thr
        195                 200                 205

Asp Glu Met Glu Glu Cys Ser Gln His Leu Pro Gly Gly Ser Gly Gly
    210                 215                 220

Ser Gly Gly Ser Gly Gly Ser Gly Gly Pro Pro Gln Asp Leu Ser Val
225                 230                 235                 240

His Leu Trp Tyr Ala Gly Pro Met Glu Arg Ala Gly Ala Glu Ser Ile
                245                 250                 255

Leu Ala Asn Arg Ser Asp Gly Thr Phe Leu Val Arg Gln Arg Val Lys
```

```
                260               265                 270
Asp Ala Ala Glu Phe Ala Ile Ser Ile Lys Tyr Asn Val Glu Val Lys
            275                 280                 285
His Ile Lys Ile Met Thr Ala Glu Gly Leu Tyr Arg Ile Thr Glu Lys
            290                 295                 300
Lys Ala Phe Arg Gly Leu Thr Glu Leu Val Glu Phe Tyr Gln Gln Asn
305                 310                 315                 320
Ser Leu Lys Asp Cys Phe Lys Ser Leu Asp Thr Thr Leu Gln Phe Pro
                325                 330                 335
Phe Lys Glu Pro Glu Lys Arg Gly Ser Arg Gly Gly Ser Gly Gly Ser
                340                 345                 350
Gly Gly Ser Gly Gly Ser Gly Gly Gln Phe Lys Met Ser Lys Asp Gly
                355                 360                 365
Lys Lys Lys Lys Lys Lys Ser Lys Thr Lys Cys Val Ile Met
                370                 375                 380

<210> SEQ ID NO 22
<211> LENGTH: 879
<212> TYPE: PRT
<213> ORGANISM: Artificial Sequence
<220> FEATURE:
<223> OTHER INFORMATION: FOXO3-substrate-SH2-CAAX protein

<400> SEQUENCE: 22

Met Tyr Asp Val Pro Asp Tyr Ala Ser Leu Pro Gly Asn Met Ala Glu
1               5                   10                  15
Ala Pro Ala Ser Pro Ala Pro Leu Ser Pro Leu Glu Val Glu Leu Asp
                20                  25                  30
Pro Glu Phe Glu Pro Gln Ser Arg Pro Arg Ser Cys Ala Trp Pro Leu
            35                  40                  45
Gln Arg Pro Glu Leu Gln Ala Ser Pro Ala Lys Pro Ser Gly Glu Thr
        50                  55                  60
Ala Ala Asp Ser Met Ile Pro Glu Glu Glu Asp Asp Glu Asp Asp Glu
65              70                  75                  80
Asp Gly Gly Gly Arg Ala Gly Ser Ala Met Ala Ile Gly Gly Gly Gly
                85                  90                  95
Gly Ser Gly Thr Leu Gly Ser Gly Leu Leu Leu Glu Asp Ser Ala Arg
                100                 105                 110
Val Leu Ala Pro Gly Gly Gln Asp Pro Gly Ser Gly Pro Ala Thr Ala
            115                 120                 125
Ala Gly Gly Leu Ser Gly Gly Thr Gln Ala Leu Leu Gln Pro Gln Gln
        130                 135                 140
Pro Leu Pro Pro Pro Gln Pro Gly Ala Ala Gly Gly Ser Gly Gln Pro
145                 150                 155                 160
Arg Lys Cys Ser Ser Arg Arg Asn Ala Trp Gly Asn Leu Ser Tyr Ala
                165                 170                 175
Asp Leu Ile Thr Arg Ala Ile Glu Ser Ser Pro Asp Lys Arg Leu Thr
                180                 185                 190
Leu Ser Gln Ile Tyr Glu Trp Met Val Arg Cys Val Pro Tyr Phe Lys
            195                 200                 205
Asp Lys Gly Asp Ser Asn Ser Ser Ala Gly Trp Lys Asn Ser Ile Arg
        210                 215                 220
His Asn Leu Ser Leu His Ser Arg Phe Met Arg Val Gln Asn Glu Gly
225                 230                 235                 240
Thr Gly Lys Ser Ser Trp Trp Ile Ile Asn Pro Asp Gly Gly Lys Ser
```

```
                    245                 250                 255
Gly Lys Ala Pro Arg Arg Ala Val Ala Met Asp Asn Ser Asn Lys
                260                 265                 270

Tyr Thr Lys Ser Arg Gly Arg Ala Ala Lys Lys Ala Ala Leu Gln
            275                 280                 285

Thr Ala Pro Glu Ser Ala Asp Asp Ser Pro Ser Gln Leu Ser Lys Trp
        290                 295                 300

Pro Gly Ser Pro Thr Ser Arg Ser Ser Asp Glu Leu Asp Ala Trp Thr
305                 310                 315                 320

Asp Phe Arg Ser Arg Thr Asn Ala Asn Ala Ser Thr Val Ser Gly Arg
                325                 330                 335

Leu Ser Pro Ile Met Ala Ser Thr Glu Leu Asp Glu Val Gln Asp Asp
                340                 345                 350

Asp Ala Pro Leu Ser Pro Met Leu Tyr Ser Ser Ala Ser Leu Ser
                355                 360                 365

Pro Ser Val Ser Lys Pro Cys Thr Val Glu Leu Pro Arg Leu Thr Asp
            370                 375                 380

Met Ala Gly Thr Met Asn Leu Asn Asp Gly Leu Thr Glu Asn Leu Met
385                 390                 395                 400

Asp Asp Leu Leu Asp Asn Ile Thr Leu Pro Pro Ser Gln Pro Ser Pro
                405                 410                 415

Thr Gly Gly Leu Met Gln Arg Ser Ser Ser Phe Pro Tyr Thr Thr Lys
            420                 425                 430

Gly Ser Gly Leu Gly Ser Pro Thr Ser Ser Phe Asn Ser Thr Val Phe
            435                 440                 445

Gly Pro Ser Ser Leu Asn Ser Leu Arg Gln Ser Pro Met Gln Thr Ile
450                 455                 460

Gln Glu Asn Lys Pro Ala Thr Phe Ser Ser Met Ser His Tyr Gly Asn
465                 470                 475                 480

Gln Thr Leu Gln Asp Leu Leu Thr Ser Asp Ser Leu Ser His Ser Asp
            485                 490                 495

Val Met Met Thr Gln Ser Asp Pro Leu Met Ser Gln Ala Ser Thr Ala
                500                 505                 510

Val Ser Ala Gln Asn Ser Arg Arg Asn Val Met Leu Arg Asn Asp Pro
            515                 520                 525

Met Met Ser Phe Ala Ala Gln Pro Asn Gln Gly Ser Leu Val Asn Gln
            530                 535                 540

Asn Leu Leu His His Gln His Gln Thr Gln Gly Ala Leu Gly Gly Ser
545                 550                 555                 560

Arg Ala Leu Ser Asn Ser Val Ser Asn Met Gly Leu Ser Glu Ser Ser
                565                 570                 575

Ser Leu Gly Ser Ala Lys His Gln Gln Gln Ser Pro Val Ser Gln Ser
            580                 585                 590

Met Gln Thr Leu Ser Asp Ser Leu Ser Gly Ser Ser Leu Tyr Ser Thr
            595                 600                 605

Ser Ala Asn Leu Pro Val Met Gly His Glu Lys Phe Pro Ser Asp Leu
        610                 615                 620

Asp Leu Asp Met Phe Asn Gly Ser Leu Glu Cys Asp Met Glu Ser Ile
625                 630                 635                 640

Ile Arg Ser Glu Leu Met Asp Ala Asp Gly Leu Asp Phe Asn Phe Asp
                645                 650                 655

Ser Leu Ile Ser Thr Gln Asn Val Val Gly Leu Asn Val Gly Asn Phe
                660                 665                 670
```

```
Thr Gly Ala Lys Gln Ala Ser Ser Gln Ser Trp Val Pro Gly Gly Ala
        675                 680                 685

Pro Gly Ser Gly Lys Pro Ile Pro Asn Pro Leu Leu Gly Leu Asp Ser
        690                 695                 700

Thr Asp Glu Met Glu Glu Cys Ser Gln His Leu Pro Gly Gly Ser Gly
705                 710                 715                 720

Gly Ser Gly Gly Ser Gly Gly Ser Gly Gly Pro Pro Gln Asp Leu Ser
                725                 730                 735

Val His Leu Trp Tyr Ala Gly Pro Met Glu Arg Ala Gly Ala Glu Ser
                740                 745                 750

Ile Leu Ala Asn Arg Ser Asp Gly Thr Phe Leu Val Arg Gln Arg Val
                755                 760                 765

Lys Asp Ala Ala Glu Phe Ala Ile Ser Ile Lys Tyr Asn Val Glu Val
        770                 775                 780

Lys His Ile Lys Ile Met Thr Ala Glu Gly Leu Tyr Arg Ile Thr Glu
785                 790                 795                 800

Lys Lys Ala Phe Arg Gly Leu Thr Glu Leu Val Glu Phe Tyr Gln Gln
                805                 810                 815

Asn Ser Leu Lys Asp Cys Phe Lys Ser Leu Asp Thr Thr Leu Gln Phe
                820                 825                 830

Pro Phe Lys Glu Pro Glu Lys Arg Gly Ser Arg Gly Gly Ser Gly Gly
                835                 840                 845

Ser Gly Gly Ser Gly Gly Ser Gly Gly Gln Phe Lys Met Ser Lys Asp
        850                 855                 860

Gly Lys Lys Lys Lys Lys Lys Ser Lys Thr Lys Cys Val Ile Met
865                 870                 875

<210> SEQ ID NO 23
<211> LENGTH: 7524
<212> TYPE: DNA
<213> ORGANISM: Artificial Sequence
<220> FEATURE:
<223> OTHER INFORMATION: Lenti-ErbB-RASER1C-BID

<400> SEQUENCE: 23
gggtctctct ggttagacca gatctgagcc tgggagctct ctggctaact agggaaccca    60
ctgcttaagc ctcaataaag cttgccttga gtgcttcaag tagtgtgtgc ccgtctgttg   120
tgtgactctg gtaactagag atccctcaga ccctttagt cagtgtggaa atctctagc    180 agtggcgccc gaacagggac ttgaaagcga aagggaaacc agaggagctc tctcgacgca   240
ggactcggct tgctgaagcg cgcacggcaa gaggcgaggg gcggcgactg gtgagtacgc   300
caaaattttt gactagcgga ggctagaagg agagagatgg gtgcgagagc gtcagtatta   360
agcgggggag aattagatcg cgatgggaaa aaattcggtt aaggccaggg ggaaagaaaa   420
aatataaatt aaaacatata gtatgggcaa gcagggagct agaacgattc gcagttaatc   480
ctggcctgtt agaaacatca gaaggctgta gacaaatact gggacagcta caaccatccc   540
ttcagacagg atcagaagaa cttagatcat tatataatac agtagcaacc ctctattgtg   600
tgcatcaaag gatagagata aaagacacca aggaagcttt agacaagata gaggaagagc   660
aaaacaaaag taagaccacc gcacagcaag cggccggccg cgctgatctt cagacctgga   720
ggaggagata tgagggacaa ttggagaagt gaattatata aatataaagt agtaaaaatt   780
gaaccattag gagtagcacc caccaaggca aagagaagtg tggtgcagag agaaaaaaga   840
gcagtgggaa taggagcttt gttccttggg ttcttgggag cagcaggaag cactatgggc   900
```

```
gcagcgtcaa tgacgctgac ggtacaggcc agacaattat tgtctggtat agtgcagcag    960
cagaacaatt tgctgagggc tattgaggcg caacagcatc tgttgcaact cacagtctgg   1020
ggcatcaagc agctccaggc aagaatcctg gctgtggaaa gatacctaaa ggatcaacag   1080
ctcctgggga tttggggttg ctctggaaaa ctcatttgca ccactgctgt gccttggaat   1140
gctagttgga gtaataaatc tctggaacag atttggaatc acacgacctg gatggagtgg   1200
gacagagaaa ttaacaatta cacaagctta atacactcct taattgaaga tcgcaaaac   1260 cagcaagaaa agaatgaaca agaattattg gaattagata aatgggcaag tttgtggaat   1320
tggtttaaca taacaaattg gctgtggtat ataaaattat tcataatgat agtaggaggc   1380
ttggtaggtt taagaatagt ttttgctgta ctttctatag tgaatagagt taggcaggga   1440
tattcaccat tatcgtttca gacccacctc ccaaccccga ggggacccga caggcccgaa   1500
ggaatagaag aagaaggtgg agagagagac agagacagat ccattcgatt agtgaacgga   1560
tcggcactgc gtgcgccaat tctgcagaca aatggcagta ttcatccaca attttaaaag   1620 aaaaggggg attgggggt acagtgcagg ggaaagaata gtagacataa tagcaacaga   1680
catacaaact aaagaattac aaaaacaaat tacaaaaatt caaaatttc gggtttatta   1740 cagggacagc agagatccag tttggttagt accgggcccg ctctagagat ccgacgccgc   1800
catctctagg cccgcgccgg ccccctcgca cagacttgtg ggagaagctc ggctactccc   1860
ctgccccggt taatttgcat ataatatttc ctagtaacta tagaggctta atgtgcgata   1920
aaagacagat aatctgttct ttttaatact agctacattt tacatgatag gcttggattt   1980
ctataagaga tacaaatact aaattattat tttaaaaaac agcacaaaag gaaactcacc   2040
ctaactgtaa agtaattgtg tgttttgaga ctataaatat cccttggaga aaagccttgt   2100
taacgcgcgg tgaccctcga ggtcgacggt atcgataagc tcgcttcacg agattccagc   2160
aggtcgaggg acctaataac ttcgtatagc atacattata cgaagttata ttaagggttc   2220
caagcttaag cggccgcgtg gataaccgta ttaccgccat gcattagtta ttaatagtaa   2280
tcaattacgg ggtcattagt tcatagccca tatatggagt tccgcgttac ataacttacg   2340
gtaaatggcc cgcctggctg accgcccaac gacccccgcc cattgacgtc aataatgacg   2400
tatgttccca tagtaacgcc aatagggact ttccattgac gtcaatgggt ggagtattta   2460
cggtaaactg cccacttggc agtacatcaa gtgtatcata tgccaagtac gccccctatt   2520
gacgtcaatg acggtaaatg gcccgcctgg cattatgccc agtacatgac cttatgggac   2580
tttcctactt ggcagtacat ctacgtatta gtcatcgcta ttaccatggt gatgcggttt   2640
tggcagtaca tcaatgggcg tggatagcgg tttgactcac ggggatttcc aagtctccac   2700
cccattgacg tcaatgggag tttgttttgg caccaaaatc aacgggactt tccaaaatgt   2760
cgtaacaact ccgccccatt gacgcaaatg ggcggtaggc gtgtacggtg ggaggtctat   2820
ataagcagag ctggtttagt gaaccgtcag atccgctagc tccaccatgc acctgagaat   2880
ccacgcgaga cggagccctc ctcgccggcc ggcctggacg cttgggatct ggttcctgtt   2940
ctggggatgt atcgtcagct ctgtatggag tcaattgtct tctaatgtag cttcctcctc   3000
ctccacctct tcctcgccgg ggtctcacta cccatacgat gtgccagatt acgccaaccc   3060
cacggagccg ggaatcagac gggttccggg ggcctcagag gtgatccggg agtcgagcag   3120
cacaacaggg atggtcgtcg gcattgtggc tgctgccgcc ctctgcatct tgatcctcct   3180
gtacgccatg tacaagtaca ggaacaggga cgagggctcg ggctcgacct cgggctcggg   3240
```

```
cagcggtggc tctggaggtt ctggtggcag ctctggaggt atgaatggag ctataggagg    3300
tgaccttttg ctcaattttc ctgacatgtc ggtcctagag cgccaaaggg ctcacctcaa    3360
gtacctcaat cccacctttg attctcctct cgccggcttc tttgccgatt cttcaatgat    3420
taccggcggc gagatggaca gctatctttc gactgccggt ttgaatcttc cgatgatgta    3480
cggtgagacg acggtggaag gtgattcaag actctcaatt tcgccggaaa cgacgcttgg    3540
gactggaaat ttcaaggcag cgaagtttga tacagagact aaggattgta atgaggcggc    3600
gaagaagatg acgatgaaca gagatgacct agtagaagaa ggagaagaag agaagtcgaa    3660
aataacagag caaaacaatg ggagcacaaa aagcatcaag aagatgaaac acaaagccaa    3720
gaaagaagag aacaatttct ctaatgattc atctaaagtg acgaaggaat tggagaaaac    3780
ggattatatt catagcggta gtggcggcgg cagtgggggc tctggtgggt caggtggcag    3840
tggcggccct cctcaggacc tgtctgttca tctctggtac gcaggcccca tggagcgggc    3900
aggggcagag agcatcctgg ccaaccgctc ggacgggact ttcttggtgc ggcagagggt    3960
gaaggatgca gcagaatttg ccatcagcat taaatataac gtcgaggtca agcacattaa    4020
aatcatgaca gcagaaggac tgtaccggat cacagagaaa aaggctttcc gggggcttac    4080
ggagctggtg gagttttacc agcagaactc tctaaaggat tgcttcaagt ctctggacac    4140
caccttgcag ttccccttca aggagcctga aaagagagga tctagagggg gatctggtgg    4200
atcaggggt agcggggtt ctggcggacc ggcaggcagt agcggaagca gtattatacc    4260
tgacagggag gttctctacc aggagttcga tgagatggaa gagtgctctc agcacctccc    4320
cggcgcgcct atggaagata ttattcggaa cattgctcgg catctggcgg ttggcgataa    4380
cctcgacaga tcaatctggg gcggctctgg cggctccatg gtgagcgtga tcaagcccga    4440
gatgaagatg aggtactaca tggacggctc cgtcaatggg catgagttca aatcgagggg    4500
tgagggcaca ggcagacctt acgagggaca tcaggagatg acactgcgcg tcacaatggc    4560
cgagggcggg ccaatgcctt tcgccttcga cctggtgtcc cacgtgttct gttacggcca    4620
cagagttttt accaagtacc cagaagagat cccagactat ttcaagcagg cctttcctga    4680
gggcctgtcc tgggagaggt ccctggagtt cgaggacggc ggctccgcct ccgtgagcgc    4740
ccacatcagc ctgaggggca caccttcta ccacaagtcc aagttcaccg gcgtgaactt    4800
ccccgccgac ggccccatca tgcagaacca gagcgtggac tgggagccct caccgagaa    4860
gatcaccgcc agcgacggcg tgctgaaggg cgacgtgacc atgtacctga agctggaggg    4920
cggcggcaac cacaagtgcc agatgaagac cacctacaag gccgccaagg agatcctgga    4980
gatgcccggc gaccactaca tcggccacag gctggtgagg aagaccgagg gcaacatcac    5040
cgagcaggtg gaggacgccg tggcccacct aagggatcc ggtaaaccaa tccccaatcc    5100
tctgctgggt cttgatagca ccttaattaa cggcagtgga gagggcagag aagtctgct    5160
aacatgcggt gacgtcgagg agaatcctgg cccaatgggc aagccactgc atccaacga    5220
caaagtcatg ggaccccggg tttcctactt ggttcggtac atgggttgtg tggaggtcct    5280
ccagtcaatg cgtgccctgg acttcaacac ccggactcag gtcaccaggg aggccatcag    5340
tctggtgtgt gaggctgtgc cggtgctaa ggggcgaca aggaggagaa agccctgtag    5400
ccgcccgctc agctctatcc tggggaggag taacctgaaa tttgctggaa tgccaatcac    5460
tctcaccgtc tccaccagca gcctcaacct catggccgca gactgcaaac agatcatcgc    5520
caaccaccac atgcaatcta tctcatttgc atccggcatg ttagctccct atatcccaga    5580
gtatgtcgcc tatgttgcca aagaccctgt gaatcagaga gcctgccaca ttctggagtg    5640
```

```
tcccgaaggg cttgcccagg atgtcatcag caccattggc caggccttcg agttgcgctt    5700
caaacaatac ctcagggaca tcgagcaggt gccccagcag cccaccctta agatggatta    5760
caaggatgac gacgataagg gctcttccgg gacaggctcc ggatccggca ctagtgcgcc    5820
catcacggcg tacgcccagc agacgagagg cctcctaggg tgtataatca ccagcctgac    5880
tggccgggac aaaaaccaag tggagggtga ggtccagatc gtgtcaactg ctacccaaac    5940
cttcctggca acgtgcatca atggggtatg ctggactgtc taccacgggg ccggaacgag    6000
gaccatcgca tcacccaagg gtcctgtcat ccagatgtat accaatgtgg accaagacct    6060
tgtgggctgg cccgctcctc aaggttcccg ctcattgaca ccctgtacct gcggctcctc    6120
ggacctttac ctggtcacga ggcacgccga tgtcattccc gtgcgccggc gaggtgatag    6180
caggggtagc ctgctttcgc cccggcccat ttcctacttg aaaggctcct cgggggggtcc    6240
gctgttgtgc cccgcgggac acgccgtggg cctattcagg gccgcggtgt gcacccgtgg    6300
agtggctaaa gcggtggact ttatccctgt ggagaaccta gagacaacca tgagatcccc    6360
ggtgttctcg gacaattcct ccccaccagc ggtgtgagtt taaacgaatt cgtcgaggga    6420
cctaataact tcgtatagca tacattatac gaagttatac atgtttaagg gttccggttc    6480
cactaggtac aattcgatat caagcttatc gataatcaac ctctggatta caaaatttgt    6540
gaaagattga ctggtattct taactatgtt gctcctttta cgctatgtgg atacgctgct    6600
ttaatgcctt tgtatcatgc tattgcttcc cgtatggctt tcattttctc ctccttgtat    6660
aaatcctggt tgctgtctct ttatgaggag ttgtggcccg ttgtcaggca acgtggcgtg    6720
gtgtgcactg tgtttgctga cgcaaccccc actggttggg gcattgccac cacctgtcag    6780
ctcctttccg ggactttcgc tttccccctc cctattgcca cggcggaact catcgccgcc    6840
tgccttgccc gctgctggac aggggctcgg ctgttgggca ctgacaattc cgtggtgttg    6900
tcggggaaat catcgtcctt ccttggctgc tcgcctgtg ttgccacctg gattctgcgc    6960
gggacgtcct tctgctacgt cccttcggcc ctcaatccag cggaccttcc ttcccgcggc    7020
ctgctgccgg ctctgcggcc tcttccgcgt cttcgccttc gccctcagac gagtcggatc    7080
tccctttggg ccgcctcccc gcatcgatac cgtcgacctc gatcgagacc tagaaaaaca    7140
tggagcaatc acaagtagca atacagcagc taccaatgct gattgtgcct ggctagaagc    7200
acaagaggag gaggaggtgg gttttccagt cacacctcag gtacctttaa gaccaatgac    7260
ttacaaggca gctgacgcgt gatttttaaaa gaaagggggg actggaagg gctaattcac    7320
tcccactgct ttttgcctgt actgggtctc tctggttaga ccagatctga gcctgggagc    7380
tctctggcta actagggaac ccactgctta agcctcaata aagcttgcct tgagtgcttc    7440
aagtagtgtg tgcccgtctg ttgtgtgact ctggtaacta gagatccctc agacccttt    7500
agtcagtgtg gaaaatctct agca    7524
```

<210> SEQ ID NO 24
<211> LENGTH: 4764
<212> TYPE: DNA
<213> ORGANISM: Artificial Sequence
<220> FEATURE:
<223> OTHER INFORMATION: AAV-ErbB-RASER1C-BID

<400> SEQUENCE: 24

```
cctgcaggca gctgcgcgct cgctcgctca ctgaggccgc ccgggcgtcg gcgacctttt    60
ggtcgcccgg cctcagtgag cgagcgagcg cgcagagagg gagtggccaa ctccatcact   120
```

-continued

```
agggggttcct gcggcctcta gactcgaggc gttgacattg attattgact agttattaat      180
agtaatcaat tacggggtca ttagttcata gcccatatat ggagttccgc gttacataac      240
ttacggtaaa tggcccgcct ggctgaccgc ccaacgaccc ccgcccattg acgtcaataa      300
tgacgtatgt tcccatagta acgccaatag ggactttcca ttgacgtcaa tgggtggagt      360
atttacggta aactgcccac ttggcagtac atcaagtgta tcatatgcca agtacgcccc      420
ctattgacgt caatgacggt aaatggcccg cctggcatta tgcccagtac atgaccttat      480
gggactttcc tacttggcag tacatctacg tattagtcat cgctattacc atggtgatgc      540
ggttttggca gtacatcaat gggcgtggat agcggtttga ctcacgggga tttccaagtc      600 tccacccccat tgacgtcaat gggagtttgt tttggcacca aaatcaacgg gactttccaa      660
aatgtcgtaa caactccgcc ccattgacgc aaatgggcgg taggcgtgta cggtgggagg      720
tctatataag cagagctctc tggctaacta ccggtgctag cgaccatgca cctgagaatc      780
cacgcgagac ggagccctcc tcgccggccg gcctggacgc ttgggatctg gttcctgttc      840
tggggatgta tcgtcagctc tgtatggagt caattgtctt ctaatgtagc ttcctcctcc      900
tccacctctt cctcgccggg gtctcactac ccatacgatg tgccagatta cgccaacccc      960
acggagccgg gaatcagacg ggttccgggg gcctcagagg tgatccggga gtcgagcagc     1020
acaacaggga tggtcgtcgg cattgtggct gctgccgccc tctgcatctt gatcctcctg     1080
tacgccatgt acaagtacag gaacaggggac gagggctcgg gctcgacctc gggctcgggc     1140
agcggtggct ctggaggttc tggtggcagc tctggaggta tgaatggagc tataggaggt     1200
gaccttttgc tcaattttcc tgacatgtcg gtcctagagc gccaaagggc tcacctcaag     1260
tacctcaatc ccacctttga ttctcctctc gccggcttct tgccgattcc ttcaatgatt     1320
accggcggcg agatggacag ctatctttcg actgccggtt tgaatcttcc gatgatgtac     1380
ggtgagacga cggtggaagg tgattcaaga ctctcaattt cgccggaaac gacgcttggg     1440
actggaaatt tcaaggcagc gaagtttgat acagagacta aggattgtaa tgaggcggcg     1500
aagaagatga cgatgaacag agatgaccta gtagaagaag gagaagaaga gaagtcgaaa     1560
ataacagagc aaaacaatgg gagcacaaaa agcatcaaga agatgaaaca caaagccaag     1620
aaagaagaga acaatttctc taatgattca tctaaagtga cgaaggaatt ggagaaaacg     1680
gattatattc atagcggtag tggcggcggc agtgggggct ctggtgggtc aggtggcagt     1740
ggcggccctc ctcaggacct gtctgttcat ctctggtacg caggccccat ggagcgggca     1800
ggggcagaga gcatcctggc caaccgctcg gacgggactt cttggtgcg gcagagggtg      1860 aaggatgcag cagaatttgc catcagcatt aaatataacg tcgaggtcaa gcacattaaa     1920
atcatgacag cagaaggact gtaccggatc acagagaaaa aggctttccg ggggcttacg     1980
gagctggtgg agttttacca gcagaactct ctaaaggatt gcttcaagtc tctggacacc     2040
accttgcagt tccccttcaa ggagcctgaa aagagaggat ctagaggggg atctggtgga     2100
tcagggggta gcgggggttc tggcggaccg gcaggcagta gcggaagcag tattataccct     2160 gacagggagg ttctctacca ggagttcgat gagatggaag agtgctctca gcacctcccc     2220
ggcgcgccta tggaagatat tattcggaac attgctcggc atctggcggt tggcgataac     2280
ctcgacagat caatctgggg cggctctggc ggctccgtga gcaagggcga ggagctgatc     2340
aaggagaaca tgcacatgaa gctgtacatg gaaggcaccg tgaacaacca ccacttcaag     2400
tgcaccaccg aaggggaggg caagccctac gagggcaccc agaccagag gattaaggtg      2460 gtggagggag gcccccctgcc gttcgcattc gacatcctgg ccacctgctt tatgtacggg     2520
```

-continued

| | |
|---|---|
| agcaagacct tcatcaacca cacccagggc atccccgatt tctttaagca gtccttccct | 2580 |
| gagggcttca catgggagag agtcaccaca tacgaagacg ggggcgtgct taccgttacc | 2640 |
| caggacacca gcctccagga cggctgcttg atctacaacg tcaagctcag aggggtgaac | 2700 |
| ttcccatcca acggccctgt gatgcagaag aaaacactcg gctgggaggc caccaccgag | 2760 |
| accctgtacc ccgctgacgg cggcctggaa ggcagatgcg acatggccct gaagctcgtg | 2820 |
| ggcggggggcc acctgcactg caacctgaag accacataca gatccaagaa acccgctaag | 2880 |
| aacctcaaga tgcccggcgt ctactttgtg gaccgcagac tggaaagaat caaggaggcc | 2940 |
| gacaatgaga cctacgtcga gcagcacgag gtggctgtgg ccagatactg cgacctccct | 3000 |
| agcaaactgg ggcacaaact taatggcatg gacgagctgt acaagggatc cggtaaacca | 3060 |
| atccccaatc ctctgctggg tcttgatagc accttaatta acggcagtgg agagggcaga | 3120 |
| ggaagtctgc taacatgcgg tgacgtcgag gagaatcctg gcccaatggg caagccactg | 3180 |
| catcccaacg acaaagtcat gggacccggg gtttcctact tggttcggta catgggttgt | 3240 |
| gtggaggtcc tccagtcaat gcgtgccctg gacttcaaca cccggactca ggtcaccagg | 3300 |
| gaggccatca gtctggtgtg tgaggctgtg ccgggtgcta agggggcgac aaggaggaga | 3360 |
| aagccctgta gccgcccgct cagctctatc ctggggagga gtaacctgaa atttgctgga | 3420 |
| atgccaatca ctctcaccgt ctccaccagc agcctcaacc tcatggccgc agactgcaaa | 3480 |
| cagatcatcg ccaaccacca catgcaatct atctcatttg catccggcat gttagctccc | 3540 |
| tatatcccag agtatgtcgc ctatgttgcc aaagaccctg tgaatcagag agcctgccac | 3600 |
| attctggagt gtccccgaagg gcttgcccag gatgtcatca gcaccattgg ccaggccttc | 3660 |
| gagttgcgct tcaaacaata cctcagggac atcgagcagg tgcccagca gcccacccttt | 3720 |
| aagatggatt acaaggatga cgacgataag ggctcttccg ggacaggctc cggatccggc | 3780 |
| actagtgcgc ccatcacggc gtacgcccag cagacgagag gcctcctagg gtgtataatc | 3840 |
| accagcctga ctggccggga caaaaaccaa gtggagggtg aggtccagat cgtgtcaact | 3900 |
| gctacccaaa ccttcctggc aacgtgcatc aatggggtat gctggactgt ctaccacggg | 3960 |
| gccggaacga ggaccatcgc atcacccaag ggtcctgtca tccagatgta taccaatgtg | 4020 |
| gaccaagacc ttgtgggctg gcccgctcct caaggttccc gctcattgac accctgtacc | 4080 |
| tgcggctcct cggacctttta cctggtcacg aggcacgccg atgtcattcc cgtgcgccgg | 4140 |
| cgaggtgata gcagggggtag cctgctttcg ccccggccca tttcctactt gaaaggctcc | 4200 |
| tcgggggggtc cgctgttgtg ccccgcggga cacgccgtgg gccattcag ggccgcggtg | 4260 |
| tgcacccgtg gagtggctaa agcggtggac tttatccctg tggagaacct agagacaacc | 4320 |
| atgagatccc cggtgttctc ggacaattcc tccccaccag cggtgtgaga tatctaagaa | 4380 |
| ttcctagagc tcgctgatca gcctcgactg tgccttctag ttgccagcca tctgttgttt | 4440 |
| gcccctcccc cgtgccttcc ttgacccctgg aaggtgccac tcccactgtc ctttcctaat | 4500 |
| aaaatgagga aattgcatcg cattgtctga gtaggtgtca ttctattctg gggggtgggg | 4560 |
| tggggcagga cagcaagggg gaggattggg aagagaatag caggcatgct ggggagcggc | 4620 |
| cgcaggaacc cctagtgatg gagttggcca ctccctctct gcgcgctcgc tcgctcactg | 4680 |
| aggccgggcg accaaaggtc gcccgacgcc cgggctttgc ccgggcggcc tcagtgagcg | 4740 |
| agcgagcgcg cagctgcctg cagg | 4764 |

REWIRING ABERRANT CANCER SIGNALING TO A THERAPEUTIC EFFECTOR RESPONSE WITH A SYNTHETIC TWO-COMPONENT SYSTEM

CROSS-REFERENCE TO RELATED APPLICATION

This application is a continuation-in-part of U.S. application Ser. No. 16/044,131, filed Jul. 24, 2018, which claims benefit under 35 U.S.C. § 119(e) of provisional application 62/536,165, filed Jul. 24, 2017, all of which applications are hereby incorporated herein by reference in their entireties.

STATEMENT REGARDING FEDERALLY SPONSORED RESEARCH OR DEVELOPMENT

This invention was made with government support under contract GM098734 awarded by the National Institutes of Health. The government has certain rights in the invention.

TECHNICAL FIELD

The present invention pertains generally to the field of cancer therapy. In particular, the invention relates to methods of targeting anti-cancer therapy to cells exhibiting aberrant signaling associated with cancer pathogenesis by administering synthetic signaling proteins that couple detection of an oncogenic signal to release of therapeutic agents into cancerous cells.

BACKGROUND

Many cancers are driven by mutations that cause constitutive activation of signaling networks promoting cell growth, proliferation, or survival. For example, constitutive activation of ErbB-family receptor tyrosine kinases by mutation or overexpression occurs in 20-30% of solid tumors. Pharmacological approaches to cancer therapy that aim at blocking tumor-promoting signals or initiating an immune response to a cell surface marker suffer from toxicity from inhibition of normal physiological processes utilizing the same signals (FIG. 1A), and often encounter resistance due to target site mutation or compensatory second-site mutations. Pharmacological approaches to induce synthetic lethality specifically in cancer cells by blocking other protein functions are limited by the small set of known synthetic dependencies and also select for resistance.

Thus, therapies that can differentiate between normal and tumorigenic levels of signaling pathway activation, and that are not defeated by increased or maintained pathway activation, would be highly desirable.

SUMMARY

In particular, the invention relates to methods of targeting anti-cancer therapy to cells exhibiting aberrant signaling associated with cancer pathogenesis by administering synthetic signaling proteins that couple detection of an oncogenic signal to release of therapeutic agents into cancerous cells.

In one aspect, the invention includes a method for targeted treatment of a cancer associated with hyperactivity of a receptor tyrosine kinase, the method comprising: a) administering to a subject in need thereof a therapeutically effective amount of a first fusion protein comprising a protease connected to a phosphotyrosine binding (PTB) domain capable of binding to a phosphorylated tyrosine residue on the receptor tyrosine kinase; and b) administering a therapeutically effective amount of a second fusion protein comprising an SH2 domain connected to i) a substrate comprising a cleavage site recognized by the protease and ii) an anti-cancer therapeutic agent, wherein cleavage of the substrate at the cleavage site by the protease of the first fusion protein releases the anti-cancer therapeutic agent from the second fusion protein.

In one embodiment, the receptor tyrosine kinase is a hyperactive ErbB receptor tyrosine kinase.

In another embodiment, the protease is a hepatitis C virus (HCV) NS3 protease.

In another embodiment, the PTB domain comprises the amino acid sequence of SEQ ID NO:4, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the PTB domain is capable of binding to a phosphorylated tyrosine residue on the receptor tyrosine kinase.

In another embodiment, the first fusion protein further comprises a degron, wherein degradation activity of the degron is inhibited by binding of the PTB domain of the fusion protein to the phosphorylated tyrosine residue on the receptor tyrosine kinase such that the fusion protein accumulates preferentially in cancerous cells.

In another embodiment, the degron is an HIF1a degron comprising the amino acid sequence of SEQ ID NO:5, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the degron is capable of promoting degradation of a fusion protein containing it.

In another embodiment, the degron is located in a loop of the PTB domain. In certain embodiments, the PTB domain with the degron inserted comprises the amino acid sequence of SEQ ID NO:6, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the PTB domain is capable of binding to a phosphorylated tyrosine residue on the receptor tyrosine kinase, and the degron is capable of promoting degradation of a fusion protein containing it.

In another embodiment, the PTB is a She PTB.

In another embodiment, the SH2 domain is a Vav1 SH2 domain.

In another embodiment, the tyrosine kinase receptor is constitutively phosphorylated at the tyrosine residue.

In another embodiment, the cancer is selected from the group consisting of breast cancer, colorectal cancer, head and neck cancer, brain cancer, and lung cancer.

Anti-cancer therapeutic agents may include, but are not limited to, chemotherapy, immunotherapy, and biologic agents. In certain embodiments, the anti-cancer therapeutic agent is a pro-apoptotic protein (e.g., BAX, BID) or a transcription factor that activates a pro-apoptotic gene (e.g., FoxO3).

In another embodiment, the anti-cancer therapeutic agent comprises a complex of a catalytically inactive Cas9 (dCas9) with a guide RNA for activating or repressing expression of a gene of interest.

In another embodiment, the dCas9 is fused to a transcriptional activation domain capable of activating transcription of a gene of interest. The gene of interest may be, for example, a pro-apoptotic gene (e.g., BAX, BID) or an immunostimulatory gene (e.g., CSF2). In one embodiment, the transcriptional activation domain is a VP64-p65-Rta (VPR) transcriptional activation domain.

In another embodiment, multiple cycles of treatment are administered to the subject for a time period sufficient to effect at least a partial tumor response, or more preferably, a complete tumor response.

In another embodiment, the method further comprising administering one or more chemotherapeutic agents to the subject.

In another embodiment, the first fusion protein comprises the amino acid sequence of SEQ ID NO: 17, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In another embodiment, the second fusion protein comprises an amino acid sequence selected from the group consisting of SEQ ID NOS:18-22, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In another aspect, the invention includes a method of selectively treating a cancerous cell having a hyperactive ErbB receptor tyrosine kinase in a heterogenous population of cells, the method comprising: a) contacting the population of cells with an effective amount of a first fusion protein comprising a protease connected to a phosphotyrosine binding (PTB) domain that selectively binds to a phosphorylated tyrosine residue on the hyperactive ErbB receptor tyrosine kinase; and b) contacting the population of cells with an effective amount of a second fusion protein comprising an SH2 domain connected to a substrate comprising a cleavage site recognized by the protease and an anti-cancer therapeutic agent, wherein cleavage of the substrate at the cleavage site by the protease of the first fusion protein releases the therapeutic agent from the second fusion protein inside the cancerous cell having the hyperactive ErbB receptor tyrosine kinase.

In another aspect, the invention includes a kit for treating cancer, as described herein, the kit comprising: a) a first fusion protein comprising a protease connected to a phosphotyrosine binding (PTB) domain capable of binding to a phosphorylated tyrosine residue on a hyperactive receptor tyrosine kinase; and b) a second fusion protein comprising an SH2 domain connected to a substrate comprising a cleavage site recognized by the protease and an anti-cancer therapeutic agent. The kit may further comprise means for delivering the fusion proteins to a subject. Additionally, the kit may further comprise instructions for treating cancer according to the methods described herein.

In certain embodiments, the first fusion protein or the second fusion protein is provided by a vector (e.g., a non-viral or viral vector). In some embodiments, the vector is a non-integrating viral vector, for example, including without limitation, an adeno-associated virus.

In certain embodiments, the invention includes a vector system comprising one or more viral vectors comprising: a) a first expression cassette encoding a first fusion protein comprising a protease connected to a phosphotyrosine binding (PTB) domain capable of binding to a phosphorylated tyrosine residue on a hyperactive receptor tyrosine kinase; and b) a second expression cassette encoding a second fusion protein comprising an SH2 domain connected to i) a substrate comprising a cleavage site recognized by the protease and ii) an anti-cancer therapeutic agent, wherein cleavage of the substrate at the cleavage site by the protease of the first fusion protein releases the anti-cancer therapeutic agent from the second fusion protein.

In certain embodiments, the vector system comprises a bicistronic vector comprising the first expression cassette and the second expression cassette. In some embodiments, the bicistronic vector comprises a viral T2A peptide or an internal ribosome entry site (IRES).

In certain embodiments, the vector system further comprises a third expression cassette encoding a viral capsid protein capable of assembly into a viral-like particle.

In certain embodiments, one or more of the viral vectors are non-integrating viral vectors.

In certain embodiments, the vector system comprises a lentivirus vector or an adeno-associated virus vector.

In certain embodiments, the vector system comprises a viral vector comprising a nucleotide sequence selected from the group consisting of SEQ ID NO:23 and SEQ ID NO:24: or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto.

In another aspect, the invention includes a composition comprising a vector system described herein and a pharmaceutically acceptable excipient.

In another aspect, the invention includes a virus-like particle comprising a vector system described herein and a viral capsid protein. In some embodiments, the virus-like particle further comprises a viral envelope protein.

In another aspect, the invention includes a composition comprising a virus-like particle comprising a vector system, as described herein. In some embodiments, the composition further comprises a pharmaceutically acceptable excipient.

In another aspect, the invention includes a method for producing viral-like particles (VLPs), the method comprising: a) transforming a host cell with a vector system described herein; and b) culturing the transformed host cell under conditions whereby capsid proteins are expressed and assembled into VLPs encapsulating the vector system.

In another aspect, the invention includes a method for targeted treatment of a cancer associated with hyperactivity of a receptor tyrosine kinase, the method comprising administering to a subject in need thereof a therapeutically effective amount of a composition comprising a vector system or a VLP comprising the vector system, as described herein. In one embodiment, the receptor tyrosine kinase is a hyperactive ErbB receptor tyrosine kinase. In another embodiment, the tyrosine kinase receptor is constitutively phosphorylated at the tyrosine residue.

The methods of the invention may be used to treat any cancer associated with hyperactivity of a receptor tyrosine kinase (e.g., ErbB), including, but not limited to, breast cancer, ovarian cancer, lung cancer, glioma, colorectal cancer, head and neck cancer, and brain cancer.

In another aspect, the invention includes an isolated cell transformed with a vector system described herein.

In another aspect, the invention includes an isolated cell comprising a virus-like particle comprising a vector system described herein.

In another aspect, the invention includes a kit comprising a vector system or a virus-like particle comprising a vector system described herein and instructions for treating cancer.

The methods of the invention may be combined with any other method of treating cancer, such as, but not limited to, surgery, radiation therapy, chemotherapy, hormonal therapy, immunotherapy, or biologic therapy.

These and other embodiments of the subject invention will readily occur to those of skill in the art in view of the disclosure herein.

BRIEF DESCRIPTION OF THE FIGURES

FIG. 1A shows pharmacological approaches to cancer therapy that aim at blocking tumor-promoting signals or initiating an immune response to a cell surface marker suffer from toxicity from inhibition of normal physiological processes utilizing the same signals.

FIG. 1B shows that signal-induced proteolysis can integrate signal activity over time and function as a generalizable activation mechanism for multiple effectors. FIG. 1C shows molecular modeling suggesting that the mKO2-substrate-CAAX protein should be able to be cleaved by ShcPTB-NS3 bound to ErbB. FIG. 1D shows observed cleavage efficiency by protease and substrate variants. Breast cancer BT-474 cells were transfected with the indicated constructs with or without 0.5 µM ErbB inhibitor lapatinib, which creates an ErbB-inactive condition as a negative control. After 24 hours, cells were lysed for immunoblotting against a v5 epitope tag fused to mKO2 and GAPDH, serving as a loading control. FIG. 1E shows quantitation of percent cleavage of substrates (n=3, error bars represent s.e.m).

FIG. 2A shows a schematic of the dual-targeted system. Substrate is recruited to the active receptor via SH2 which is expected to facilitate the substrate (line between SH2 and cargo) cleavage.

FIG. 2B shows an atomic model of the dual-targeted system. FIG. 2C shows the observed cleavage efficiency by the mon- and dual-targeted system. BT474 cells expressed the indicated constructs for 24 hours and were lysed subsequently for immunoblotting against a v5 epitope tag fused to mKO2 and GAPDH, serving as a loading control. FIG. 2D shows quantitation of observed percent cleavage of the substrates (n=3, error bars represent s.e.m).

FIG. 3A shows a schematic of protease stability regulation upon phosphorylated receptor binding. FIG. 3B shows a structural model of the PTBhif-NS3 (SEQ ID NO: 17). Hif-1a degron (pink) is inserted in the loop near the phosphorylated peptide binding site. FIG. 3C shows the half-life measurement of PTB-NS3 and PTBhif-NS3 in the presence or the absence of the lapatinib, using the SMASh technique (n=3, error bars represent s.e.m.). Values were fit to a monoexponential decay curve to calculate half-lives. FIG. 3D shows the actual ErbB-dependent mKO2 release. BT-474 cells expressed the indicated constructs for 24 hours and were lysed subsequently for immunoblotting against a v5 epitope tag fused to mKO2 and GAPDH, serving as a loading control. FIG. 3E shows quantitation of the observed percent cleavage of the substrates (n=3, error bars represent s.e.m). PTBhif-NS3 and cargo-DEMEEC-SH2-CAAX were designated as the ErbB-RASER system. FIG. 3F shows verification of PTB dependence in ErbB-RASER.

FIG. 4A shows generalization of RASER to multiple ErbB+ cancer cells. The RASER system shows release in ErbB over-activated cancer cell lines such as BT-474 and SK-BR-3 (human breast cancer), 4T1 (mouse breast cancer), SK-OV-3 (human ovarian cancer) and LN299 EGFRvIII (human glioblastoma). Substrate release was blocked by the ErbB inhibitor lapatinib. FIG. 4B shows the generalizability and selectivity of the RASER system is confirmed with fluorescence microscopy. scale bar, 20 µm. FIG. 4C shows that RASER is specific for constitutively active ErbB, rather than ErbB activated by physiological levels of EGF. MCF7 (which express normal ErbB level), SK-BR-3 and BT-474 (aberrant ErbB2 level) cells were transfected with the RASER construct. After 16 hours of protein expression, MCF7 cells were stimulated by 50 nM of EGF for 1 hour to 16 hours as indicated to recapitulate the temporal activation of ErbB. After 32 hours of protein expression, cells were lysed for immunoblotting to detect against phosphorylated ErbBs, mKO2 and GAPDH. FIG. 4D shows quantitation of mKO2 immunoblot signals normalized to GAPDH levels (n=3, error bars represent s.e.m). FIG. 4E shows that RASER output is comparable to the natural downstream effect of the active ErbB. Phospho-ErbB2 and downstream of ErbB, phosphorylated Akt and phosphorylated Erk as well as released mKO2 were detected by western. FIG. 4F shows quantitation of fold induction of Akt, Erk, and RASER (mKO2) between lapatinib treated (ErbB off) and untreated (ErbB on) cells (n=3, error bars represent s.e.m.).

FIG. 5A shows a schematic description of the ErbB-RASER-Bax system. Bax monomer is released in the presence of tumorigenic ErbB signaling activation. FIG. 5B shows results for MCF7 cells (with normal ErbB levels) and BT-474 cells (which overexpress ErbB2) transfected with the ErbB-RASER-Bax construct. After 16 hours of protein expression, cells were lysed for immunoblotting to detect BAX, cleaved PARP and GAPDH. FIG. 5C shows quantitation of cleaved PARP levels in immunoblots of RASER-transfected cells compared to mock-transfected cells (n=3, error bars represent s.e.m.).

FIG. 6A shows a schematic description of the ErbB-RASER-FoxO3 system. Constitutively active FoxO3 (FoxO3-QM) is released in the presence of tumorigenic ErbB signaling activation. The released FoxO3-QM activates pro-apoptotic target genes including Bim. FIG. 6B shows results for MCF7 cells (with normal ErbB levels) and BT-474 cells (which overexpress ErbB2) transfected with the ErbB-RASER-FoxO construct. After 16 hours of protein expression, cells were lysed for immunoblotting to detect FoxO3-QM, cleaved PARP, and GAPDH. FIG. 6C shows quantitation of cleaved PARP levels in immunoblots of RASER-transfected cells compared to mock-transfected cells (n=3, error bars represent s.e.m.).

FIG. 7A shows a schematic of the RASER system for selective transcription with VPRdCas9. FIG. 7B shows results with a plasmid expressing VPRdCas9-substrate-SH2-CAAX or VPRdCas9 or no protein cotransfected with a multi-cistronic plasmid expressing sgRNA, PTBhifNS3, and mClover3 GFP into BT-474 with or without lapatinib. Cells were imaged 24 hours after transfection. FIG. 7C shows quantification of mCherry fluorescence showing that transcriptional activation by ErbB-RASER-VPRCas9 is as efficient as the VPRCas9 positive control and is ErbB-dependent. The mCherry fluorescence was measured in GFP+ cells cotransfected with VPRdCas9-substrate-SH2-CAAX or VPRdCas9 and the multi-cistronic plasmid, after subtraction of mCherry levels in cells cotransfected with the multi-cistronic plasmid alone (n=10).

FIG. 7D shows a schematic of the ErbB-RASER1C-dCas9VP64 system regulating a reporter gene. dCas9 with a VP64 transcriptional activation domain will be released in the presence of constitutively active ErbB to activate TRE3G-mCherry. FIG. 7E shows that ErbB-RASER1C-dCas9VP64 (SEQ ID NO:20) and a TRE3G-directed sgRNA activate TRE3G-mCherry in an ErbB activity-dependent manner in BT-474 cells. mTurquoise is marker for gRNA expression. Scale bar, 100 µm. FIG. 7F shows quantification of (FIG. 7E). AU, arbitrary units. NS, not significant. Differences between conditions were assessed by the Kruskal-Wallis test followed by two-tailed Dunn's posthoc tests. $p=6.5 \times 10^{-8}$ for the overall null hypothesis of no difference between groups (n=50 randomly selected transfected cells). FIG. 7G shows a schematic of the ErbB-RASER1C-dCas9VP64 system regulating endogenous GM-CSF. FIG. 7H shows that RASER activates endogenous GM-CSF in ErbB-hyperactive cells. LN-229:EGFRvIII cells expressing constitutively active ErbB1 and MCF-7 cells with normal ErbB were transfected with ErbB-RASER1C-dCas9VP64, GM-GSF gRNA containing MS2-binding sequences, and MS2-p65-HSF1 (MPH). After 24 h, released GM-CSF was quantified by ELISA (n=3 biological replicates). FIG. 7I shows induction of GM-CSF protein by RASER1C-dCas9VP64 is >4-fold more efficient in LN-229:EGFRvIII cells than in ErbB-normal MCF-7 cells (n=3 biological replicates). All error bars represent s.e.m.

FIG. 8A shows the predicted concentration of released cargo at various times in ErbB-inhibited and ErbB-hyperactive states, using ErbB numbers from BT-474 breast cancer cells. FIG. 8B shows the predicted percent substrate cleavage after 24 h of protein expression. Note percent substrate cleavage is not the same as concentration of cleaved cargo, because the model accounts for the observation that ~50% less total substrate is expressed in ErbB-inhibited conditions. Predicted percent substrate cleavage normalizes for this expression difference whereas the predicted concentration of released cargo does not. FIG. 8C shows the observed cleavage efficiency by protease and substrate variants. BT-474 cells, in which ErbB2 (HER2) is overexpressed and constitutively active, were transfected with the indicated constructs. Cells were then incubated with 0.5 µM lapatinib to inhibit ErbB or without lapatinib to leave ErbB signaling on. After 24 h, cells were lysed for immunoblotting against the V5 epitope tag fused to OFP. GAPDH served as a loading control. FIG. 8D shows the observed percent substrate cleavage. Error bars represent standard error of the mean (s.e.m.) of three biological replicates.

FIG. 9A shows a schematic of the ErbB-RASER1C system, composed of a substrate fusion protein bearing a cargo domain at the C-terminus (NrxnTM-SH2-DEMEEC-cargo) and PTBHIF-pro. FIG. 9B shows both ErbB-RASER1N and ErbB-RASER1C release OFP in an ErbB-dependent manner in BT-474 cells. FIG. 19C shows a comparison of ErbB-RASER1N and ErbB-RASER1C outputs in BT-474 cells. (n=4 and 8 respectively, error bars represent s.e.m.). ErbB responsiveness (output in active relative to inactive states) for RASER1C and RASER1N were 27±7 and 31±6 (mean±s.e.m.), respectively. FIG. 19D shows ErbB responsivity of ErbB-RASER1C and ErbB-RASER1N in MCF-7 cells, which have normal ErbB levels. The cargo is released from ErbB-RASER1N or ErbB-RASER1C only when EGFRvIII is co-expressed.

FIG. 10A shows a schematic description of the ErbB-RASER1C-BID system. OFP-BID will be released in the presence of constitutive ErbB signaling. FIG. 10B shows that ErbB-RASER1C-BID is a single transcription unit encoding both substrate (SEQ ID NO:18) and protease (SEQ ID NO: 17) components that can be expressed at a constant ratio by transfection with a single plasmid or transduction by a single virus. Green arrow, protease cleavage site to release cargo. FIG. 10C shows BT-474 cells, which overexpress ErbB2, and MCF7 cells, which express ErbB at normal levels, transfected with the ErbB-RASER1C-BID construct. After 16 h of protein expression, cells were lysed for immunoblotting to detect cleaved PARP and GAPDH. FIG. 10D shows quantitation of cleaved PARP levels in immunoblots. Error bars represent s.e.m. of three biological replicates. The increased RASER output in BT-474 cells compared to MCF-7 cells was statistically significant by one-tailed unpaired t test. FIG. 10E shows that ErbB-RASER1C-BID virus infection efficiently induced apoptosis in BT-474 cells but not MCF-7 cells. Apoptosis was visually assessed using a fluorescent caspase-3 activity indicator. Scale bar, 100 µm. FIG. 10F shows that apoptosis inductivity of ErbB-RASER1C-BID is generalizable in multiple ErbB1 hyperactive cancer cell lines. H1975, LN-229:EGFRvIII and MCF-7 cells were tested in a same method to (FIG. 10B). FIG. 10G shows quantification of cleaved PARP level, calculated as in (FIG. 10C). FIG. 10H shows that infection with virus expressing ErbB-RASER1C-BID induced apoptosis in H1975 and LN-229:EGFRvIII cells, which express hyperactive ErbB1 mutants, but not MCF-7 cells which does not express hyperactive ErbB. Apoptosis was visually assessed using a fluorescent caspase-3 activity indicator. Scale bar, 100 µm.

FIGS. 11A-11E show RASER as an anti-cancer agent. FIG. 11A shows the cytotoxicity of conventional antitumor agents and ErbB-RASER1C-BID lentivirus in ErbB-hyperactive cancer cell lines (BT-474 and H1975) or ErbB-normal cell lines (MCF-7, MCF-10A and MRC5). Cell viability was measured by fluorescence of the live cell marker Gly-Phe-AFC, then converted to cytotoxicity. Error bars represent s.e.m., n=6 (BT-474, MCF-10A) or 3 (MCF-7, H1975, MRC-5). *$p<0.05$ for indicated comparisons, ***$p<0.001$ for all comparisons between ErbB+ and ErbB− cells. FIG. 11B shows cells that were treated with paclitaxel, ErbB-RASER1C-BID lentivirus, or OFP-only lentivirus. Staurosporine is a positive control for apoptosis. Apoptosis was detected using a caspase-3 fluorescent indicator, and infected cells were detected by OFP. In BT-474 and H1975 cells, apoptosis is induced to higher levels by the RASER virus than by paclitaxel. In MCF10A and MRC5 cells, apoptosis is induced by paclitaxel but not by the RASER virus. Scale bar, 100 µm. FIG. 11C shows testing of AAV-ErbB-RASER1C-BID-RFP specificity in a co-culture model of disseminated disease. Normal ErbB Huh7.5-GFP were differentiated by 1% DMSO treatment for 4 days. Cell tracker orange labeled BxPC3 (ErbB-hyperactive pancreatic cancer) or MCF7 (ErbB-normal) were co-cultured with Huh7.5-GFP monolayer for 24 h. rAAV-RASER1C-BID-RFP and control rAAV were infected at the specified multiplicity of infection (MOI). Cells were imaged and counted 5-7 days later. FIG. 11D shows co-cultures that were infected by rAAV-ErbB-RASER1C-BID-RFP or control rAAV at MOI $3 \times 10^6$ and imaged 7 days later. Scale bar, 100

µm. FIG. 11E shows quantification of cell cytotoxicity from (FIG. 11D). Cell numbers from AAV-RASER1C-BID-RFP infection were subtracted from the cell numbers of control AAV infection, than normalized to control (n=6 for Huh7.5+ MCF-7, n=7 for Huh7.5+BxPC3, error bars represent s.e.m). Only BxPC3 cells showed a significant reduction (p<3.7× $10^{-6}$) while no significant difference was observed in ErbB− cells, Huh7.5, or MCF7. Statistical significance was tested by one-way ANOVA followed by Holm-Sidak's multiple comparisons test.

FIGS. 12A-12F show modeling confirming the benefit of protease-substrate segregation and model parameters. FIG. 12A shows that the integrated signal is higher in oncogenic than in normal signaling. FIG. 12B shows modeling with cells, which were assumed to be spheres having a radius (r) of 10 m. The juxtamembrane space where membrane tethered substrates are located has a height (h) of 10 nm, based on an atomic model (FIG. 1C). FIG. 12C shows calculation of cleavage rates of cytosolic substrate and membrane-localized substrate by cytosolic protease in (FIG. 12B). FIG. 12D shows model parameters and their values. FIG. 12E shows enzymatic parameters of HCV NS3 protease and substrate pairs. To estimate $k_{cat}$ and $K_M$ of NS3(54A) with EDVVCC or DEMEEC substrates, the $k_{cat}$ and $K_M$ values measured for the wild-type NS3 protease domain with these substrates were adjusted by the fold decrease in $k_{cat}$ and increase in $K_M$ caused by the 54A mutation in the HCV protease holoenzyme, consisting of NS3 protease domain and the NS4A β-strand cofactor. FIG. 12F shows numbers of phospho-ErbB proteins per cell. For SK-BR-3 and SK-OV-3, the ratio of phospho-ErbB:total ErbB observed in BT-474 cells and the total number of cell surface ErbB molecules was used to was used to estimate numbers of phospho-ErbB molecules.

FIGS. 13A-13H show modeling parameters are determined using the SMASh technique. FIG. 13A shows a schematic description of the SMASh system. A self-removing degron permits protein production until a HCV NS3 protease inhibitor is added. FIG. 13B shows an experimental scheme for measuring protein half-life, using OFP-DE-MEEC-CAAX as an example. 24 h after transfection with SMASh-tagged OFP-DEMEEC-CAAX, further synthesis is abolished at time 0 by adding the HCV NS3 protease inhibitor asunaprevir (ASV), and protein levels are measured over time. FIG. 13C shows an example immunoblot measuring OFP-DEMEEC-CAAX levels over time.

FIG. 13D shows quantitation of OFP-DEMEEC-CAAX levels over time (n=3, error bar=s.e.m). OFP-DEMEEC-CAAX levels were normalized to GAPDH and fit to an exponential decay curve. FIG. 13E shows degradation rates of the prototypical RASER components. FIG. 13F shows the experimental procedure for obtaining protein synthesis rate with PTB-pro::P2A::OFP-SMASh. Here, PTB-pro refers to PTB-NS3. The construct expressing cells were incubated in ASV for 24 h, synthesis of the protein was permitted by removal of ASV, and the protein levels were measured over time. FIGS. 13G and 13H shows quantitation of OFP levels over time (n=3, error bar=s.e.m). OFP levels, which were normalized to GAPDH and fit to a function assuming a constant synthesis rate and a previously measured degradation rate. The determined synthesis rate of OFP was used to represent that of the protease component upstream to the P2A sequence, as the protease, the P2A peptide, and the downstream open reading frame encoding the substrate are all translated as a single polypeptide.

FIGS. 14A and 14B show modeling of the dual-targeting system. FIG. 14A shows dissociation constants and binding site specificities of candidate SH2 domains. FIG. 14B shows testing of different $K_D$ values of SH2 with the model to determine the optimal affinity of SH2 for the active receptor.

FIG. 15A shows screening of apoptosis-inducing cargo. BT-474 cells were transfected with pro-apoptotic proteins and then lysed for immunoblotting 16 h later. Pro-apoptotic protein levels were assessed by blotting for a fused V5 epitope, and induction of apoptosis was assessed by blotting for cleaved PARP. GAPDH served as a loading control. FIG. 15B shows PARP cleavage in BT-474 cells transfected with ErbB-RASER1C-Bid-OFP is dependent on ErbB activity, as it is blocked by lapatinib.

FIG. 16A shows a schematic description of an ErbB-RASER1N-VPRdCas9 system, similar to the use of RASERC1 in FIG. 5. FIG. 16B shows fluorescence imaging indicating that ErbB-RASER1N-VPRdCas9 induces transcriptional activation of the TRE3G-mCherry reporter gene ErbB2 activation-dependently in BT-474 cells, similar to ErbB-RASERC1-dCas9VP64 in FIG. 6. Scale bar, 500 µm. FIG. 16C shows quantification of (FIG. 16B). AU, arbitrary units. NS, not significant. Differences between conditions were assessed by the Kruskal-Wallis test followed by two-tailed Dunn's posthoc tests. p=8.8×$10^5$ for overall null hypothesis of no difference between groups (n=40 randomly selected transfected cells, error bars represent s.e.m.). FIG. 16D shows screening of gRNAs to activate GM-CSF transcription. MCF-7 cells were transfected with dCas9VP64, a gRNA containing MS2-binding sequences, and MS2-p65-HSF1. After 24 h, GM-CSF mRNA levels were analyzed by quantitative RT-PCR. Numbers above the bars represent mean fold induction over no gRNA, and error bars represent standard deviation of three technical replicates.

FIG. 17A shows that rAAV-RASER1C-BID expresses a single transcription unit encoding the two RASER components, with the far-red fluorescent protein mCardinal fused to the BID BH3 domain as the cargo (SEQ ID NO:19). Green arrow, protease cleavage site to release cargo. FIG. 17B shows a Control rAAV (rAAV-mCardinal) infection in BxPC3 and MCF-7 cells, which verifies that both cell lines are well transduced by rAAV without toxicity from the vector alone. FIG. 17C shows that in ErbB− MCF-7 cells transduced with rAAV-RASER1C-Bid, the mCardinal-BID cargo is primarily membrane-bound, indicating little RASER activation. By contrast, in ErbB+BxPC3 cells, mCardinal-BID is primarily cytosolic, indicating RASER activation. Cells also appear apoptotic in the brightfield image. Scale bars, 100 µm.

FIG. 18A shows Huh7.5-GFP (green) and BxPC3 (magenta) cells, which were cultured separately and infected with rAAV-RASER1C-BID at various MOI. Cells were imaged at 5 days post-infection (DPI). FIG. 18B shows quantitation of imaging indicating there is no difference in the viability of ErbB− Huh7.5-GFP cells, whereas the number of BxPC3 cells is significantly reduced (n=4, error bars represent s.e.m.). FIG. 18C shows Huh7.5-GFP (green) and BxPC3 (magenta) cells, which were co-cultured and infected as described in FIG. 6A. Images were taken on 5 DPI. Colonies of BxPC3 cells were marked with arrows showing the decline in the presence of the RASER virus. FIG. 18D shows that the RASER virus exclusively targets ErbB-hyperactive BxPC3 cells in the co-culture system (n=4, error bars represent s.e.m.) Statistical analyses were done by single-factor ANOVA and Holm-Sidak's multiple comparisons test. Scale bar, 100 µm.

DETAILED DESCRIPTION

Figure 1A:
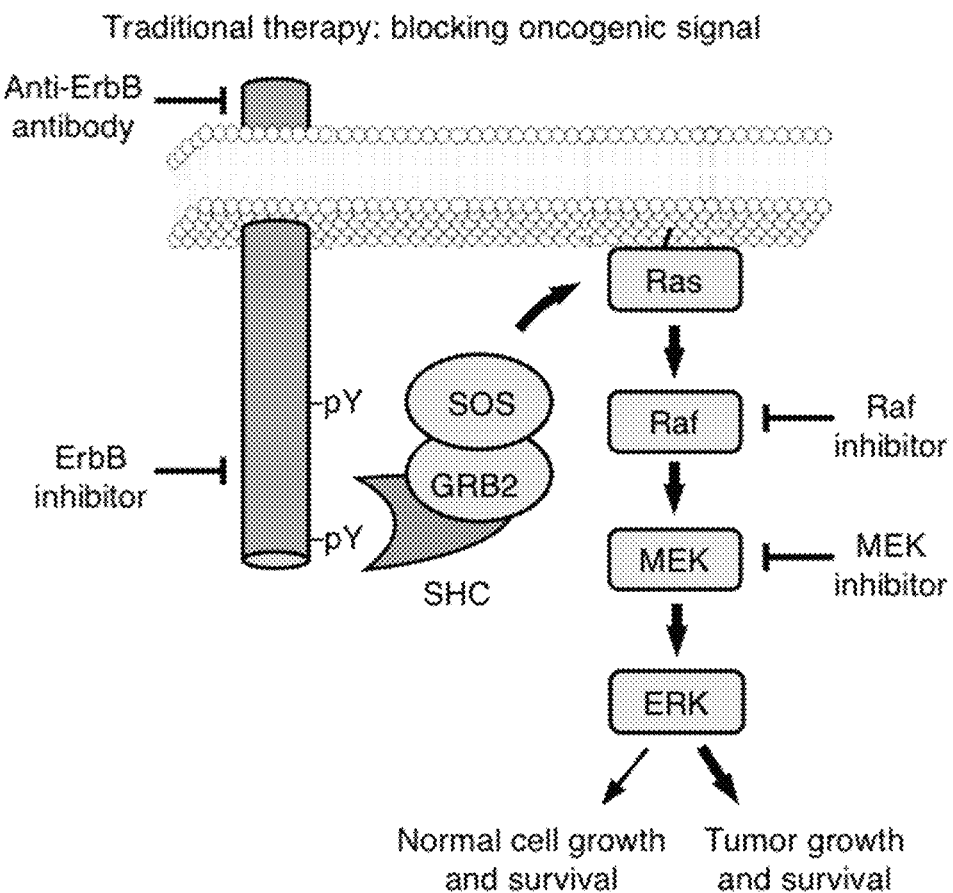
FIGS. 1A-1E show the concept for a molecular integrator of ErbB signaling.

The practice of the present invention will employ, unless otherwise indicated, conventional methods of medicine, pharmacology, chemistry, biochemistry, molecular biology and recombinant DNA techniques and immunology, within the skill of the art. Such techniques are explained fully in the literature. See, e.g., R. A. Weinberg *The Biology of Cancer* (Garland Science, 2$^{nd}$ edition, 2013); *Apoptosis in Cancer Pathogenesis and Anti-cancer Therapy: New Perspectives and Opportunities* (Advances in Experimental Medicine and Biology, C. D. Gregory ed., Springer, 2016); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes a mixture of two or more cells, and the like.

The term "about," particularly in reference to a given quantity, is meant to encompass deviations of plus or minus five percent.

The terms "fusion protein" or "fusion polypeptide," as used herein refer to a fusion comprising a protease in combination with a PTB domain or a fusion comprising an SH2 domain in combination with a substrate for the protease and an anti-cancer therapeutic agent as part of a single continuous chain of amino acids, which chain does not occur in nature. The fusion protein comprising the protease in combination with the PTB domain may further comprise a degron, wherein degradation activity of the degron is inhibited by binding of the PTB domain to a phosphorylated tyrosine residue on a receptor tyrosine kinase such that the fusion protein accumulates preferentially in cancerous cells. The fusion polypeptides may also contain additional sequences, such as targeting or localization sequences, detectable labels, or tag sequences.

The term "cleavage site" refers to the bond (e.g. a scissile bond) cleaved by an agent. A cleavage site for a protease includes the specific amino acid sequence recognized by the protease during proteolytic cleavage and typically includes the surrounding one to six amino acids on either side of the scissile bond, which bind to the active site of the protease and are needed for recognition as a substrate.

As used herein, a "degron" is an amino acid sequence that targets a protein for cellular degradation and specifies degradation of itself and any fusion protein of which it is a part. The degron may promote degradation of an attached polypeptide, for example, through either the proteasome or autophagy-lysosome pathways.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include post-expression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as catalytic activity, ligand binding activity, regulatory activity, degron protein degradation signaling, or fluorescence characteristics.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, colorectal cancer, head and neck cancer, brain cancer, prostate cancer, lung cancer, ovarian cancer, testicular cancer, colon cancer, pancreatic cancer, gastric cancer, hepatic cancer, leukemia, lymphoma, adrenal cancer, thyroid cancer, pituitary cancer, renal cancer, and skin cancer.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

By "therapeutically effective dose or amount" of each of the first and second fusion proteins is intended an amount that when administered in combination brings about a positive therapeutic response with respect to treatment of an individual for cancer. Of particular interest is an amount of the fusion proteins that provides anti-tumor activity, as defined herein. By "positive therapeutic response" is intended the individual undergoing treatment according to the invention exhibits an improvement in one or more symptoms of the cancer for which the individual is undergoing therapy. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, DC, which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S.

Sturrok, and distributed by IntelliGenetics, Inc. (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

The term "transfection" is used to refer to the uptake of foreign DNA or RNA by a cell. A cell has been "transfected" when exogenous DNA or RNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA or RNA moieties into suitable host cells. The term refers to both stable and transient uptake of the genetic material, and includes uptake, for example, of recombinant nucleic acids encoding fusion proteins.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Operably linked" refers to an arrangement of elements wherein the components so described are configured so as to perform their usual function. For example, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence. In another example, a degron operably linked to a polypeptide is capable of promoting degradation of the polypeptide when the proper cellular degradation system (e.g., proteasome or autophagosome degradation) is present. The degron need not be contiguous with the polypeptide, so long as it functions to direct degradation of the polypeptide.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

As used herein, the term "virus-like particle" or "VLP" refers to a nonreplicating, viral shell, derived from any of several viruses discussed further below. A virus-like particle in accordance with the invention is non replicative because it lacks all or part of the viral genome, in particular, replicative and infectious components of the viral genome. VLPs are generally composed of one or more viral proteins, such as, but not limited to those proteins referred to as capsid, coat, shell, surface, structural proteins, or particle-forming polypeptides derived from these proteins, including the proteins described herein. VLPs can form spontaneously upon recombinant expression of capsid proteins in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

The terms "variant" refers to biologically active derivatives of the reference molecule that retain desired activity, such as RNA interference (RNAi), lncRNA inhibition, or transcription factor inhibition. In general, the term "variant" refers to molecules having a native sequence and structure with one or more additions, substitutions (generally conservative in nature) and/or deletions, relative to the native molecule, so long as the modifications do not destroy biological activity and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The terms "subject" refers to a vertebrate subject, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; and birds, including domestic, wild and game birds such as chickens, turkeys and other gallinaceous birds, ducks, geese, and the like. The term does not denote a particular age. Thus, both adult and newborn individuals are intended to be covered.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the development of a method for targeting anti-cancer therapy to cells exhibiting aberrant signaling associated with cancer pathogenesis. The general method utilizes oncogenic signal-induced proteolysis to release tethered therapeutic agents inside cancerous cells, an approach referred to as rewiring of aberrant signaling to effector release (RASER). The inventors have engineered a compact two-component system to sense constitutive ErbB phosphorylation and trigger therapeutic responses (Example 1). Modular sensing and actuation domains in this system allow facile optimization of the sensing and versatile programming of therapeutic outputs. The resulting system responds specifically to constitutively active ErbB, and can be programmed to induce a variety of outputs, including direct induction of apoptosis and transcription of apoptosis-inducing genes. The RASER system is generalizable to various cancers by customizing sensor-actuator modules to specific oncogenic signals.

In order to further an understanding of the invention, a more detailed discussion is provided below regarding RASER systems and methods of using such systems to treat cancer.

A. RASER Systems

In one embodiment, the RASER system is designed for targeted treatment of a cancer comprising a hyperactive receptor tyrosine kinase. A two-component system is used comprising two fusion proteins: i) a first fusion protein comprising a protease connected to a phosphotyrosine binding (PTB) domain capable of binding to a phosphorylated tyrosine residue on a hyperactive receptor tyrosine kinase in a cancerous cell; and ii) a second fusion protein comprising an SH2 domain connected to a substrate comprising a cleavage site recognized by the protease and an anti-cancer therapeutic agent. Cleavage of the substrate by the protease of the first fusion protein releases the therapeutic agent from the second fusion protein inside a cancerous cell.

Exemplary proteases which can be used in the first fusion protein include hepatitis C virus proteases (e.g., NS3 and NS2-3); signal peptidase; proprotein convertases of the subtilisin/kexin family (furin, PC1, PC2, PC4, PACE4, PC5, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N;

insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H. The protease chosen for use in the fusion protein is preferably highly selective for the cleavage site in the cleavable linker. Additionally, protease activity is preferably inhibitable with inhibitors that are cell-permeable and not toxic to the cell or subject under study. For a discussion of proteases, see, e.g., V. Y. H. Hook, Proteolytic and cellular mechanisms in prohormone and proprotein processing, RG Landes Company, Austin, Tex., USA (1998); N. M. Hooper et al., Biochem. J. 321: 265-279 (1997); Z. Werb, Cell 91: 439-442 (1997); T. G. Wolfsberg et al., J. Cell Biol. 131: 275-278 (1995); K. Murakami and J. D. Etlinger, Biochem. Biophys. Res. Comm. 146: 1249-1259 (1987); T. Berg et al., Biochem. J. 307: 313-326 (1995); M. J. Smyth and J. A. Trapani, Immunology Today 16: 202-206 (1995); R. V. Talanian et al., J. Biol. Chem. 272: 9677-9682 (1997); and N. A. Thornberry et al., J. Biol. Chem. 272: 17907-17911 (1997), the disclosures of which are incorporated herein.

In certain embodiments, the protease used in the first fusion protein is a hepatitis C virus (HCV) nonstructural protein 3 (NS3) protease. NS3 consists of an N-terminal serine protease domain and a C-terminal helicase domain. The protease domain of NS3 forms a heterodimer with the HCV nonstructural protein 4A (NS4A), which activates proteolytic activity. An NS3 protease may comprise the entire NS3 protein or a proteolytically active fragment thereof and may further comprise an activating NS4A region.

The cleavage site in the second fusion protein is designed for selective cleavage by the particular protease included in the first fusion protein. The cleavage site includes the specific amino acid sequence recognized by the protease during proteolytic cleavage and typically includes the surrounding one to six amino acids on either side of the scissile bond, which bind to the active site of the protease and are needed for recognition as a substrate. The substrate for the protease in the second fusion protein may contain any protease recognition motif known in the art and is typically cleavable under physiological conditions.

In certain embodiments, an NS3 protease is used in the first fusion protein and a corresponding NS3 cleavage site in the second fusion protein. NS3 nucleic acid and protein sequences may be derived from HCV, including any isolate of HCV having any genotype (e.g., seven genotypes 1-7) or subtype. A number of NS3 nucleic acid and protein sequences are known. A representative NS3 sequence is presented in SEQ ID NO: 1. Additional representative sequences are listed in the National Center for Biotechnology Information (NCBI) database. See, for example, NCBI entries: Accession Nos. YP_001491553, YP_001469631, YP_001469632, NP_803144, NP_671491, YP_001469634, YP_001469630, YP_001469633, ADA68311, ADA68307, AFP99000, AFP98987, ADA68322, AFP99033, ADA68330, AFP99056, AFP99041, CBF60982, CBF60817, AHH29575, AIZ00747, AIZ00744, ABI36969, ABN05226, KF516075, KF516074, KF516056, AB826684, AB826683, JX171009, JX171008, JX171000, EU847455, EF154714, GU085487, JX171065, JX171063; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein or a recombinant polynucleotide encoding such a fusion protein, as described herein. In one embodiment, a slower-cleaving T54A mutant of NS3 protease is used in the first fusion protein (numbering is relative to the reference sequence of SEQ ID NO: 1, and it is to be understood that the corresponding positions in NS3 proteases obtained from other HCV strains are also intended to be encompassed by the present invention).

Exemplary NS3 protease cleavage sites, which can be used in the substrate of the second fusion protein, include the four junctions between nonstructural (NS) proteins of the HCV polyprotein normally cleaved by the NS3 protease during HCV infection, including the NS3/NS4A, NS4A/NS4B, NS4B/NS5A, and NS5A/NS5B junction cleavage sites. For a description of NS3 protease and representative sequences of its cleavage sites for various strains of HCV, see, e.g., *Hepatitis C Viruses: Genomes and Molecular Biology* (S. L. Tan ed., Taylor & Francis, 2006), Chapter 6, pp. 163-206; herein incorporated by reference in its entirety.

The second fusion protein also carries a cargo comprising an anti-cancer therapeutic agent, which is released inside cells upon proteolytic cleavage of the second fusion protein by the protease of the first fusion protein. Exemplary anti-cancer therapeutic agents include chemotherapy, immunotherapy, and biologic agents.

For example, chemotherapy agents include, but are not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

Biologic anti-cancer therapeutic agents include, but are not limited to, small molecule inhibitors or monoclonal antibodies such as, but not limited to, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib;

Bcl-2 inhibitors, such as obatoclax and gossypol; PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar); and monoclonal antibodies, such as Rituximab (marketed as MabThera or Rituxan), Trastuzumab (Herceptin), Alemtuzumab, Cetuximab (marketed as Erbitux), Panitumumab, Bevacizumab (marketed as Avastin), and Ipilimumab (Yervoy).

Immunotherapy anti-cancer therapeutic agents include, but are not limited to, cancer vaccines (e.g., Hepcortespenlisimut-L, Sipuleucel-T), anti-cancer therapeutic antibodies (e.g., Alemtuzumab, Ipilimumab, Ofatumumab, Nivolumab, Pembrolizumab, or Rituximab), cytokines (e.g., interferons, including type I (IFNα and IFNβ), type II (IFNγ) and type III (IFNλ) and interleukins, including interleukin-2 (IL-2)), adjuvants (e.g., polysaccharide-K), and immune checkpoint blockade therapeutic agents.

In some embodiments, the anti-cancer therapeutic agent comprises a pro-apoptotic protein or tumor suppressor, such as, but not limited to, BAX, BID, BAK, BAD, apoptotic protease activating factor 1 (APAF1), p53, p73, pVHL, APC, CD95, ST5, YPEL3, ST7, and ST14. In other embodiments, the anti-cancer therapeutic agent comprises a transcription factor that activates pro-apoptotic genes, such as, but not limited to, Forkhead box O (FOXO) transcription factors (e.g., FoxO3), AP-2 alpha, activating transcription factor 5 (ATF5), C/EBP homologous protein (CHOP), and E2F1.

In yet another embodiment, the anti-cancer therapeutic agent comprises a complex of a catalytically inactive Cas9 (dCas9) with a guide RNA for activating or repressing expression of a gene of interest. An engineered nuclease-deactivated Cas9 (dCas9) is used to allow sequence-specific targeting without cleavage. Nuclease-deactivated forms of Cas9 may be engineered by mutating catalytic residues at the active site of Cas9 to destroy nuclease activity. Any such nuclease deficient Cas9 protein from any species may be used as long as the engineered dCas9 retains sgRNA-mediated sequence-specific targeting. In particular, the nuclease activity of Cas9 from *Streptococcus pyogenes* can be deactivated by introducing two mutations (D 10A and H841A) in the RuvC1 and HNH nuclease domains. Other engineered dCas9 proteins may be produced by similarly mutating the corresponding residues in other bacterial Cas9 isoforms. For a description of engineered nuclease-deactivated forms of Cas9, see, e.g., Qi et al. (2013) Cell 152: 1173-1183, Dominguez et al. (2016) Nat. Rev. Mol. Cell. Biol. 17(1):5-15; herein incorporated by reference in their entireties.

A nuclease-deactivated Cas9 protein can be designed to target particular nucleic acid sequences by altering its guide RNA sequence. A target-specific single guide RNA (sgRNA) comprises a nucleotide sequence that is complementary to a target site, and thereby mediates binding of the dCas9-sgRNA complex by hybridization at the target site. The sgRNA can be designed, for example, with a sequence complementary to a gene regulatory or exonic sequence. The target site will typically comprise a nucleotide sequence that is complementary to the sgRNA, and may further comprise a protospacer adjacent motif (PAM). In certain embodiments, the target site comprises 20-30 base pairs in addition to a 3 base pair PAM. Typically, the first nucleotide of a PAM can be any nucleotide, while the two other nucleotides will depend on the specific Cas9 protein that is chosen. Exemplary PAM sequences are known to those of skill in the art and include, without limitation, NNG, NGN, NAG, and NGG, wherein N represents any nucleotide.

In certain embodiments, the sgRNA comprises 5-50 nucleotides, 10-30 nucleotides, 15-25 nucleotides, 18-22 nucleotides, 19-21 nucleotides, and any length between the stated ranges, including, for example, 10, 11, 12, 13, 14, 15, 16, 17, 18, 19, 20, 21, 22, 23, 24, 25, 26, 27, 28, 29, or 30 nucleotides.

The sgRNAs are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., Tetrahedron (1992) 48:2223-2311; and Applied Biosystems User Bulletin No. 13 (1 Apr. 1987). Other chemical synthesis methods include, for example, the phosphotriester method described by Narang et al., *Meth. Enzymol*. (1979) 68:90 and the phosphodiester method disclosed by Brown et al., *Meth. Enzymol*. (1979) 68:109.

In some embodiments, the dCas9 is fused to a transcriptional activation domain capable of activating transcription of a gene of interest such as a pro-apoptotic gene or an immunostimulatory gene. In one embodiment, the transcriptional activation domain is a VP64-p65-Rta (VPR) transcriptional activation domain.

In certain embodiments, the first fusion protein further comprises a degron to allow control of the release of the anti-cancer therapeutic agent so as to avoid release inside normal noncancerous cells, but allow release in cancerous cells. The degron provides a degradation signal that targets the fusion protein for cellular degradation through either the proteasome or autophagy-lysosome pathway. In the first fusion protein, the degron is operably linked to the protease such that degradation of the protease prevents cleavage and release of the anti-cancer therapeutic agent from the second fusion protein in normal or noncancerous cells. The degron must be operably linked to the protease, but need not be contiguous with it as long as the degron still functions to direct degradation of the protease. Preferably, the degron induces rapid degradation of the fusion protein, including the protease in noncancerous cells.

The first fusion protein is designed such that the degradation activity of the degron is controllable. For example, the degron can be inserted in a loop of the PTB domain such that degron activity is inhibited by binding of the PTB domain to a phosphorylated tyrosine residue of a receptor tyrosine kinase in a cancerous cell. Fusion proteins with degrons so inhibited are not degraded; hence, the fusion protein with its attached active protease accumulates preferentially in cancerous cells. Cleavage of the anti-cancer therapeutic agent from the second fusion protein releases the anti-cancer therapeutic agent inside the cancerous cell.

Any suitable degron may be used, including, but not limited to, N-degrons of type 1 (e.g., degron sequence comprises positively charged amino acids such as Arg, Lys, and His) or type 2 (degron sequences comprises bulky hydrophobic amino acids such as Phe, Trp, Tyr, Leu, and Ile), phosphodegrons (e.g., Cdc4 or Fbw7 degron), or oxygen-dependent degrons (e.g., a hypoxia-inducible factor alpha (HIF-a) degron). Engineered small-molecule-dependent, inducible degrons (e.g. engineered auxin-inducible degrons) may also be used (see, e.g., Nishimura et al. (2009) Nat. Methods 6(12):917-922).

Degrons may further comprise post-translational modifications, including phosphorylation and hydroxylation. For a discussion of degrons and their function in protein degradation, see, e.g., Guharoy et al. (2016) Nat. Commun. 7:10239, Lucas et al. (2017) Curr. Opin. Struct. Biol. 44:101-110, Kanemaki et al. (2013) Pflugers Arch. 465(3): 419-425, Erales et al. (2014) Biochim Biophys Acta 1843 (1):216-221, Schrader et al. (2009) Nat. Chem. Biol. 5(11): 815-822, Ravid et al. (2008) Nat. Rev. Mol. Cell. Biol. 9(9):679-690, Tasaki et al. (2007) Trends Biochem Sci. 32(11):520-528, Meinnel et al. (2006) Biol. Chem. 387(7): 839-851, Kim et al. (2013) Autophagy 9(7):1100-1103, Varshavsky (2012) Methods Mol. Biol. 832:1-11, and Fayadat et al. (2003) Mol. Biol. Cell. 14(3):1268-1278; herein incorporated by reference.

The polypeptides included in the fusion constructs may be connected directly to each other by peptide bonds or may be separated by intervening amino acid sequences (i.e., linkers). The fusion polypeptides may also contain additional sequences, such as tag sequences or detectable labels to facilitate cloning, purification, or detection.

Linker amino acid sequences are typically short, e.g., 20 or fewer amino acids (i.e., 20, 19, 18, 17, 16, 15, 14, 13, 12, 11, 10, 9, 8, 7, 6, 5, 4, 3, 2, or 1). Examples include short peptide sequences which facilitate cloning, poly-glycine linkers (Gly$_n$ where n=2, 3, 4, 5, 6, 7, 8, 9, 10 or more), histidine tags (His$_n$ where n=3, 4, 5, 6, 7, 8, 9, 10 or more), linkers composed of glycine and serine residues or glycine, serine, and alanine residues, wherein n=1, 2, 3, 4, 5, 6, 7, 8, 9, 10, 11, 12, 13, 14, 15 or more), GSAT, SEG, and Z-EGFR linkers. Linkers may include restriction sites, which aid cloning and manipulation. Other suitable linker amino acid sequences will be apparent to those skilled in the art. (See e.g., Argos (1990) J. Mol. Biol. 211(4):943-958; Crasto et al. (2000) Protein Eng. 13:309-312; George et al. (2002) Protein Eng. 15:871-879; Arai et al. (2001) Protein Eng. 14:529-532; and the Registry of Standard Biological Parts (partsregistry.org/Protein_domains/Linker).

In certain embodiments, tag sequences are located at the N-terminus or C-terminus of a fusion protein. Exemplary tags that can be used in the practice of the invention include a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

In certain embodiments, a fusion protein further comprises a detectable label. The detectable label may comprise any molecule capable of detection. Detectable labels that may be used in the practice of the invention include, but are not limited to, radioactive isotopes, stable (non-radioactive) heavy isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. Particular examples of labels that may be used with the invention include, but are not limited to radiolabels (e.g., $^3$H, $^{125}$I, $^{35}$S, $^{14}$C, or $^{32}$P), stable (non-radioactive) heavy isotopes (e.g., $^{13}$C or $^{15}$N), phycoerythrin, Alexa dyes, fluorescein, 7-nitrobenzo-2-oxa-1,3-diazole (NBD), YPet, CyPet, Cascade blue, allophycocyanin, Cy3, Cy5, Cy7, rhodamine, dansyl, umbelliferone, Texas red, luminol, acradimum esters, biotin or other streptavidin-binding proteins, magnetic beads, electron dense reagents, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), Dronpa, Padron, mApple, mCherry, rsCherry, rsCherryRev, firefly luciferase, *Renilla* luciferase, NADPH, beta-galactosidase, horseradish peroxidase, glucose oxidase, alkaline phosphatase, chloramphenical acetyl transferase, and urease. Enzyme tags are used with their cognate substrate. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, CA). As with many of the standard procedures associated with the practice of the invention, skilled artisans will be aware of additional labels that can be used.

B. Production of Fusion Proteins

Fusion proteins can be prepared in any suitable manner (e.g., recombinant expression, purification from cell culture, chemical synthesis, etc.). Fusion proteins may include naturally-occurring polypeptides, recombinantly produced polypeptides, synthetically produced polypeptides, or polypeptides produced by a combination of these methods. Means for preparing fusion proteins are well understood in the art. Fusion proteins are preferably prepared in substantially pure form (i.e. substantially free from other host cell or non-host cell proteins).

In one embodiment, the fusion proteins are generated using recombinant techniques. One of skill in the art can readily determine nucleotide sequences that encode the desired polypeptides using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The sequences encoding polypeptides can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone sequences encoding polypeptides useful in the claimed fusion proteins that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression. (See, also, Examples). As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC 177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego CA ("MaxBac" kit).

Plant expression systems can also be used to produce the fusion proteins described herein. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia-based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases, it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the fusion proteins of the present invention are produced by growing host cells transformed by an expression vector described above under conditions whereby the protein of interest is expressed. The selection of the appropriate growth conditions is within the skill of the art.

In one embodiment, the transformed cells secrete the fusion protein product into the surrounding media. Certain regulatory sequences can be included in the vector to enhance secretion of the protein product, for example using a tissue plasminogen activator (TPA) leader sequence, an interferon (γ or α) signal sequence or other signal peptide sequences from known secretory proteins. The secreted fusion protein product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant fusion proteins substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced fusion proteins are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular fusion proteins of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the fusion proteins can be further purified using conventional techniques well known in the art, such as by any of the techniques described above.

Fusion proteins can also be conveniently synthesized chemically, for example by any of several techniques that are known to those skilled in the peptide art. See, e.g., *Fmoc Solid Phase Peptide Synthesis: A Practical Approach* (W. C. Chan and Peter D. White eds., Oxford University Press, 1st edition, 2000); N. Leo Benoiton, *Chemistry of Peptide Synthesis* (CRC Press; 1st edition, 2005); *Peptide Synthesis and Applications* (Methods in Molecular Biology, John Howl ed., Humana Press, 1st ed., 2005); and *Pharmaceutical Formulation Development of Peptides and Proteins* (The Taylor & Francis Series in Pharmaceutical Sciences, Lars Hovgaard, Sven Frokjaer, and Marco van de Weert eds., CRC Press; 1st edition, 1999); herein incorporated by reference.

In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final peptide or polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, IL 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. These methods are typically used for relatively small polypeptides, i.e., up to about 50-100 amino acids in length, but are also applicable to larger polypeptides, including fusion proteins.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Fusion proteins can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

C. Nucleic Acids Encoding Fusion Proteins

Nucleic acids encoding the first and second fusion proteins can be used to treat cancer. Nucleic acids described herein can be inserted into an expression vector to create an expression cassette capable of producing the fusion proteins in a suitable host cell. In certain embodiments, a vector system is provided comprising one or more viral vectors encoding the first and second fusion proteins, the vector system comprising: a) a first expression cassette encoding the first fusion protein comprising a protease connected to a phosphotyrosine binding (PTB) domain capable of binding to a phosphorylated tyrosine residue on a hyperactive receptor tyrosine kinase; and b) a second expression cassette encoding the second fusion protein comprising an SH2 domain connected to i) a substrate comprising a cleavage site recognized by the protease and ii) an anti-cancer therapeutic agent, wherein cleavage of the substrate at the cleavage site by the protease of the first fusion protein releases the anti-cancer therapeutic agent from the second fusion protein. The first fusion protein and the second fusion protein may be provided by a single vector or separate vectors. The ability of constructs to produce the fusion proteins can be empirically determined (e.g., see Example 1 describing detection using a reporter plasmid that expresses mCherry).

Expression cassettes typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Additionally, 5'—UTR sequences can be placed adjacent to the coding sequence in order to enhance expression of the same. Such sequences may include UTRs comprising an internal ribosome entry site (IRES). Inclusion of an IRES permits the translation of one or more open reading frames from a vector, for example, to allow production of the first and second fusion proteins from the same vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., *BioTechniques* (1997 22 150-161. A multitude of IRES sequences are known and include sequences derived from a wide variety of viruses, such as from leader sequences of picornaviruses such as the encephalomyocarditis virus (EMCV) UTR (Jang et al. *J. Virol.* (1989) 63:1651-1660), the polio leader sequence, the hepatitis A virus leader, the hepatitis C virus IRES, human rhinovirus type 2 IRES (Dobrikova et al., *Proc. Natl. Acad. Sci.* (2003) 100(25): 15125-15130), an IRES element from the foot and mouth disease virus (Ramesh et al., *Nucl. Acid Res.* (1996) 24:2697-2700), a giardiavirus IRES (Garlapati et al., *J. Biol. Chem.* (2004) 279(5):3389-3397), and the like. A variety of nonviral IRES sequences will also find use herein, including, but not limited to IRES sequences from yeast, as well as the human angiotensin II type 1 receptor IRES (Martin et al., *Mol. Cell Endocrinol.* (2003) 212:51-61), fibroblast growth factor IRESs (FGF-1 IRES and FGF-2 IRES, Martineau et al. (2004) *Mol. Cell. Biol.* 24(17):7622-7635), vascular endothelial growth factor IRES (Baranick et al. (2008) *Proc. Natl. Acad. Sci. U.S.A.* 105(12):4733-4738, Stein et al. (1998) *Mol. Cell. Biol.* 18(6):3112-3119, Bert et al. (2006) *RNA* 12(6):1074-1083), and insulin-like growth factor 2 IRES (Pedersen et al. (2002) *Biochem. J.* 363(Pt 1):37-44). These elements are readily commercially available in plasmids sold, e.g., by Clontech (Mountain View, CA), Invivogen (San Diego, CA), Addgene (Cambridge, MA) and GeneCopoeia (Rockville, MD). See also IRESite: The database of experimentally verified IRES structures (iresite.org). An IRES sequence may be included in a vector, for example, to express multiple protein products in combination (e.g., first and second fusion proteins, viral capsid proteins for assembly into VLPs).

Alternatively, a polynucleotide encoding a viral T2A peptide can be used to allow production of multiple protein products (e.g., first and second fusion proteins, viral capsid proteins for assembly into VLPs) from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, Thosea asigna virus and porcine teschovirus-1. See, e.g., Kim et al. (2011) PLoS One 6(4):e18556, Trichas et al. (2008) BMC Biol. 6:40, Provost et al. (2007) Genesis 45(10):625-629, Furler et al. (2001) Gene Ther. 8(11):864-873; herein incorporated by reference in their entireties.

Once complete, the constructs encoding the first and second fusion proteins can be administered to a subject using standard gene delivery protocols. Methods for gene delivery are known in the art. See, e.g., U.S. Pat. Nos. 5,399,346, 5,580,859, 5,589,466. Genes can be delivered either directly to a vertebrate subject or, alternatively, delivered ex vivo, to cells derived from the subject and the cells reimplanted in the subject.

A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference).

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr Pharm Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the first and second fusion proteins include those derived from the pox family of viruses, including vaccinia virus and avian poxvirus. By way of example, vaccinia virus recombinants expressing the first and second fusion proteins can be constructed as follows. The DNA encoding the particular fusion protein coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with. respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia-based infection/transfection system can be conveniently used to provide for inducible, transient expression of the coding sequences of interest (for example, a fusion protein expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991.) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, AL), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or peptide(s) can also be delivered in cochleate lipid compositions similar to those described by Papahadjopoulos et al., Biochem. Biophys. Acta. (1975) 394:483-491. See, also, U.S. Pat. Nos. 4,663,161 and 4,871,488.

The expression cassette of interest may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J. P., et al., J Microencapsul. 14(2):197-210, 1997; O'Hagan D. T., et al., Vaccine 11(2):149-54, 1993.

Furthermore, other particulate systems and polymers can be used for the in vivo or ex vivo delivery of the nucleic acid of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

Recombinant vectors carrying a synthetic expression cassette of the present invention are formulated into compositions for delivery to a vertebrate subject (e.g., mammalian subject, preferably human). These compositions may either be prophylactic (to prevent cancer progression) or therapeutic (to treat cancer). The compositions will comprise a "therapeutically effective amount" of the nucleic acid of interest such that amounts of the first and second fusion proteins can be produced in vivo sufficient to have anti-cancer activity in the individual to which it is administered. The exact amounts necessary will vary depending on the subject being treated; the age and general condition of the subject to be treated; the degree of protection desired; the severity of the condition being treated; the particular anti-cancer therapeutic agent released in cancerous cells by the fusion proteins, and the mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of nucleic acid uptake and/or expression can also be included in the compositions or coadministered.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject or a gene gun, such as the Accell gene delivery system (PowderMed Ltd, Oxford, England).

D. Virus-Like Particles

VLPs can be used to deliver a vector system encoding the first and second fusion proteins to a tumor. VLPs are structures that morphologically resemble viruses, but are devoid of the genetic material required for viral replication. The capsid proteins of viruses self-assemble into virus-like particles (VLP) when expressed in various eucaryotic cells. VLPs spontaneously form when capsid proteins, or variants or fragments thereof capable of producing VLPs, are recombinantly expressed in an appropriate host cell.

Expression vectors comprising capsid coding sequences are conveniently prepared using recombinant techniques. In certain embodiments, expression vectors encode one or more lentivirus structural proteins. For example, expression vectors capable of producing lentivirus VLPs can comprise one or more gag-encoded structural proteins (e.g., P24 capsid protein, P9 capsid protein, P17 matrix protein). In addition, expression vectors may further comprise coding sequences for one or more lentivirus envelope proteins (e.g., Gp120, Gp41). In other embodiments, expression vectors encode one or more AAV structural proteins. For example, expression vectors capable of producing AAV VLPs can comprise one or more AAV structural proteins (e.g., VP1, VP2, and VP3 capsid proteins). VP1 is not essential for capsid formation; therefore, VLPs can be formed from VP1, VP2, and VP3, or just VP2 and VP3.

VLPs can be conveniently prepared using standard recombinant techniques. Polynucleotides encoding viral capsid proteins are introduced into a host cell under conditions suitable for their expression, wherein the viral capsid proteins are assembled into VLPs. Polynucleotide sequences coding for the viral structural proteins (i.e., capsid or envelope proteins) that form VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and the released DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of a capsid protein of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

E. Packaging Cell Lines

Any suitable cell line can be employed to prepare packaging cells for use in packaging a vector system described herein into viral-like particles. Generally, the cells are mammalian cells. In a particular embodiment, the cells used to produce the packaging cell line are human cells. Suitable human cell lines which can be used include, for example, 293 cells (Graham et al. (1977) J. Gen. Virol., 36:59-72, tsa 201 cells (Heinzel et al. (1988) J. Virol., 62:3738), and NIH3T3 cells (ATCC)). Other suitable packaging cell lines include other human cell line derived (e.g., embryonic cell line derived) packaging cell lines and murine cell line derived packaging cell lines, such as Psi-2 cells (Mann et al. (1983) Cell, 33:153-159; FLY (Cossett et al. (1993) Virol., 193:385-395; BOSC 23 cells (Pear et al. (1993) PNAS 90:8392-8396; PA317 cells (Miller et al. (1986) Molec. and Cell. Biol., 6:2895-2902; Kat cell line (Finer et al. (1994) Blood, 83:43-50; GP+E cells and GP+EM12 cells (Markowitz et al. (1988) J. Virol., 62:1120-1124, and Psi Crip and Psi Cre cells (U.S. Pat. No. 5,449,614; Danos, O. and Mulligan et al. (1988) PNAS 85:6460-6464).

F. Pharmaceutical Compositions

A first fusion protein (i.e., comprising a protease connected to a phosphotyrosine binding (PTB) domain capable of binding to a phosphorylated tyrosine residue on a hyperactive receptor tyrosine kinase) and a second fusion protein (i.e., comprising an SH2 domain connected to a substrate comprising a cleavage site recognized by the protease and an anti-cancer therapeutic agent) or nucleic acids or a vector system encoding them as well as VLPs comprising nucleic acids or a vector system encoding them can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the fusion proteins, or nucleic acids encoding them, or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the fusion proteins (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising the first and second fusion proteins described herein are in unit dosage form, meaning an amount of a conjugate or composition of the invention appropriate for a single dose, in a premeasured or pre-packaged form.

The compositions herein may optionally include one or more additional agents, such as other drugs for treating cancer, or other medications used to treat a subject for a condition or disease. Compounded preparations may include the first and second fusion proteins and optionally, one or more drugs for treating cancer, such as one or more chemotherapeutic agents, including, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon. Alternatively, each fusion protein and/or other agents can be contained in separate compositions. The other agents may be co-administered concurrently, before, or after the fusion proteins.

G. Administration

At least one therapeutically effective dose of a first fusion protein (i.e., comprising a protease connected to a phosphotyrosine binding (PTB) domain capable of binding to a phosphorylated tyrosine residue on a hyperactive receptor tyrosine kinase) will be administered in combination with a second fusion protein (i.e., comprising an SH2 domain connected to a substrate comprising a cleavage site recognized by the protease and an anti-cancer therapeutic agent). In some embodiments, the first fusion protein and the second fusion protein are provided by recombinant nucleic acids encoding them (e.g., a vector system encoding them or VLPS comprising nucleic acids or a vector system encoding them).

By "therapeutically effective dose or amount" of each of the first and second fusion proteins is intended an amount that when administered in combination brings about a positive therapeutic response with respect to treatment of an individual for cancer. Of particular interest is an amount of these agents that provides an anti-tumor effect, as defined herein. By "positive therapeutic response" is intended the individual undergoing treatment according to the invention exhibits an improvement in one or more symptoms of the cancer for which the individual is undergoing therapy.

Thus, for example, a "positive therapeutic response" would be an improvement in the disease in association with the therapy, and/or an improvement in one or more symptoms of the disease in association with the therapy. Therefore, for example, a positive therapeutic response would refer to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements.

In certain embodiments, one or more chemotherapeutic agents may also be administered, including, but are not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.50 mg to 5 grams daily, more preferably from about 5 mg to 2 grams daily, even more preferably from about 7 mg to 1.5 grams daily. Preferably, such doses are in the range of 10-600 mg four times a day (q.i.d.), 200-500 mg q.i.d., 25-600 mg three times a day (t.i.d.), 25-50 mg t.i.d., 50-100 mg t.i.d., 50-200 mg t.i.d., 300-600 mg t.i.d., 200-400 mg t.i.d., 200-600 mg t.i.d., 100 to 700 mg twice daily (b.i.d.), 100-600 mg b.i.d., 200-500 mg b.i.d., or 200-300 mg b.i.d.

In certain embodiments, multiple therapeutically effective doses of each of the first and second fusion proteins and, optionally, one or more chemotherapeutic agents will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, the first and second fusion proteins and, optionally, one or more chemotherapeutic agents will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

In some embodiments, the first and second fusion proteins are administered prior to, concurrent with, or subsequent to at least one chemotherapeutic agent. If provided at the same time as the chemotherapeutic agent, the first and second fusion proteins can be provided in the same or in a different composition. Thus, the agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising the first and second fusion proteins and at least one therapeutically effective dose of a pharmaceutical composition comprising at least one chemotherapeutic agent according to a particular dosing regimen. Administration of the separate pharmaceutical compositions can be at the same time (i.e., simultaneously) or at different times (i.e., sequentially, in either order, on the same day, or on different days), so long as the therapeutic effect of the combination of these substances is caused in the subject undergoing therapy.

In other embodiments of the invention, the pharmaceutical composition comprising the agents, such as the first and second fusion proteins and/or chemotherapeutic agents, is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The pharmaceutical compositions comprising the first and second fusion proteins or chemotherapeutic agents may be administered using the same or different routes of administration in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent, such as the fusion proteins in the bloodstream, is equivalent to that obtained with a therapeutically effective dose that is administered parenterally, for example SC, IP, IM, or IV. In some embodiments of the invention, the pharmaceutical composition comprising the first and second fusion proteins are administered by IM or SC injection, particularly by IM or SC injection locally to the region where other therapeutic agent or agents used in cancer therapy are administered.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this agent is preferred with increasing weight of the subject undergoing therapy.

Where a subject undergoing therapy in accordance with the previously mentioned dosing regimens exhibits a partial response, or a relapse following a prolonged period of remission, subsequent courses of therapy may be needed to achieve complete remission of the disease. Thus, subsequent to a period of time off from a first treatment period, a subject may receive one or more additional treatment periods with the first and second fusion proteins. Such a period of time off between treatment periods is referred to herein as a time period of discontinuance. It is recognized that the length of the time period of discontinuance is dependent upon the degree of tumor response (i.e., complete versus partial) achieved with any prior treatment periods of concurrent therapy with these therapeutic agents.

H. Kits

The invention also provides kits comprising one or more containers holding compositions comprising a first fusion protein (i.e., comprising a protease connected to a phosphotyrosine binding (PTB) domain capable of binding to a phosphorylated tyrosine residue on a hyperactive receptor tyrosine kinase) and a second fusion protein (i.e., comprising an SH2 domain connected to a substrate comprising a cleavage site recognized by the protease and an anti-cancer therapeutic agent), or recombinant nucleic acids encoding them (e.g., a vector system encoding them or VLPs comprising nucleic acids or a vector system encoding them) and optionally one or more other drugs for treating cancer.

Compositions can be in liquid form or can be lyophilized, as can individual fusion proteins or nucleic acids. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for treating cancer with the fusion proteins, nucleic acids/vector system encoding them, or VLPs, as described herein. The package insert can be an unapproved draft package insert or can be a package insert approved by the Food and Drug Administration (FDA) or other regulatory body.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Rewiring Aberrant Cancer Signaling to Therapeutic Effector Response with a Synthetic Two-Component System Introduction Instead of attempting to block oncogenic signaling or protein function, we considered a novel approach to cancer therapy where signals driving oncogenesis are instead co-opted to trigger therapeutic responses via rewiring by synthetic signal transduction pathways. Our concept is that genes encoding synthetic signaling components can be introduced into cells and the encoded proteins can query whether a specific oncogenic signal exists. If this system can differentiate constitutive oncogenic signals from normal transient signals, then the therapeutic program could be specifically triggered only in cancer cells, preventing undesired toxicities in normal tissues.

For rewiring of endogenous oncogenic signals to therapeutic outputs to become a feasible approach, the components should be compatible with delivery by known non-toxic gene-expression vectors. We thus aimed for our system to be encodable within the 4.7-kilobase packaging limit of adeno-associated virus, a non-integrating virus with a strong clinical safety record. For therapeutic versatility, the ability to program the system to produce multiple specific outputs would be highly desirable as well. These conditions suggested that a system that can activate selected endogenous genes would be ideal, as useful therapeutic functions can be found in the library of 20,000 genes in the human genome.

Several natural and engineered systems demonstrate that two-component systems can link the presence of a molecular signal to transcription with high responsivity. In bacterial two-component systems, ligand binding to a receptor kinase induces it to phosphorylate a cytosolic transduction protein, inducing its latent transcription factor activity. The Notch receptor protein responds to presentation of the ligand Delta on contacting cell surfaces by undergoing presenilin-mediated transmembrane cleavage, allowing a polypeptide fragment to translocate to the nucleus to induce gene transcription. Presenilin-mediated cleavage has been found to occur even when Notch and Delta extracellular domains are swapped for other protein-protein interactions, allowing transcriptional programs to be linked to specific cell-cell contacts. In the synthetic TANGO system, two synthetic proteins are expressed to detect GPCR ligands. Ligand induces binding between one protein, a fusion of G-protein-coupled receptor (GPCR) and tobacco etch virus (TEV) protease, to the other protein, a fusion of beta-arrestin, TEV substrate, and a transcription factor, leading to transcription factor release. However, while the above synthetic systems exist to link transmembrane or extracellular ligands to gene transcription, simple synthetic systems for linking intracellular oncogenic signals to therapeutic outputs do not exist. Such a system would need to solve three challenges: First, the presence of an endogenous oncogenic signal would need to be converted to a therapeutic output, and second, oncogenic levels of the signal would need to be differentiated from normal patterns of signal activation.

In this study, we describe the engineering and application of a compact two-component system that senses constitutive ErbB phosphorylation and triggers therapeutic responses. We have created a system for detecting hyperactive signaling from ErbB receptor tyrosine kinases, which occurs in a large fraction of solid tumors, especially breast, colorectal, head and neck, brain, and lung cancers. This system comprises two proteins, one of which contains a viral protease domain and is expressed as a cytosolic protein, and the other which consists of a therapeutic cargo protein that is linked to a membrane-targeting sequence via a substrate sequence for the cytosolic viral protease. Both proteins are recruited to active ErbB receptor intracellular domains by phosphotyrosine-binding domains so that the protease induces release of cargo from the membrane tether in proportion to ErbB signal duration. The use of a modular architecture facilitates customization of inputs and outputs and optimization of the system as a whole. Mathematical modeling of the entire system enables in silico optimization of several biochemical parameters to further enhance system responsivity. The resulting system for ErbB-specific rewiring of aberrant signaling to effector release (ErbB-RASER) responds specifically to constitutively active ErbB, is as sensitive to constitutive ErbB signaling as native growth- and survival-promoting kinase pathways, and can be programmed to induce a variety of outputs including direct induction of apoptosis and transcription of apoptosis-inducing genes.

Results

Figure 1B:
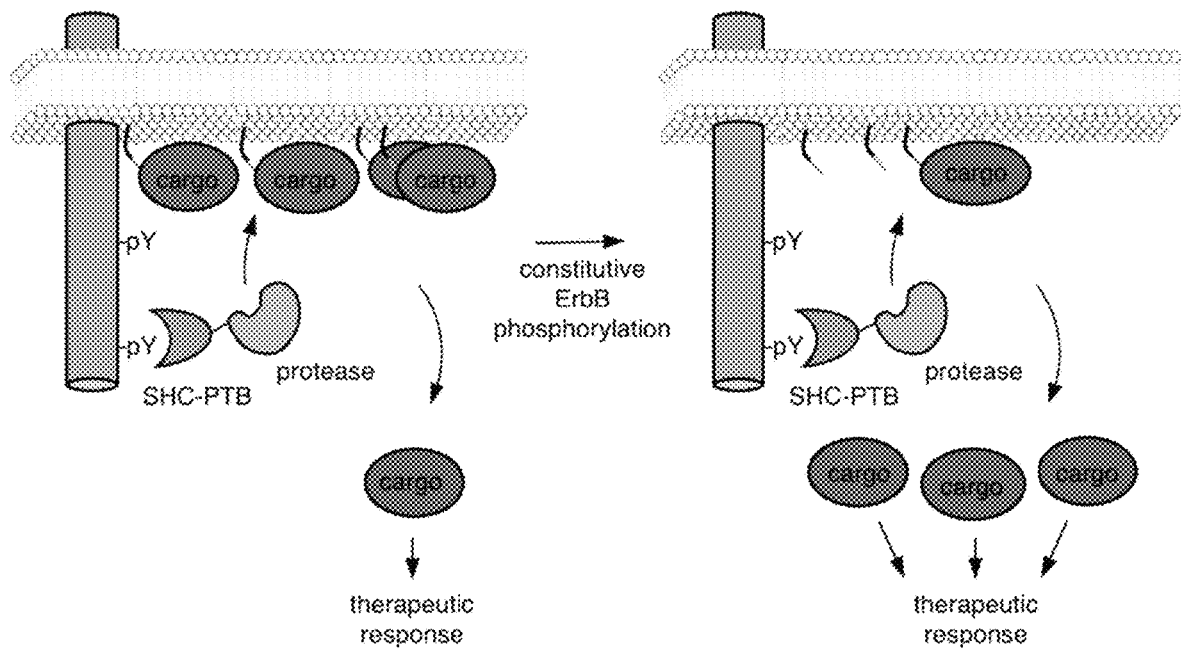

The Concept of a Synthetic Two-Component System Based on Signaling Dependent Proteolysis To specifically sense a cancer state, we considered how to detect the difference between physiological signaling, which is transient, with oncogenic signaling, which is constitutive. To link signaling to various outputs, we considered how to activate a variety of different effectors using a common mechanism. We conceived the idea of using signal-induced proteolysis as a mechanism for integrating signal activity over time, and as a generalizable activation mechanism for multiple effectors (FIG. 1B). Specifically, because proteolysis is irreversible, the products can accumulate proportionally to protease activity integrated over time. Secondly, many effector domains can be functionally inactivated by appending a motif that localizes the effector away from a required site of function, which can then be reversed by proteolytic removal of the localization motif. We termed this general approach of linking cargo release to oncogenic signaling via a two-component protease-substrate system as Rewiring of Aberrant Signaling to Effector Release (RASER).

As a first system, we aimed to detect the ErbB-family of receptor tyrosine kinases (RTKs), which include ErbB1 (HER1, EGFR) and ErbB2 (HER2, Neu) which are constitutively phosphorylated in 30% of solid tumors. Oncogenic mutations or overexpression of ErbB leads to its constitutive phosphorylation at cytoplasmic tyrosine residues, which then bind to phosphotyrosine-binding (PTB) and SH2 domains. Domains that bind to active ErbB proteins have been extensively characterized, including measurements of binding affinities in high-throughput experiments. Furthermore, as the site of corecruitment will be the membrane, the substrate-effector fusion, can be prelocalized to the membrane. This should sequester the substrate away from the majority of cytosolic protease molecules, reducing basal cleavage rates. To then achieve proteolysis in a manner dependent on the integrated ErbB signal over time, we postulated we could bring a weak protease to the membrane in a signal-dependent manner by attaching a phosphotyrosine binding (PTB) domain that can bind to active ErbB receptor. The binding of the fusion proteins to the oncogenic signal should effectively concentrate the substrate in the vicinity of the protease, allowing for higher enzyme occupancy by substrate and thereby faster effector release.

Figure 1C:
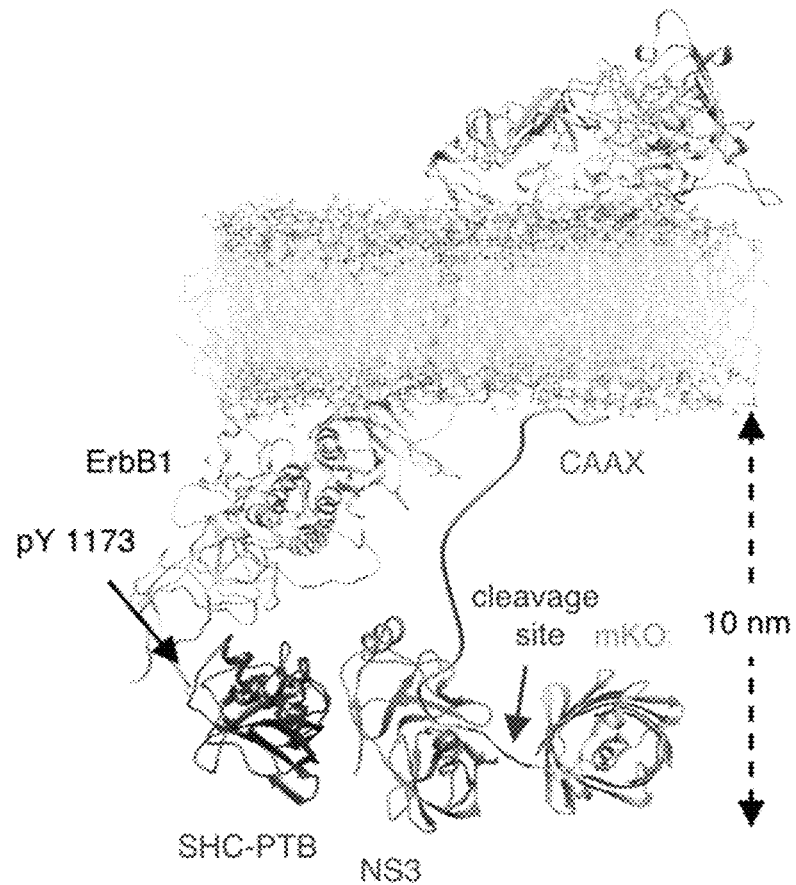
Figure 1D:
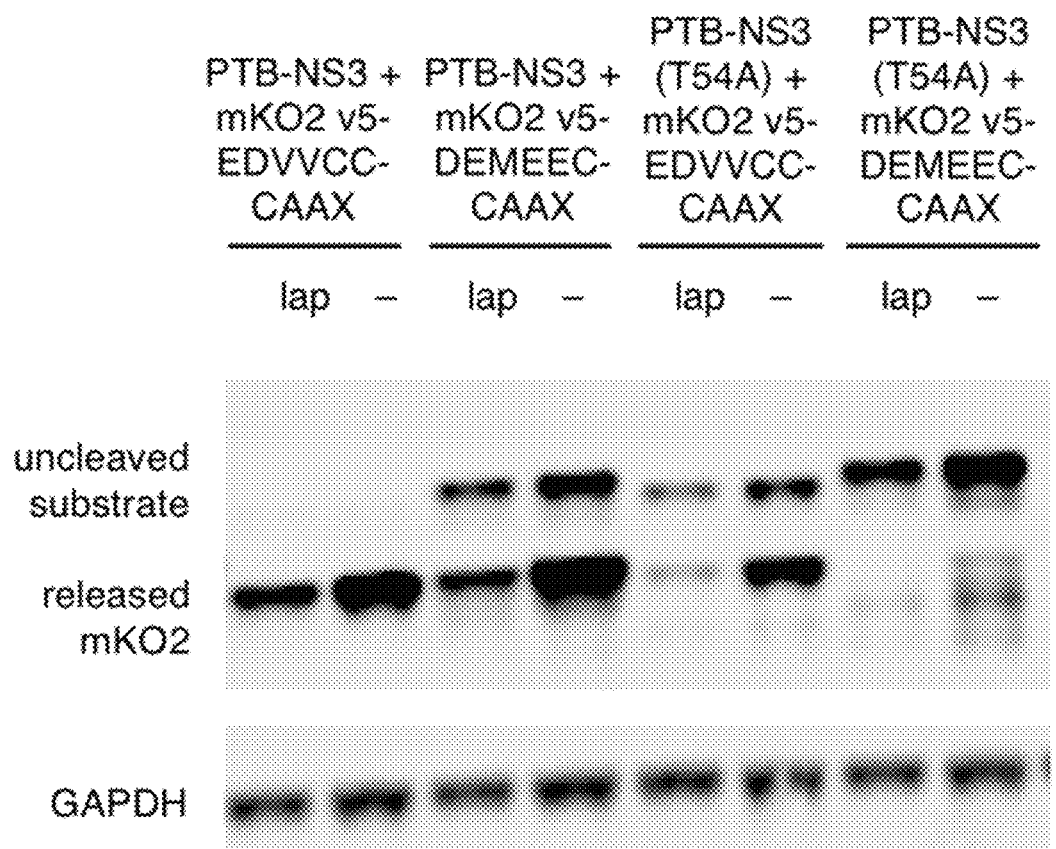
Figure 1E:
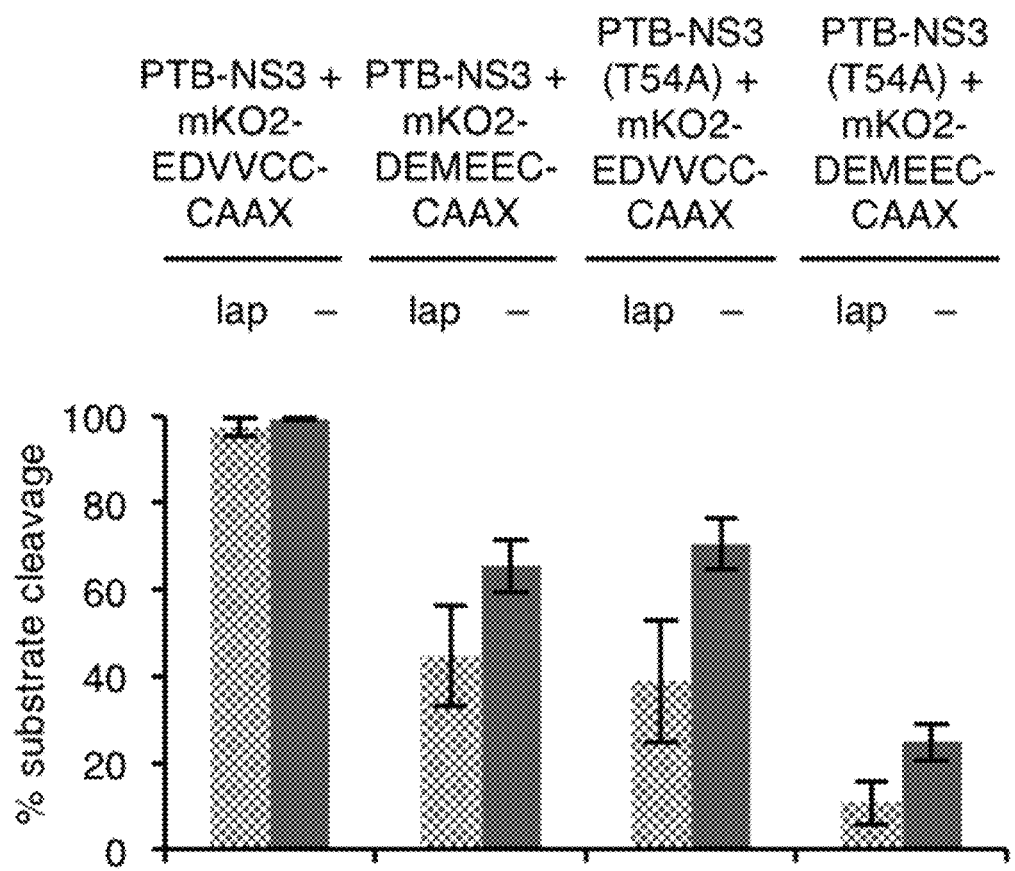

To test this concept, we first constructed a simple system. We considered which domain to fuse to HCV NS3 protease to recruit it to the membrane in an ErbB phosphorylation-dependent manner. High affinity should maximize receptor occupancy, so we selected Shc PTB as the targeting domain for the protease, as it has the highest known affinity for phosphorylated ErbB RTKs. We localized substrate to the membrane via a CAAX farnesylation signal and used the orange fluorescent protein mKO2 as a mock effector. Molecular modeling suggested the mKO2-substrate-CAAX protein should be able to be cleaved by ShcPTB-NS3 bound to ErbB (FIG. 1C). We tested combinations of two HCV protease variants and two substrate variants in BT-474 breast cancer cells, which overexpress ErbB2. For a matched ErbB-inactive control, we treated the same cells with the ErbB kinase inhibitor lapatinib. We observed a range of cleavage efficiencies, with nearly complete cleavage with medium-speed protease and high-affinity substrate (FIGS. 1D and 1E). These results thus also allow us to rule out TEV protease, which exhibits even faster cleavage of its substrate. However, they also showed that a simple system with only protease recruitment to the receptor is insufficient for inducible effector release from a farnesyl membrane anchor. Specifically, the maximum fold induction observed (approximately 2.5-fold) was with the slower-cleaving T54A mutant of NS3 protease, but cleavage efficiency was low, at only 25% after 24 hours. Thus, a system comprising a PTB-protease fusion and membrane-bound substrate did not demonstrate robust ErbB-dependent effector release.

Dual Targeting of RASER Components Improves Responsivity

Figure 2A:
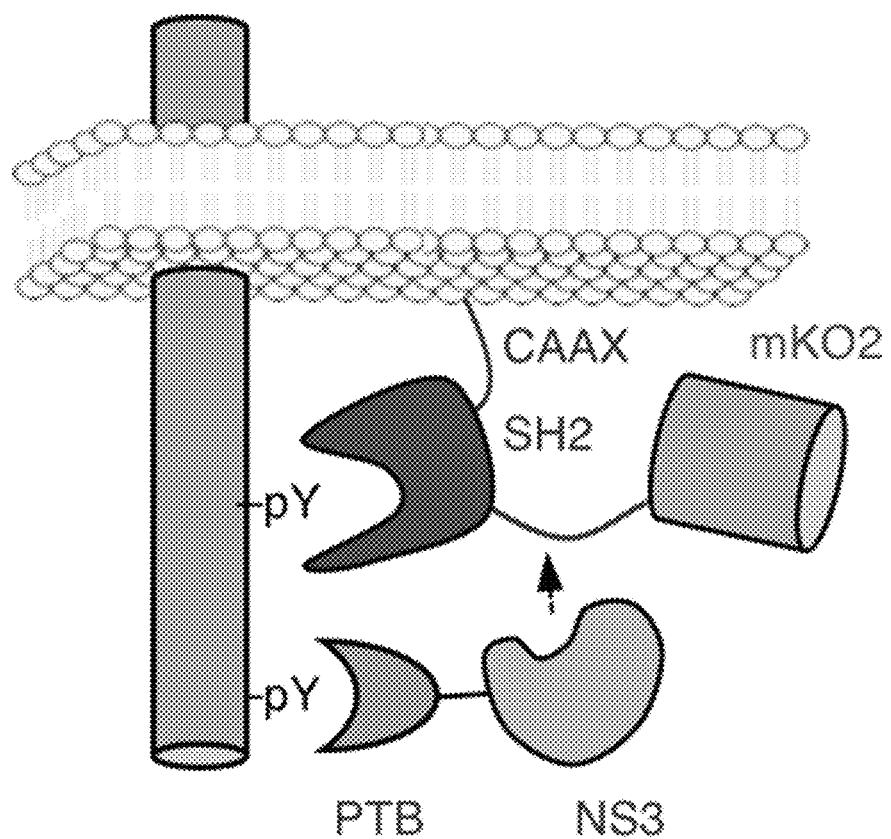
FIGS. 2A-2D show that dual-targeting of protease and substrate to the receptor complex improves oncogenic ErbB signal-dependent proteolysis.

To improve dynamic range, we explored the possibility of binding protease and substrate simultaneously to active ErbB receptors (FIG. 2A). Like PTB, fused to the protease, the other domain is fused to the substrate and the effector. The binding of both fusion proteins to the same oncogenic signal will concentrate protease to the site of substrate, increasing the total number of proteases engaged with substrate. To achieve accumulation of effector, we note that the substrate-effector fusion needs to be capable of rapid dissociation, and substrate needs to be in excess over protease.

Figure 2B:
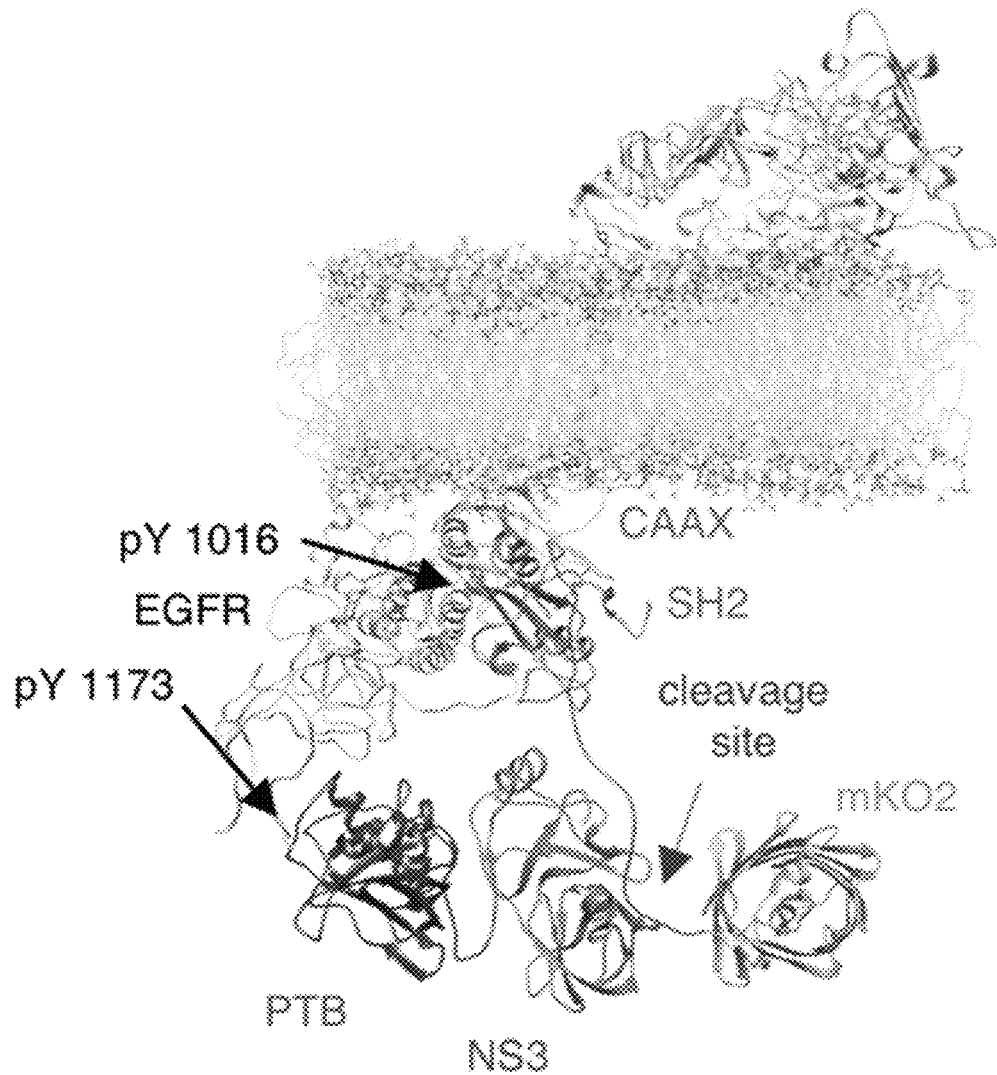
Figure 2C:
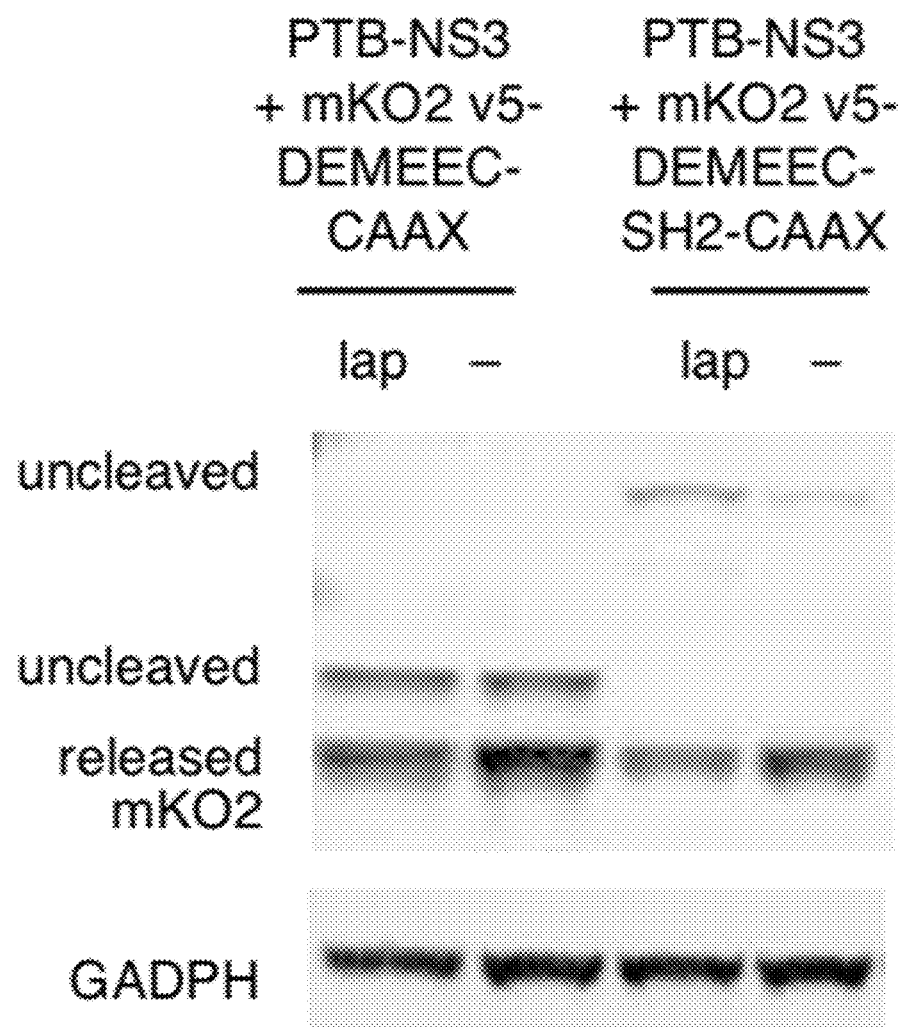
Figure 2D:
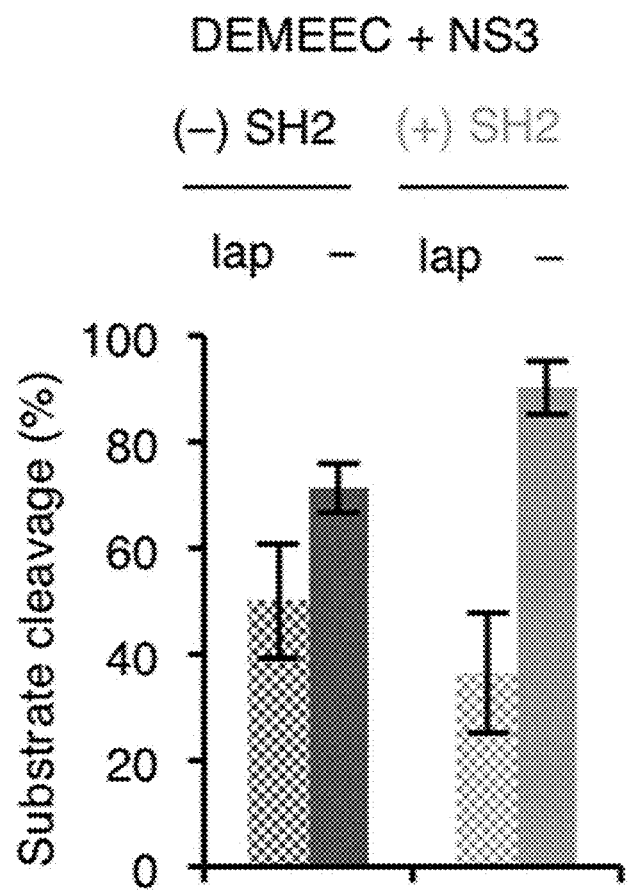

We first used structural modeling to select SH2 domains targeting active ErbB for the substrate that do not interfere with PTB-protease binding. In ErbB1, Tyr1016 is close enough to allow protein binding there to be cleaved by a ShcPTB-protease fusion binding at Tyr1173 (FIG. 2B), yet does not confer steric hindrances between the protease and the substrate components. When substrate was targeted to active receptor using a Vav1 SH2 domain, cleavage was robustly dependent on constitutive ErbB activity (FIGS. 2C and 2D).

Destabilizing Protease to Further Improves Responsivity

Figure 3A:
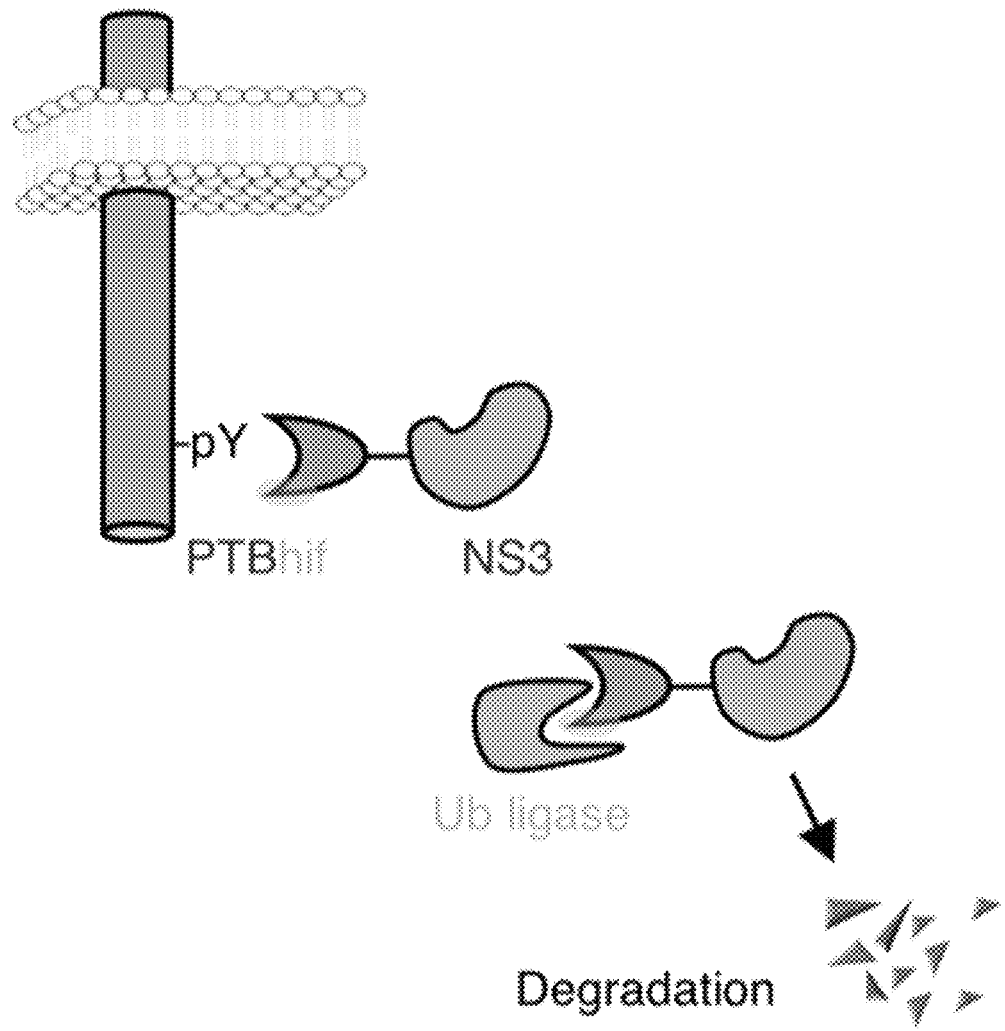
FIGS. 3A-3F show that reduction of protease stability improves the selectivity of ErbB activation-dependent proteolysis.
Figure 3B:
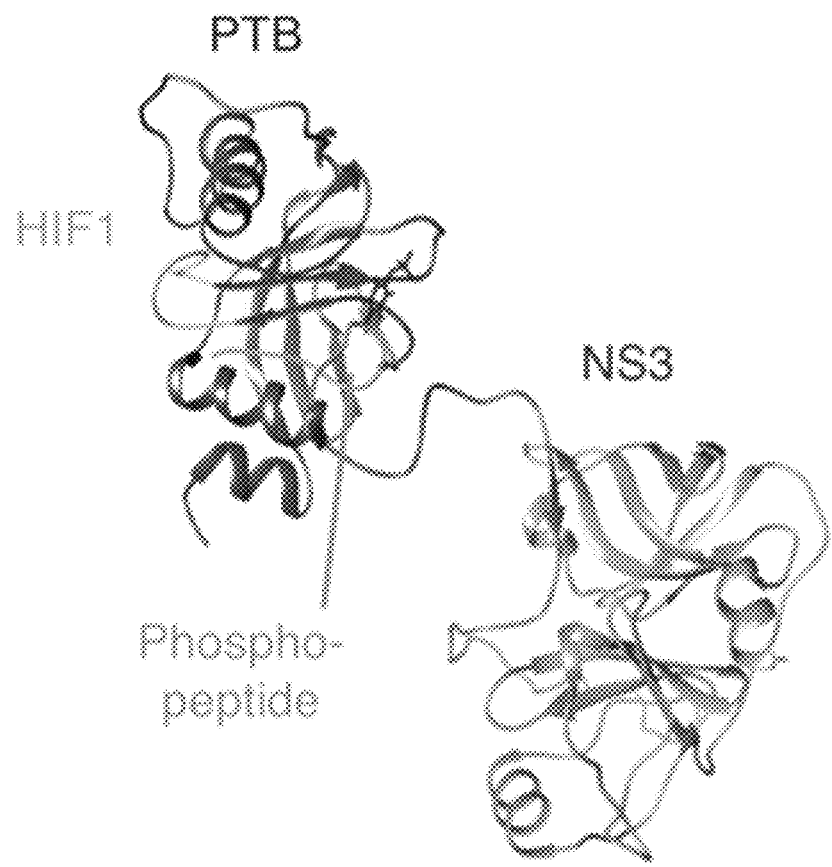
Figure 3C:
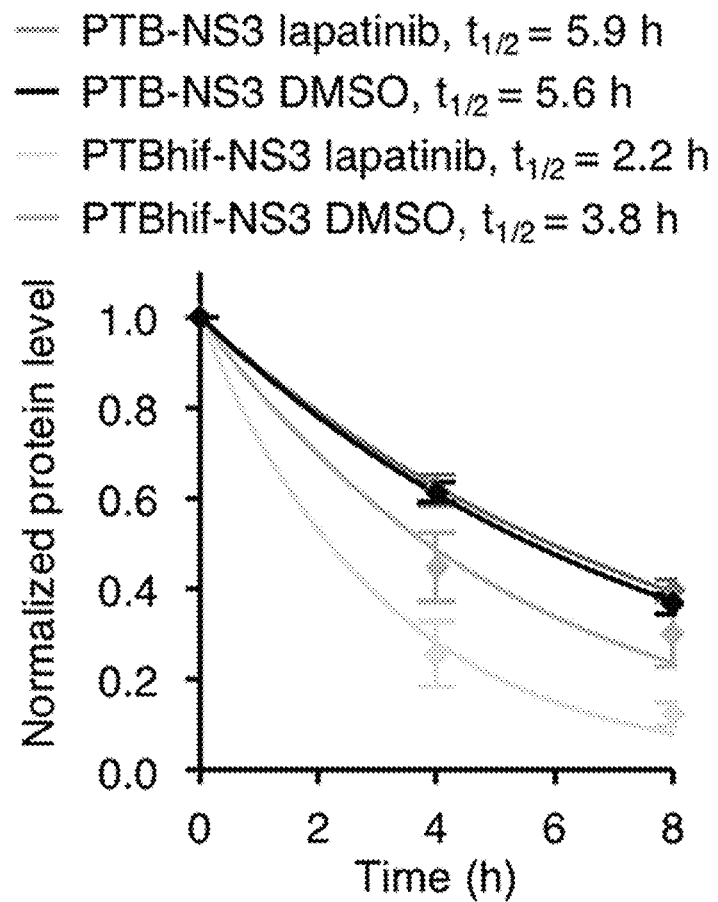
Figure 3D:
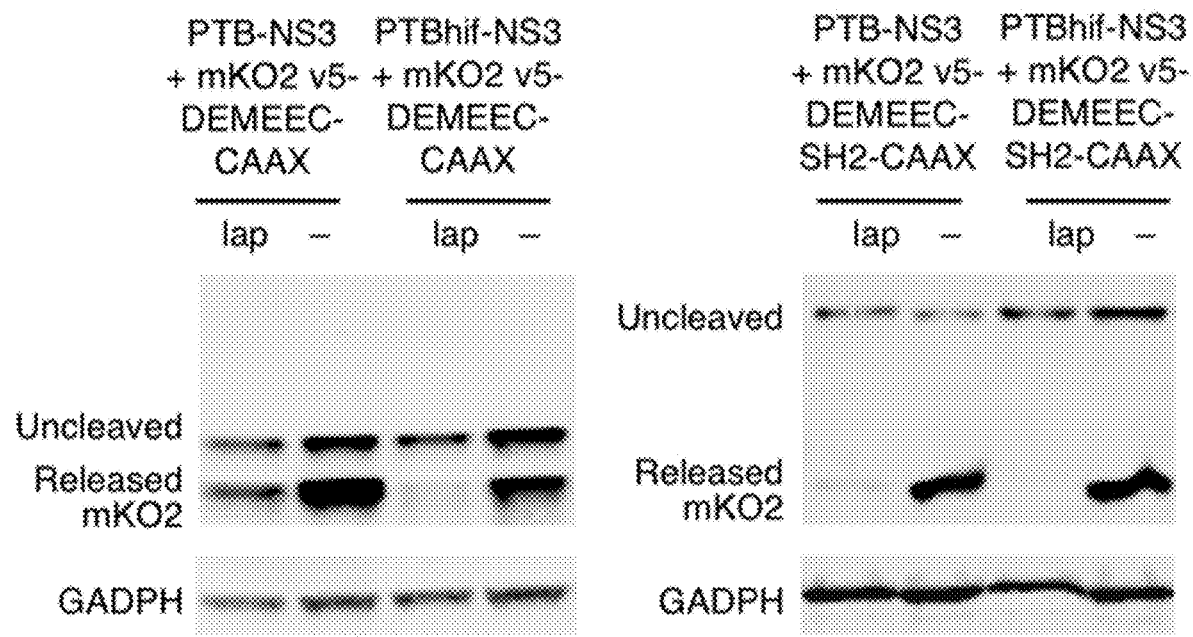
Figure 3E:
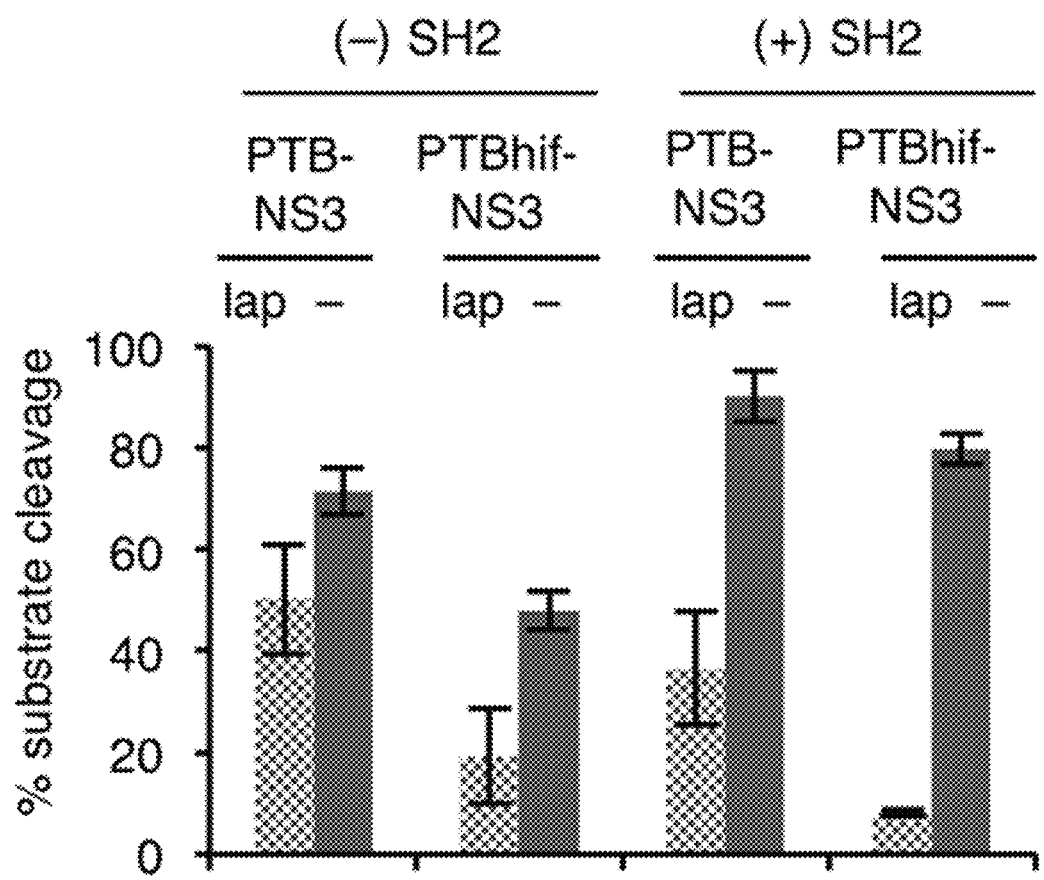
Figure 3F:
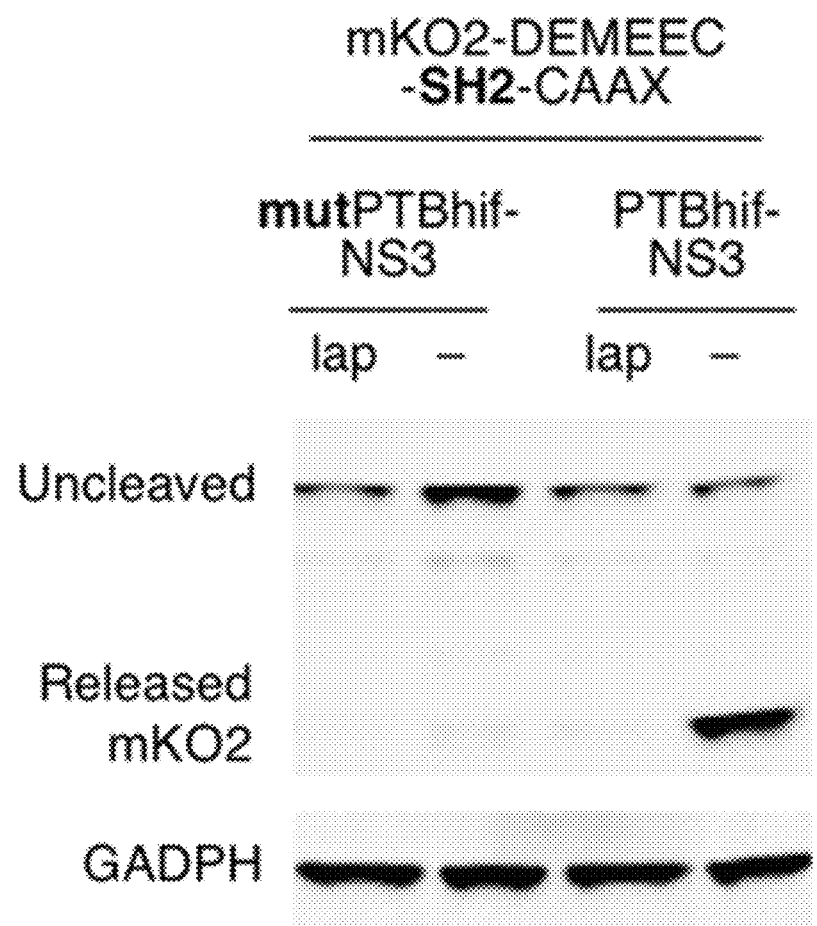

How can we further suppress activity in the ErbB-off state? In addition to using receptor to localize protease to the membrane, we conceived an idea of using the receptor to stabilize the protease. We hypothesized we could attach a degron to the protease whose function would be blocked by receptor binding (FIG. 3A). This would have the beneficial effect of allowing protease to accumulate preferentially in cancer cells, where it will induce more effector release. Using molecular modeling, we placed a short peptide degron from HIF1a in a loop of the PTB domain near the phosphopeptide-binding groove (FIG. 3B). Our empirical experiments confirmed a shorter half-life in the absence of the phosphorylated receptor than in the presence of the active receptor (FIG. 3C). Substrate cleavage in the absence of ErbB activity was reduced, increasing the fold induction of substrate release in ErbB-overexpressing cancer cells (FIGS. 3D and 3E). The best performance was observed with PTBhif-NS3 (SEQ ID NO:17) and cargo-DEMEEC-SH2-CAAX, so these two proteins was designated as the ErbB-RASER system. Finally, we confirmed that performance of ErbB-RASER depends on both PTB and SH2 targeting (FIG. 3F).

Figure 4A:
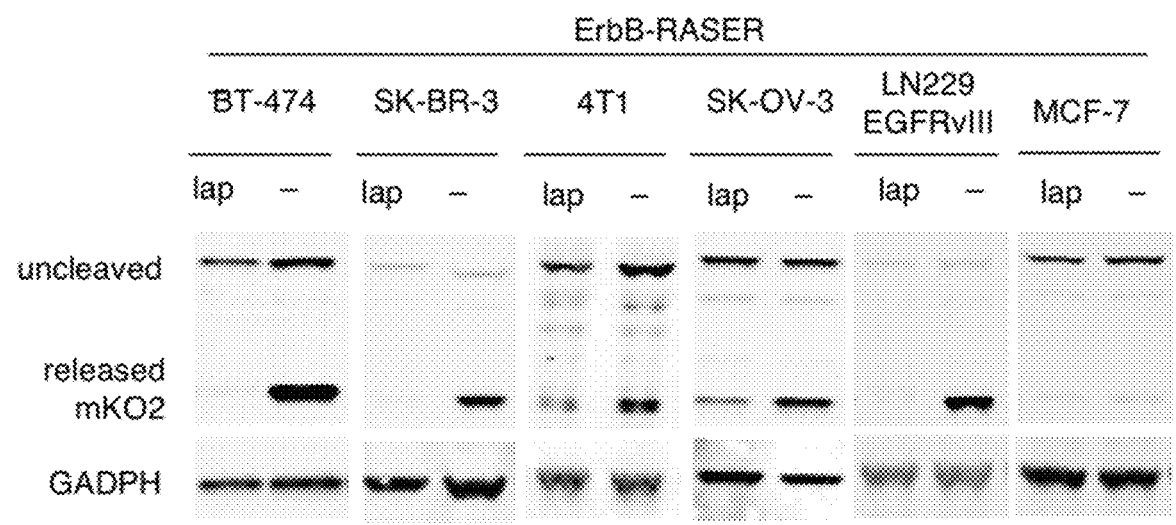
FIGS. 4A-4F show characterization of the RASER system.
Figure 4B:
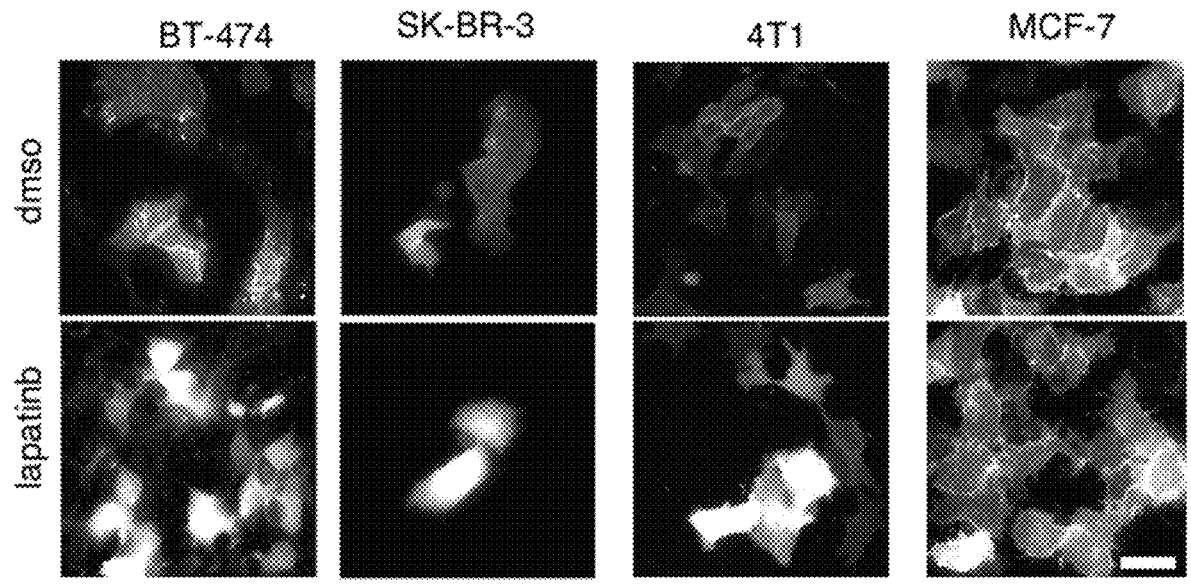
Figure 4C:
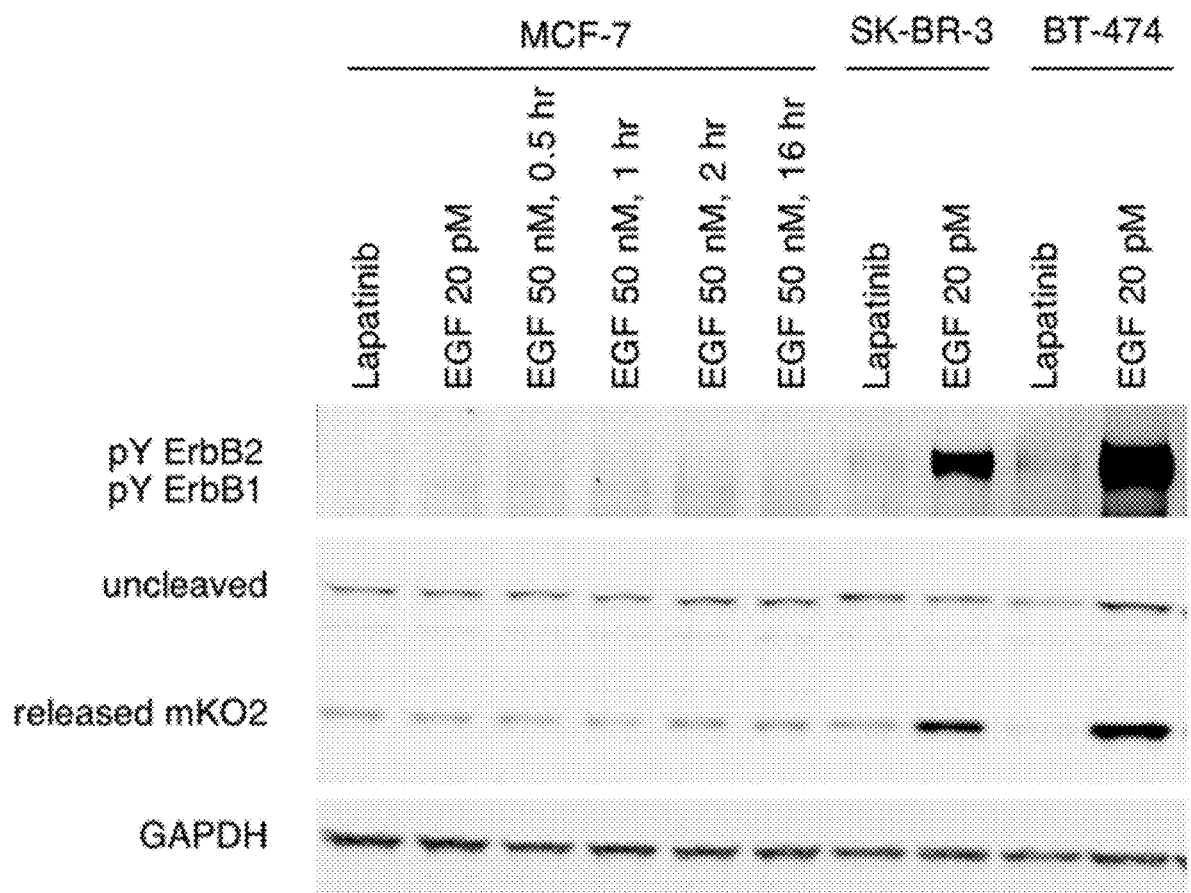
Figure 4D:
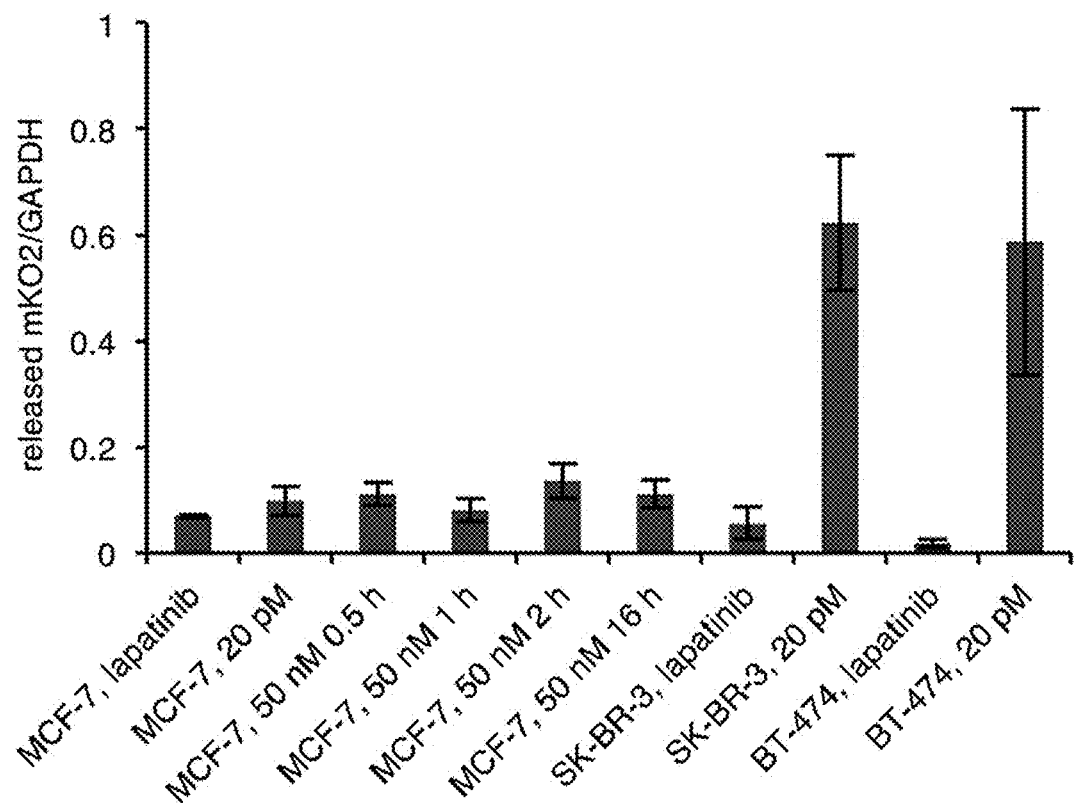

We tested the specificity and inducibility of ErbB-RASER in various cancer cell lines. To test the generalizability of ErbB-RASER for cells with hyperactive ErbB, we tested substrate cleavage in various cancer cell lines known to overexpress ErbB, including glioblastoma, breast cancer, and ovarian cancer cells. ErbB-RASER expression resulted in cargo release in an ErbB-dependent manner all ErbB-overexpressing lines, but not in MCF-7 breast cancer cells, which express normal levels of ErbB receptors (FIGS. 4A and 4B). To test the specificity of ErbB-RASER for cells with constitutively active ErbB, we tested whether EGF stimulation of MCF-7 cells could induce ErbB-RASER cargo release. ErbB1 in MCF-7 is phosphorylated upon EGF stimulation while ErbB2 in SK-BR-3 and BT-474 is constitutively phosphorylated (FIGS. 4C and 4D). We found that cargo release in MCF-7 remains low even after EGF stimulation, whereas cargo release is high in SK-BR-3 and BT-474 cells even without EGF. Thus, as intended, RASER selectively responds to aberrant cancer signaling rather than normal ErbB activation.

Figure 4E:
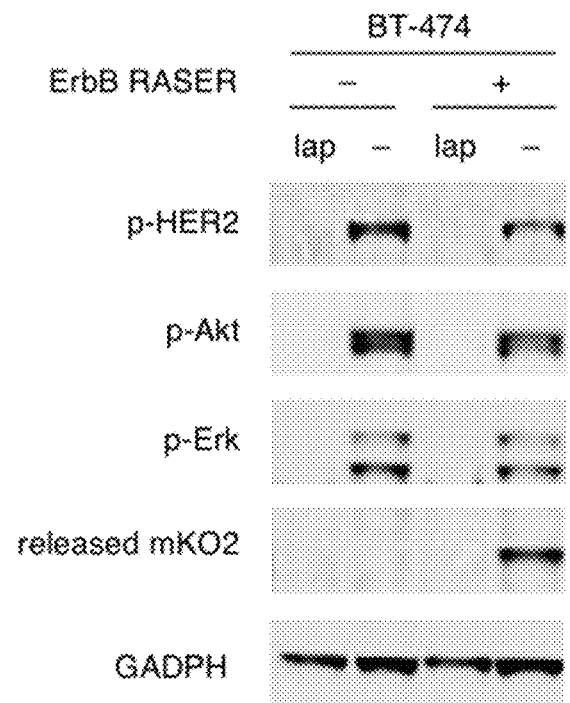
Figure 4F:
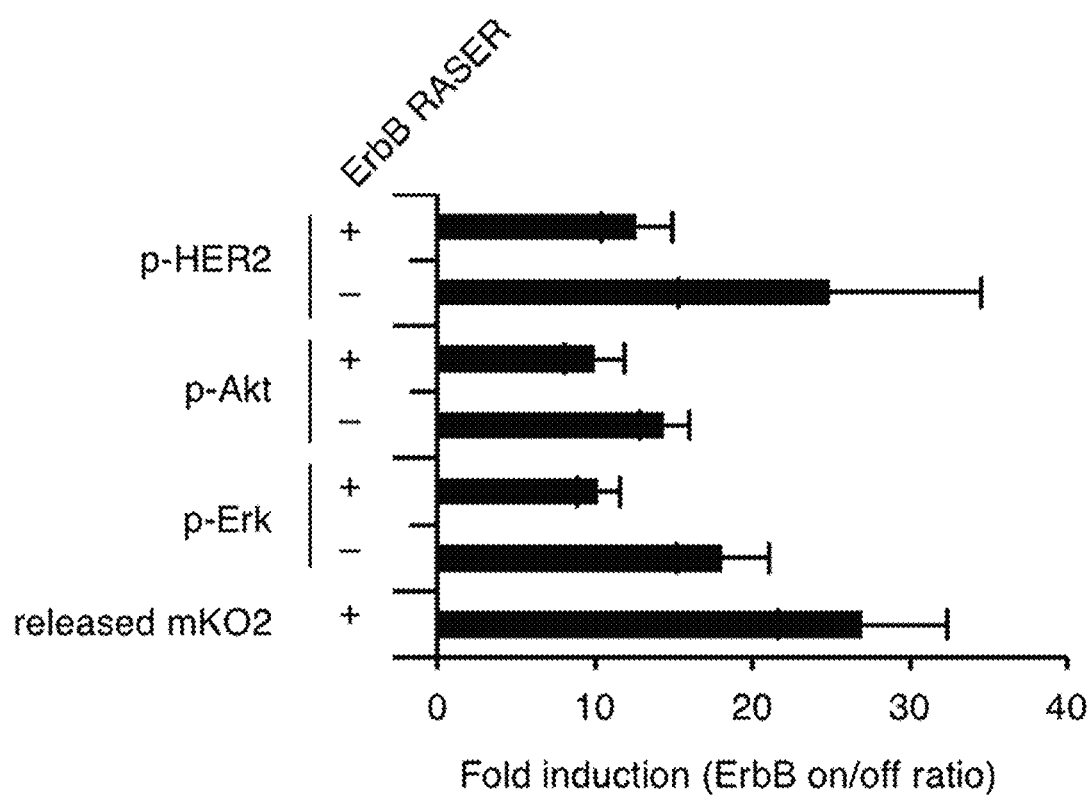

Interestingly, the complete RASER system showed a similar or larger degree of dependence on ErbB activation than endogenous signaling pathways. For example, mKO2 release increased 27-fold in BT-474 cells between ErbB-inhibited and ErbB-active states, whereas endogenous Akt and Erk phosphorylation levels increased only 14- and 18-fold (FIGS. 4E and 4F).

Programming of RASER with a Variety of Outputs

Figure 5A:
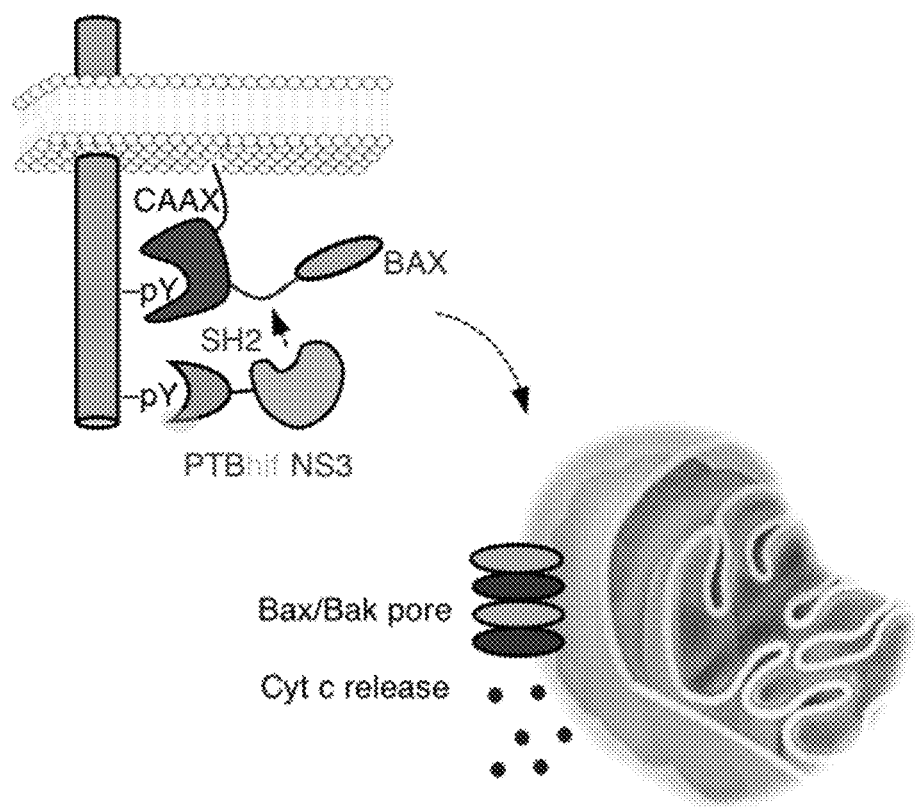
FIGS. 5A-5C show that RASER can be programmed to induce apoptosis in cancer cells.
Figure 5B:
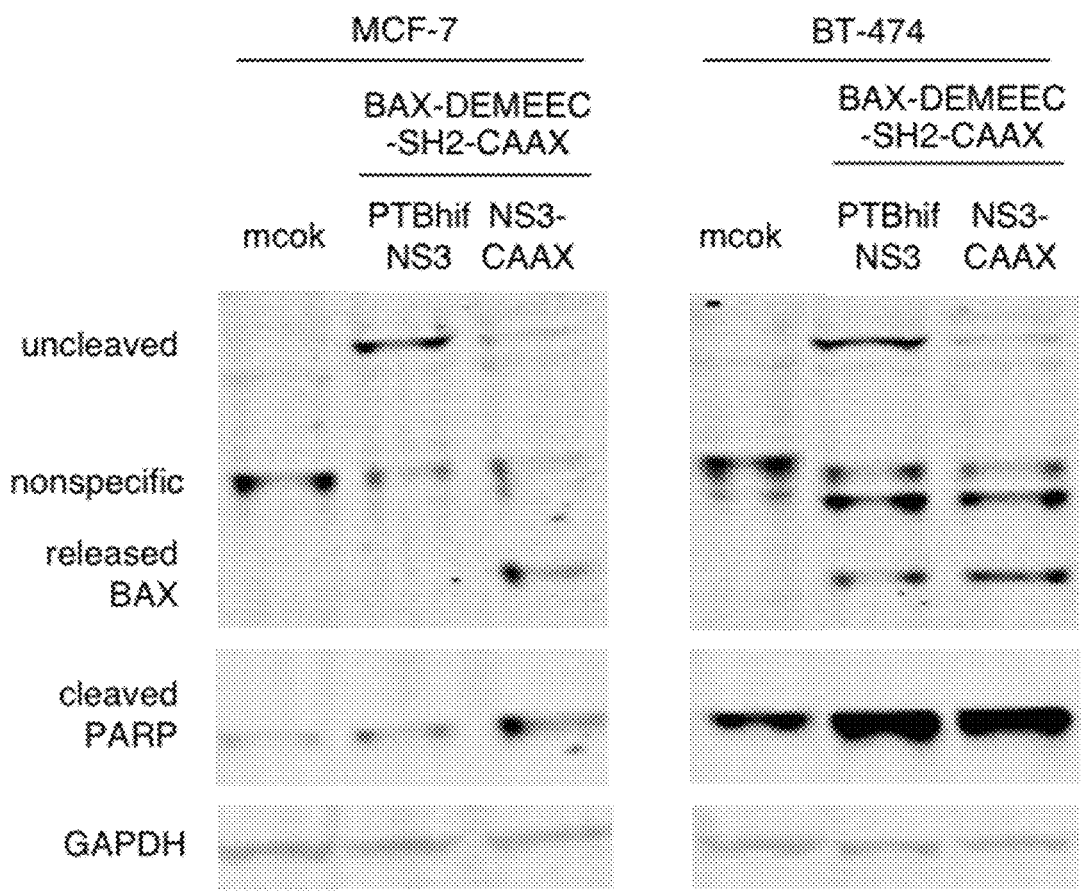
Figure 5C:
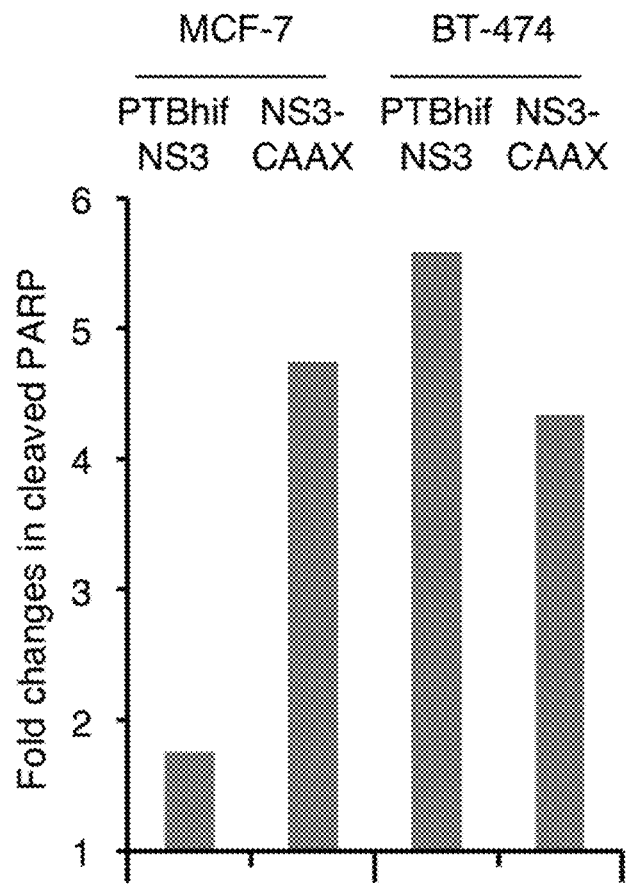

Now that we have built a synthetic signaling system that has the unique ability of integrating signal from ErbB over time and thus specifically detecting oncogenic ErbB, we explored different options for programmable cargos. Cargos causing cell death could be therapeutically useful to release in ErbB-hyperactive cancer cells. To test this, we created an ErbB-RASER system in which the cargo protein is Bax, a protein that induces cytochrome release from mitochondria to initiate apoptosis (FIG. 5A). We then tested this ErbB-RASER-Bax system in BT-474 cells which overexpress ErbB receptors and MCF-7 cells with normal ErbB levels (FIG. 5B). We found that ErbB-RASER-Bax was indeed able to induce apoptosis in BT-474 cells in an ErbB signaling-dependent manner, with levels of the apoptotic marker PARP reaching similar levels as with direct membrane expression of protease (FIGS. 5B and 5C). In contrast, in MCF-7 cells, PARP levels remain near untransfected controls (FIGS. 5B and 5C). These results establish that the RASER system can be designed to trigger a therapeutic function in response to an oncogenic state.

Figure 6A:
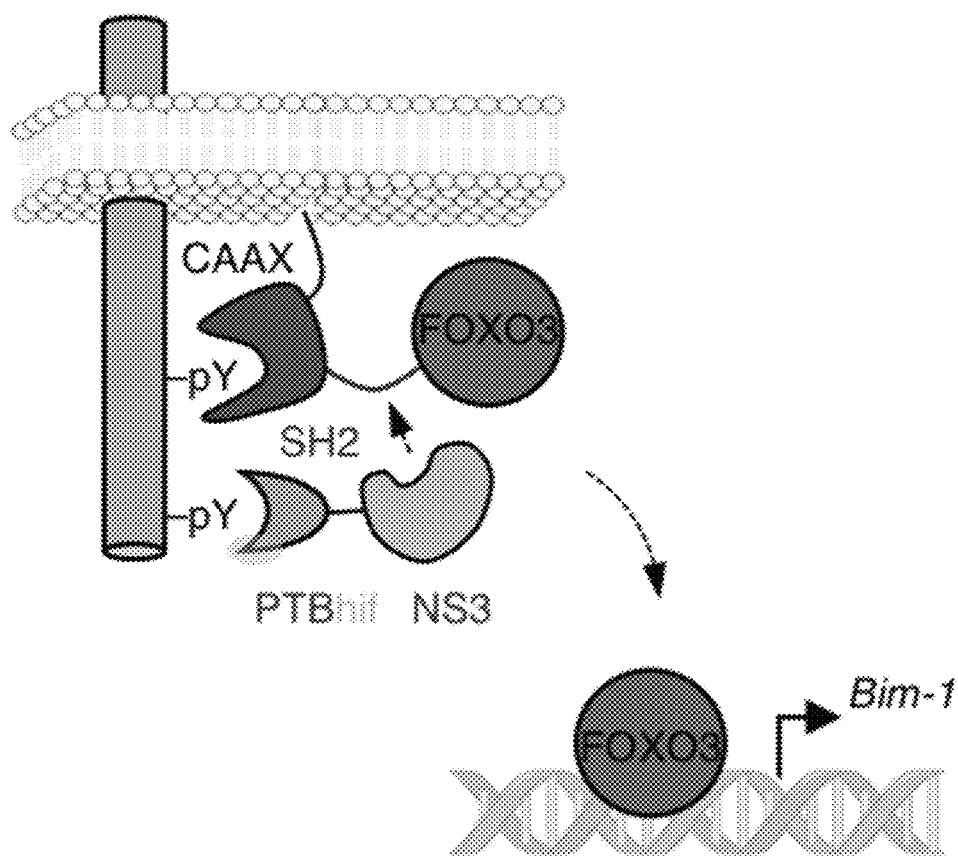
FIGS. 6A-6C show that RASER can be programmed to induce transcription of endogenous genes in cancer cells.
Figure 6B:
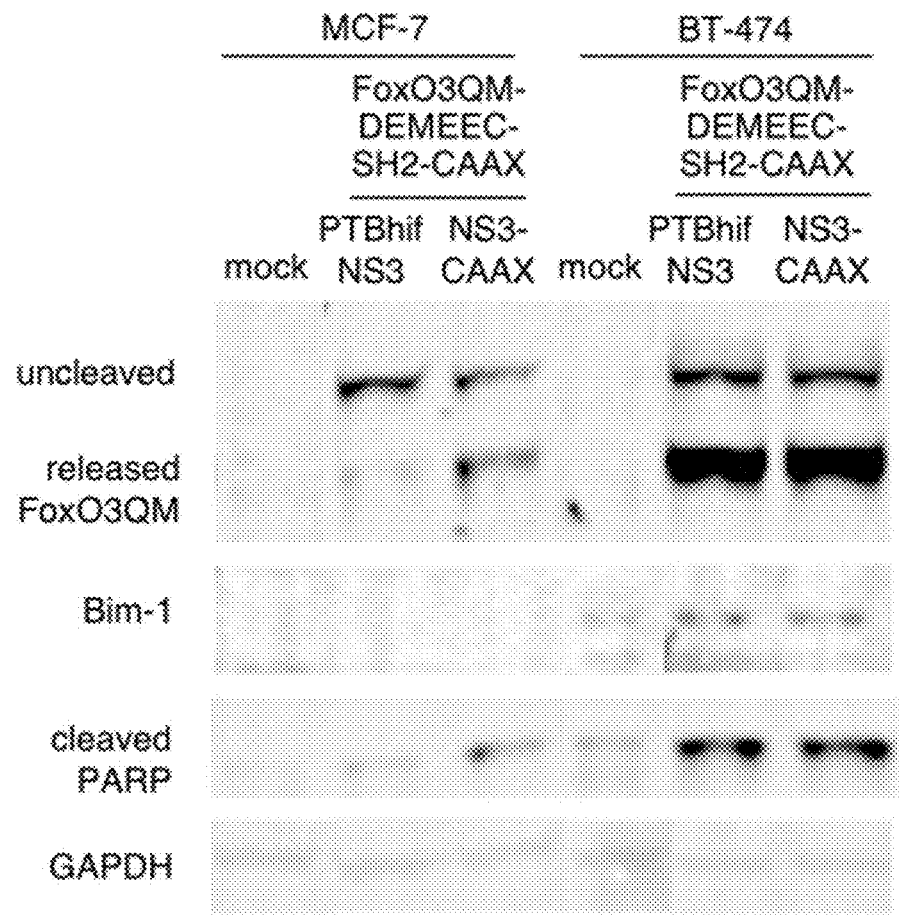
Figure 6C:
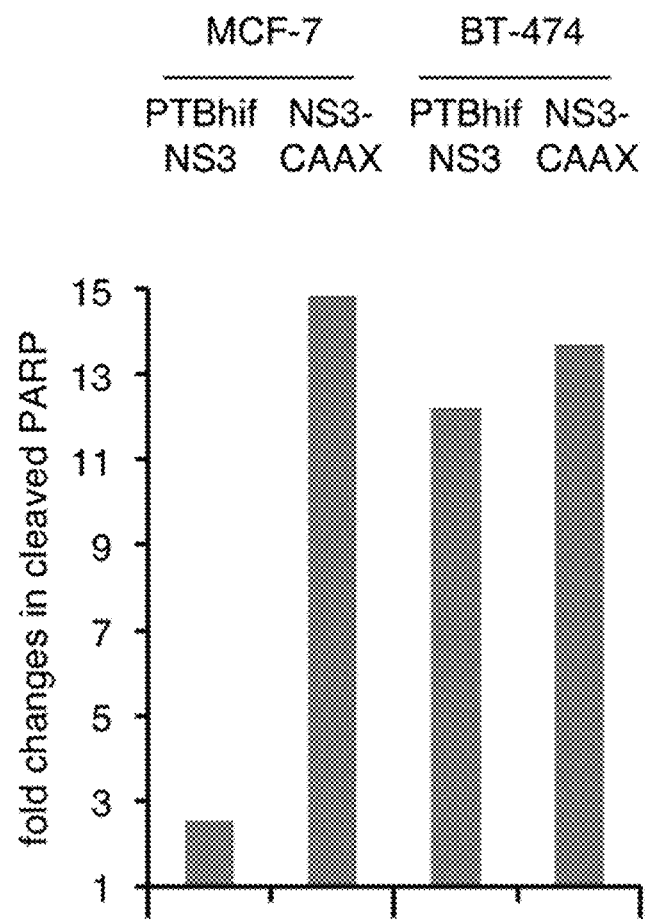

Another general class of useful cargos for ErbB-RASER may be transcription factors that can activate endogenous genes in cancer cells for therapeutic effect. We thus also created an ErbB-RASER system in which the cargo protein is a constitutively active FOXO3, a transcription factor that activates pro-apoptotic genes (FIG. 6A). We also tested this ErbB-RASER-FOXO3 system in BT-474 cells which overexpress ErbB receptors and MCF-7 cells with normal ErbB levels (FIG. 6B). We found that ErbB-RASER-FOXO3 was also able to induce apoptosis in BT-474 cells in an ErbB signaling-dependent manner, with levels of the apoptotic marker PARP reaching similar levels as with direct membrane expression of protease (FIGS. 6B and 6C). In contrast, in MCF-7 cells, PARP levels remains near untransfected controls (FIGS. 6B and 6C). These results establish that the RASER system can be designed to trigger a therapeutic function in response to an oncogenic state via activation of endogenous genes.

Figure 7A:
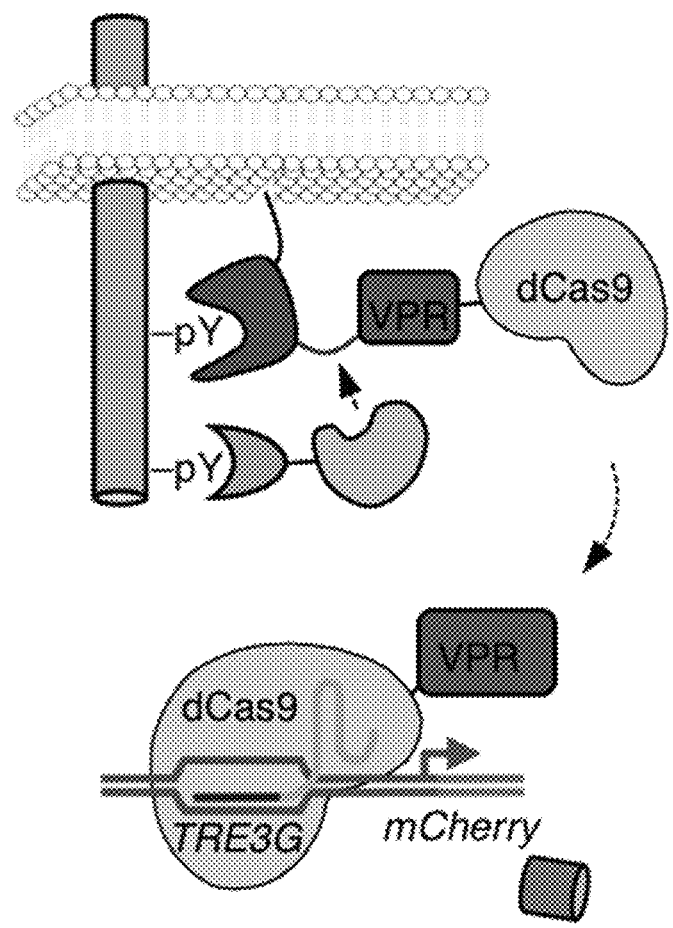
FIGS. 7A-7C show that RASER can be programmed to induce transcription of target genes via dCas9.
Figure 7B:
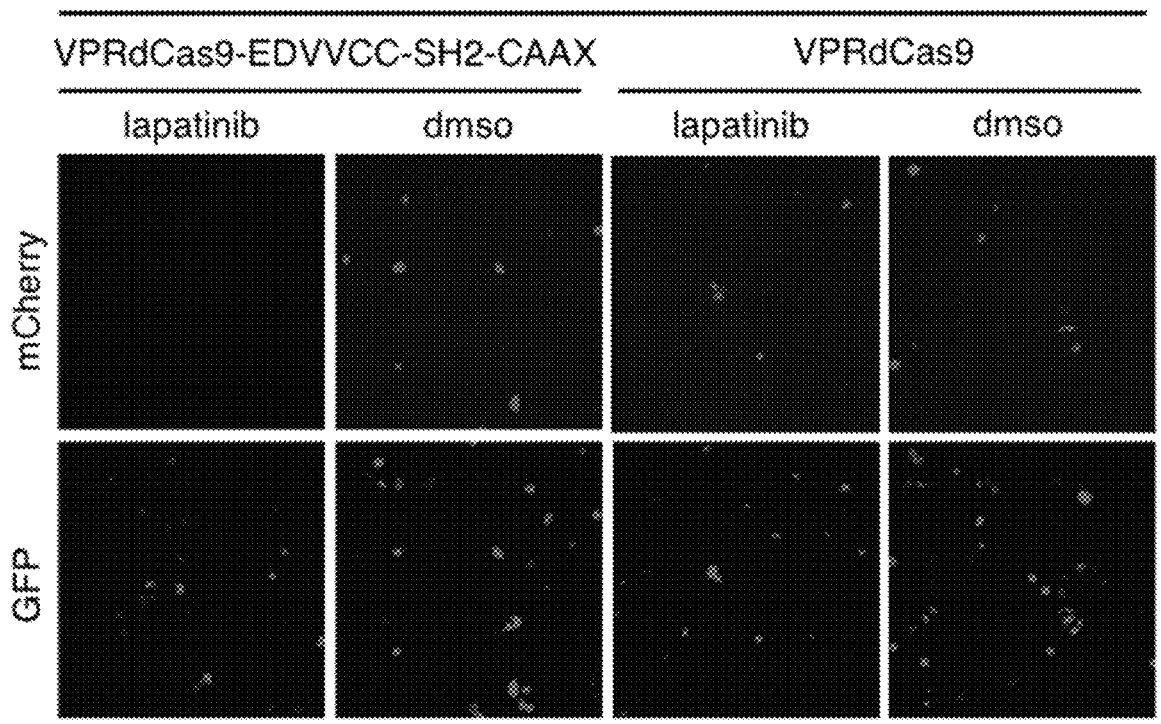
Figure 7C:
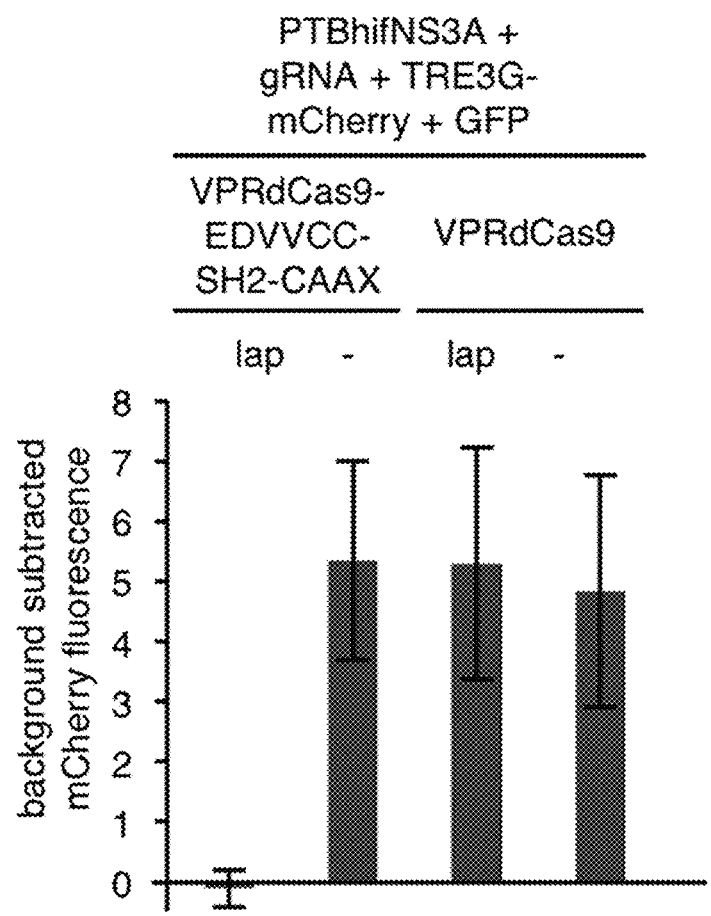
Figure 7D:
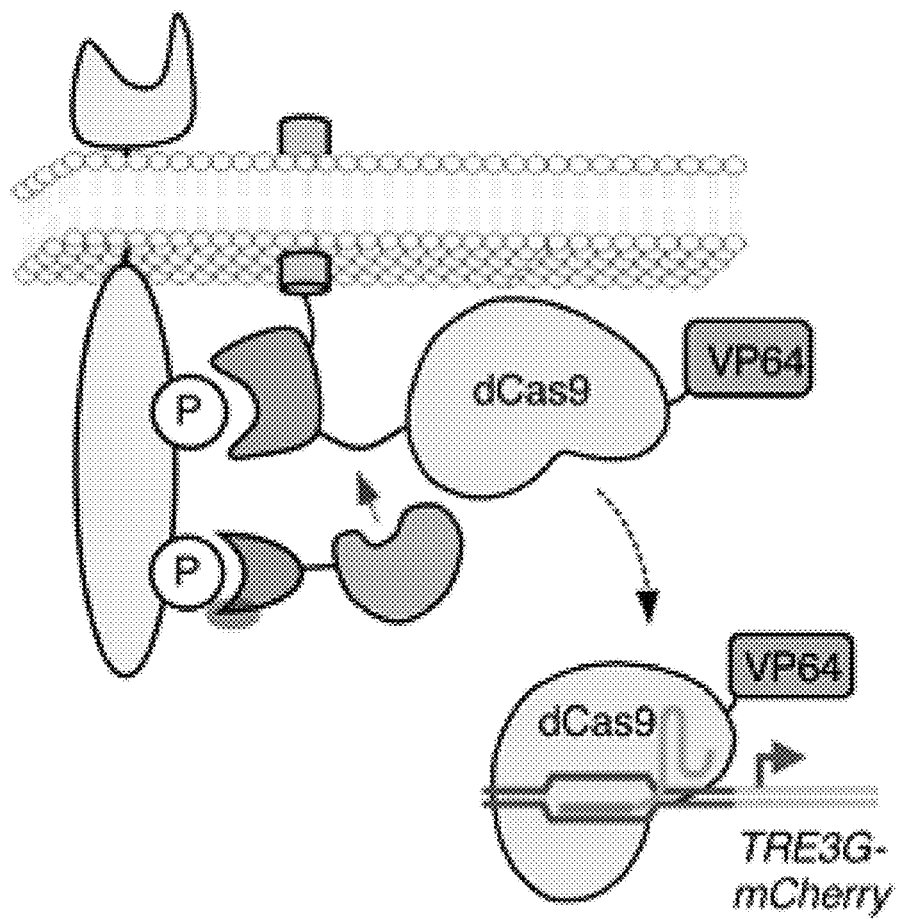
FIGS. 7D-7I show that RASER can be programmed to induce transcription of endogenous genes via dCas9.
Figure 7E:
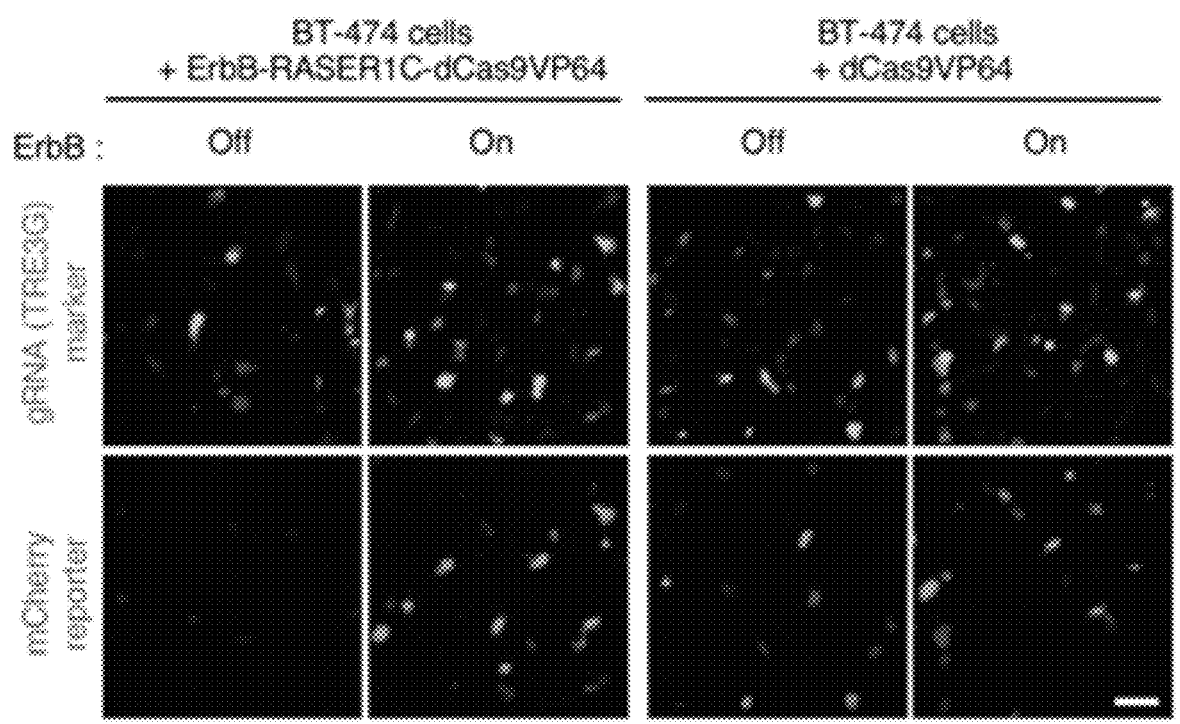

Finally, we explored whether RASER could be used to rewire hyperactive ErbB to the transcriptional activation of essentially any endogenous gene by using a CRISPR/Cas9 protein as the cargo. Catalytically inactive Cas9 (dCas9) fused to the VP64-p65-Rta-dCas9 (VPR) transcriptional activation domain can be targeted by a coexpressed guide RNA (gRNA) to promote transcription of a gene of interest. We generated an ErbB-RASER-VPRdCas9 system to release VPRdCas9 in an ErbB-dependent manner (FIG. 7A). To test ErbB-RASER-VPRdCas9, we expressed in BT474 cells the RASER components, a reporter plasmid that expresses a mCherry gene under the control of a TRE promoter, and a gRNA targeting the TRE promoter. Cells were then left untreated or treated with lapatinib to shut off the ErbB signal. Indeed, we observed that, in the absence of lapatinib, RASER VPR-dCas9 induces mCherry expression as well as the parent VPRdCas9 (FIGS. 7B and 7C). Lapatinib prevents mCherry expression in RASER-transfected cells, but not in cells expressing a positive control VPRdCas9 construct and gRNA, demonstrating the requirement for ErbB signaling (FIGS. 7B and 7C). These results establish that the RASER system can be programmed to induce dCas9-mediated activation of a promoter specified by a coexpressed gRNA.

Discussion

To summarize, we have provided proof of concept for a new approach called RASER in which we construct an artificial signaling pathway to rewire oncogenic signaling states to effector activation. Importantly, this synthetic signaling pathway is compact, comprising only two proteins, and can be programmed to activate a variety of outputs. For example, we have found RASER can be programmed to release BAX to activate an endogenous apoptotic pathway, to release FoxO3 to activate endogenous transcription, and to release VPRdCas9 to activate genes targeted by a gRNA. We believe that this programmability will be broadly useful, as it will allow ErbB hyperactivity to be rewired to a variety of therapeutically useful outputs, such as induction of apoptosis or activation of immunostimulatory genes.

As a therapeutic approach, RASER may be advantageous over conventional therapies in that it is unlikely to elicit drug resistant mutations. Conventional therapies such as RTK inhibitors and monoclonal antibodies inhibit cell proliferation via inhibiting kinase activity or binding to the ectodomain of the receptor providing a strong selective pressure for target mutations that mitigate inhibitor binding and preserve receptor function. In contrast, RASER is activated by the same signals used by the cell to drive tumor growth and survival. Thus, further increases in ErbB activity should only activate RASER further, whereas mutations that decrease RASER activation, such as at phosphoacceptor sites in ErbB, would result in loss of oncogenic drive as well.

Example 2

RASER Systems with C-Terminal Cargo Proteins

Figure 9A:
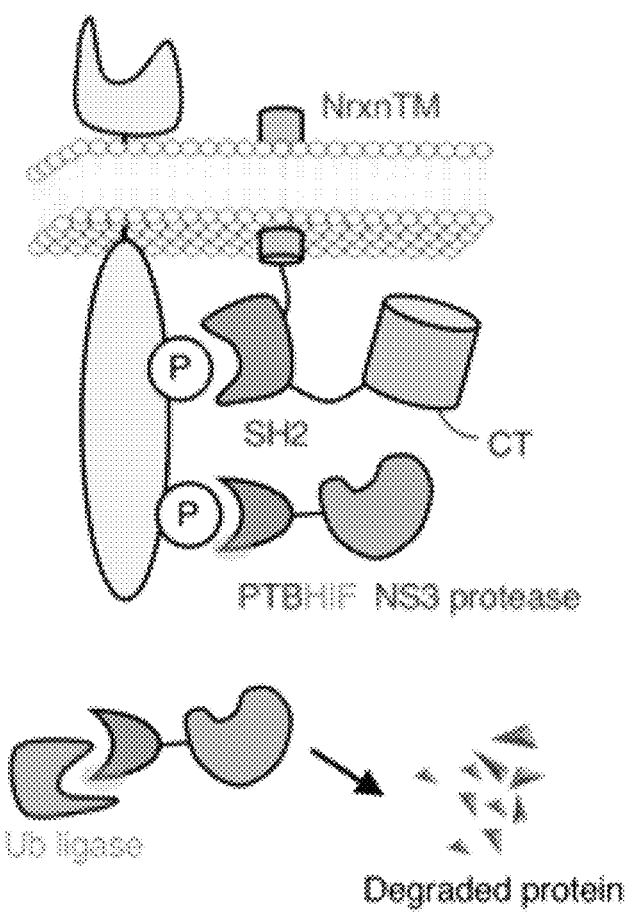
FIGS. 9A-9D show RASER with C-terminally fused cargoes.
Figure 9B:
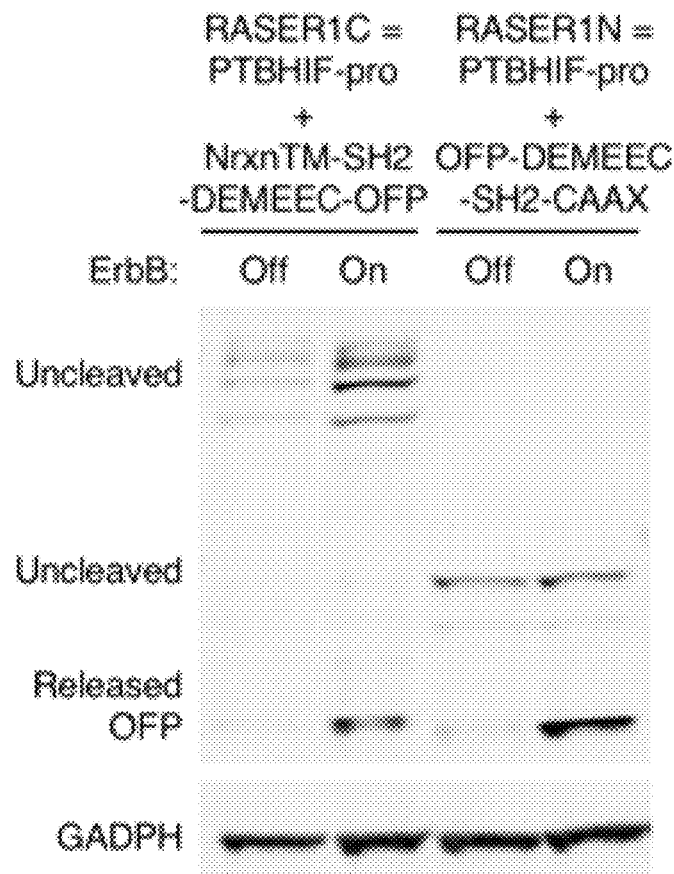
Figure 9C:
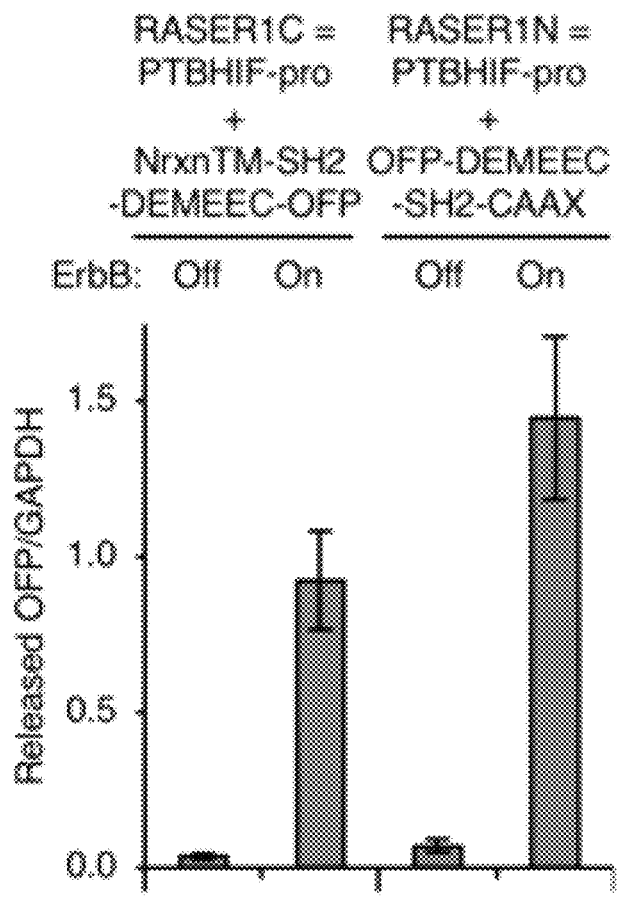
Figure 9D:
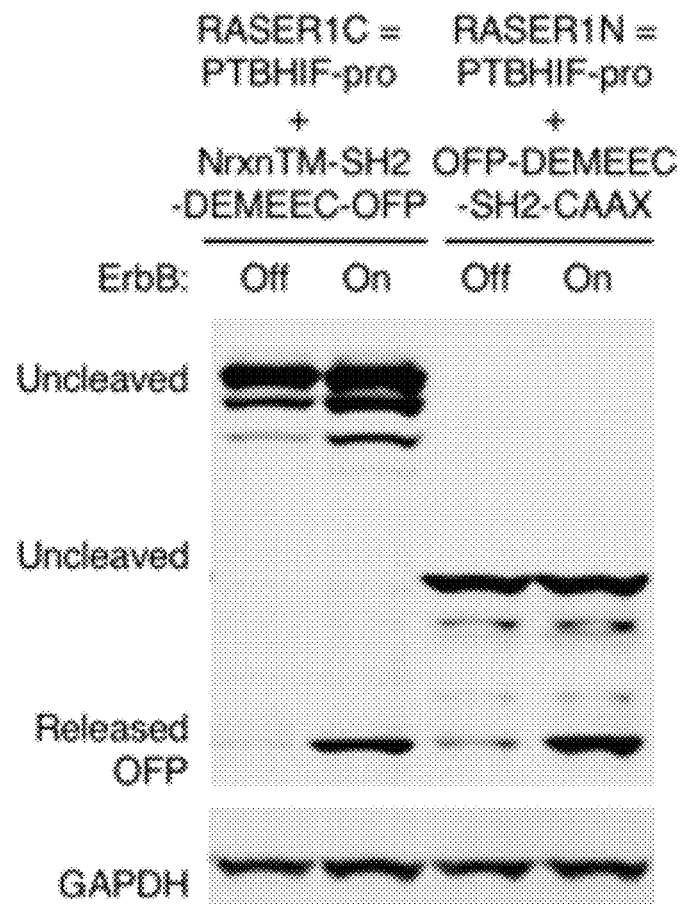

One of the desirable features of the RASER design is its potential versatility in outputs, as various functional cargos can be incorporated into the substrate fusion protein. To further enhance versatility, we constructed a RASER variant to release cargo proteins from the C-terminus of the substrate protein. We tested a substrate protein composed of a signal peptide, the neurexin transmembrane segment (Wang et al. (2017) Nat. Biotechnol. 35:864), the VAV1 SH2 domain, an HCV protease cleavage site, and the OFP cargo domain, and found it to respond as well as the OFP-site-SH2-CAAX substrate fusion in ErbB2-overexpressing BT-474 cells (FIGS. 9A-9C). We named RASER systems using this substrate protein arrangement as RASER1C. We named the RASER systems using the original substrate protein arrangement with cargo at the N-terminus as RASER1N. We also confirmed both ErbB-RASER1N and ErbB-RASER1C released cargo in response to coexpression of EGFRvIII, a constitutively active ErbB1 mutant, in MCF-7 cells, which otherwise exhibit normal levels of ErbB activity (FIG. 9D).

We asked whether we could use C-terminally fused dCas9VP64 as a cargo. We constructed ErbB-RASER1C-dCas9VP64 to link ErbB hyperactivity to the transcription of endogenous genes. An endogenous gene whose activation in a cancer cell could be therapeutically useful is CSF2, encoding GM-CSF. GM-CSF induces antigen-presenting dendritic cells to present antigens released from tumor cells, in turn activating cytotoxic T lymphocytes recognizing those antigens (Hamilton (2008) Nat. Rev. Immunol. 8:533). However, in clinical trials, systemic GM-CSF injections have shown limited anti-tumor efficacy while causing toxicity from off-target immune reactions (Arellano et al. (2008) Biologics 2:13). Inducing GM-CSF expression specifically in tumor cells in situ may elicit more effective immune responses than systemic GM-CSF and indeed is an essential mechanism of action for an oncolytic virus recently approved for clinical use (Kohlhapp et al. (2016) Clin. Cancer Res. 22:1048).

Figure 7F:
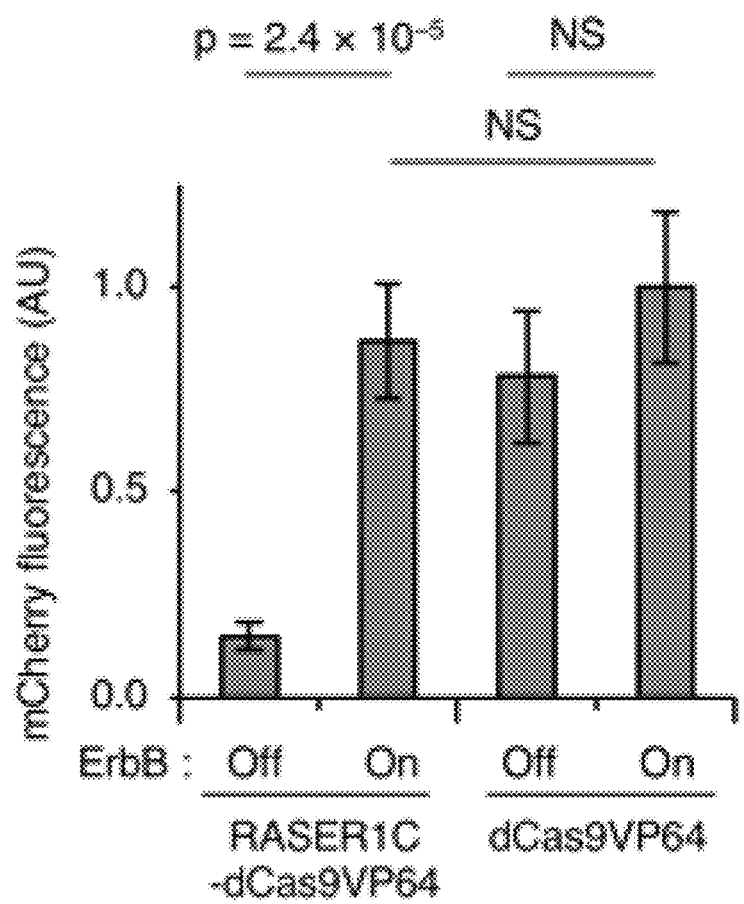
Figure 7G:
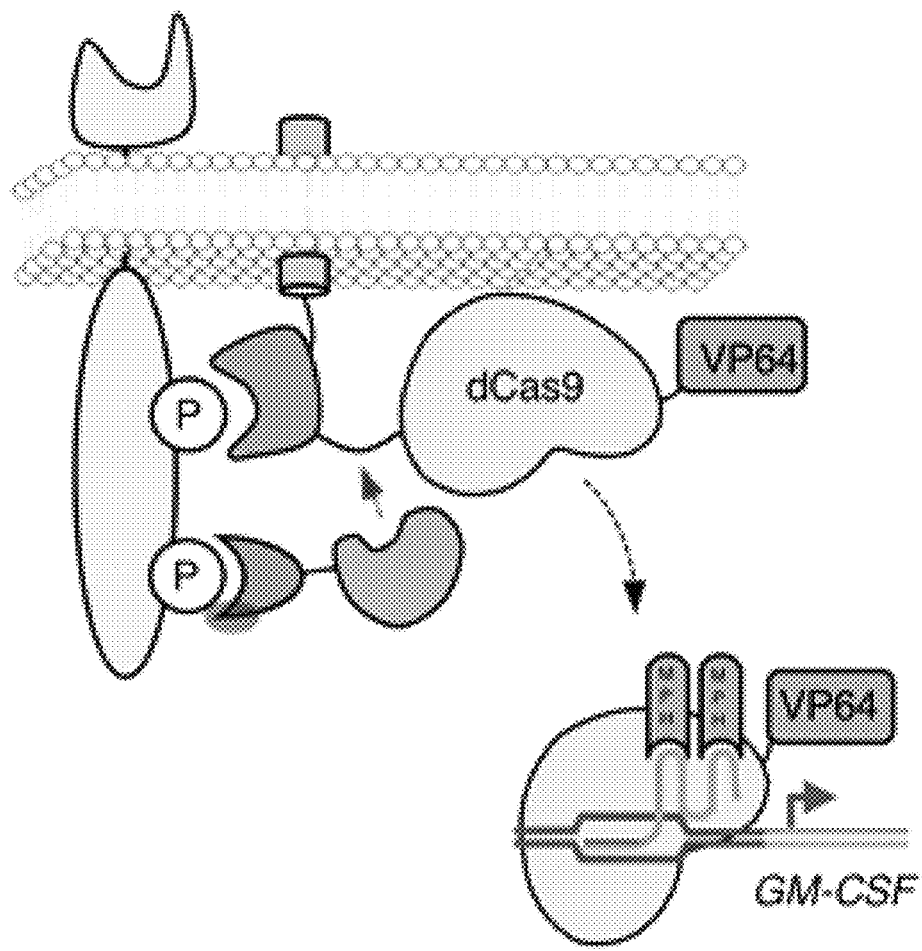
Figure 7H:
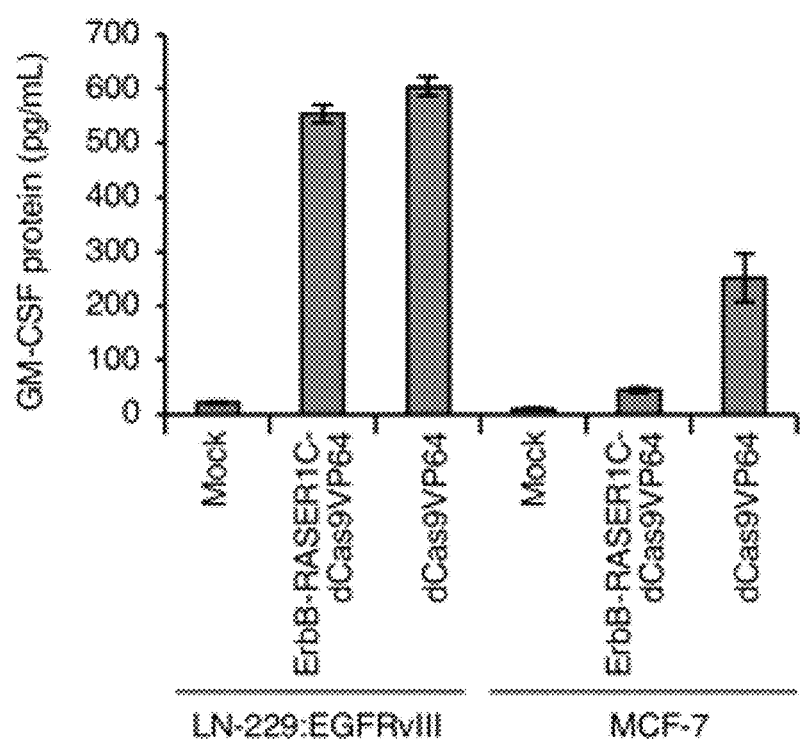
Figure 7I:
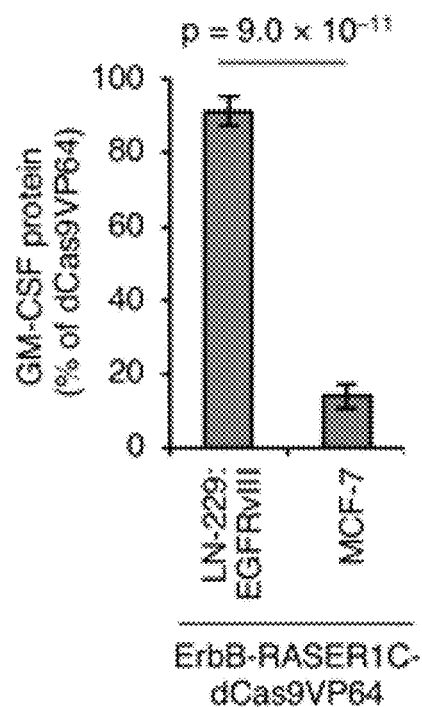
Figure 16A:
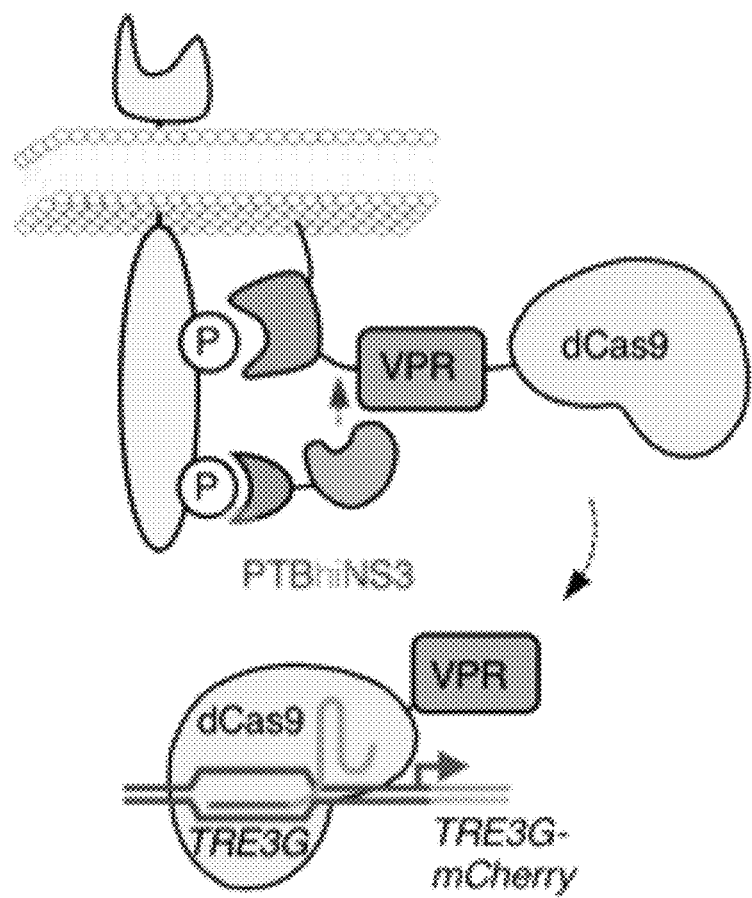
FIGS. 16A-16D show programming of RASER to rewire constitutive ErbB signaling to transcription.
Figure 16B:
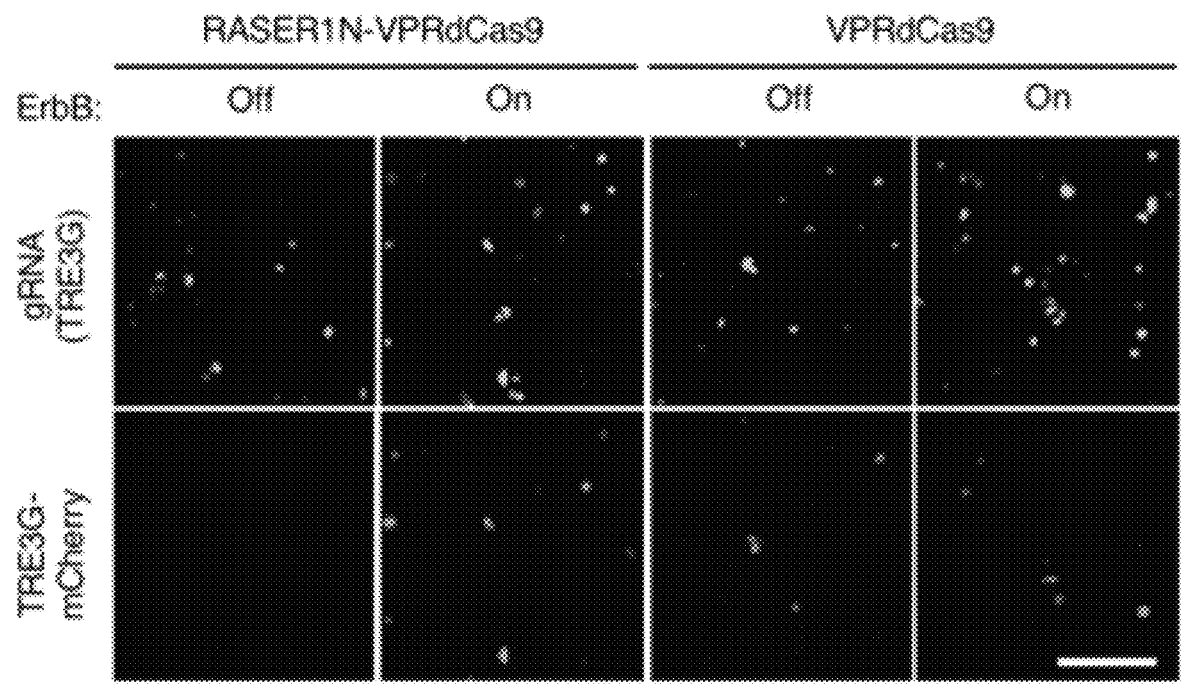
Figure 16C:
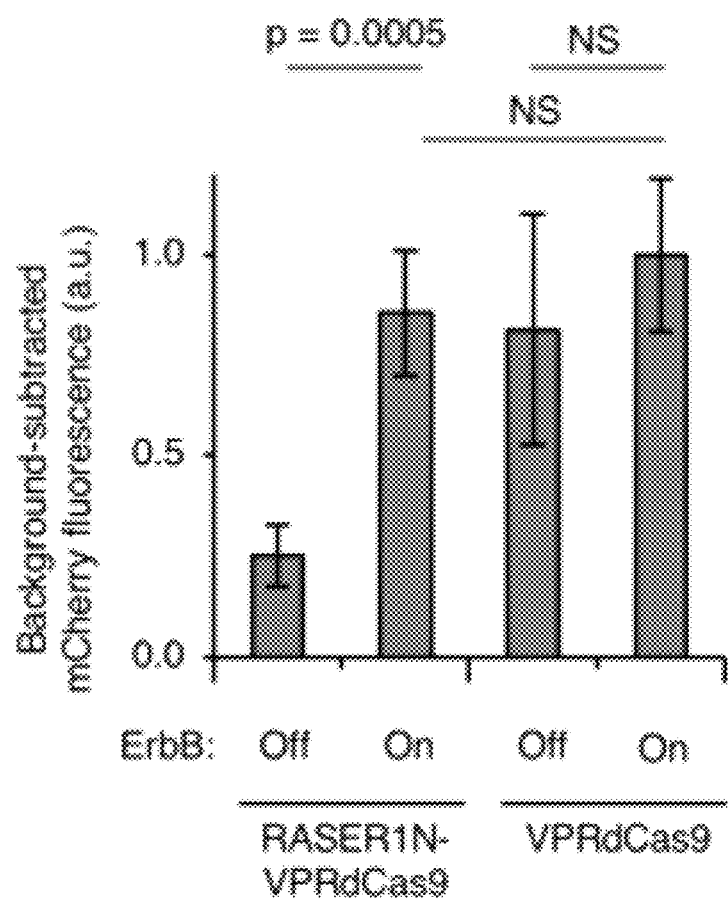
Figure 16D:
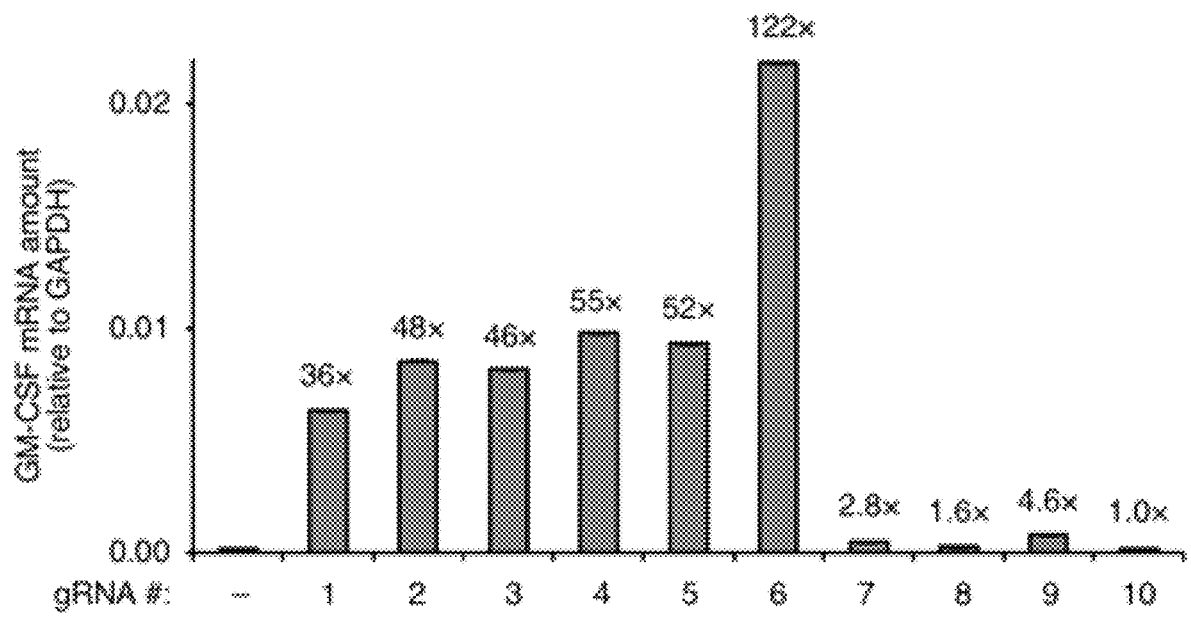

To enable targeted activation of CSF2 transcription in ErbB-driven cancer cells by RASER (FIG. 7G), we identified a gRNA that could mediate effective transcriptional activation of CSF2 (FIG. 16D). We then introduced the combination of ErbB-RASERC1-dCas9VP64, SAM transactivation components (Konermann et al. (2015) Nature 517:583), and the optimal gRNA into cells with either ErbB hyperactivity or normal ErbB activity, and assayed for GM-CSF protein in the cell media. We found that GM-CSF production was efficiently upregulated in cells with hyperactive ErbB, reaching 87% of that of an untethered dCas9VP64 control, but remained low in cells with normal ErbB activity (FIGS. 7H, 7I). These results demonstrate that RASER can indeed rewire oncogenic ErbB signaling to activation of endogenous genes of choice using dCas9 proteins.

Figure 10A:
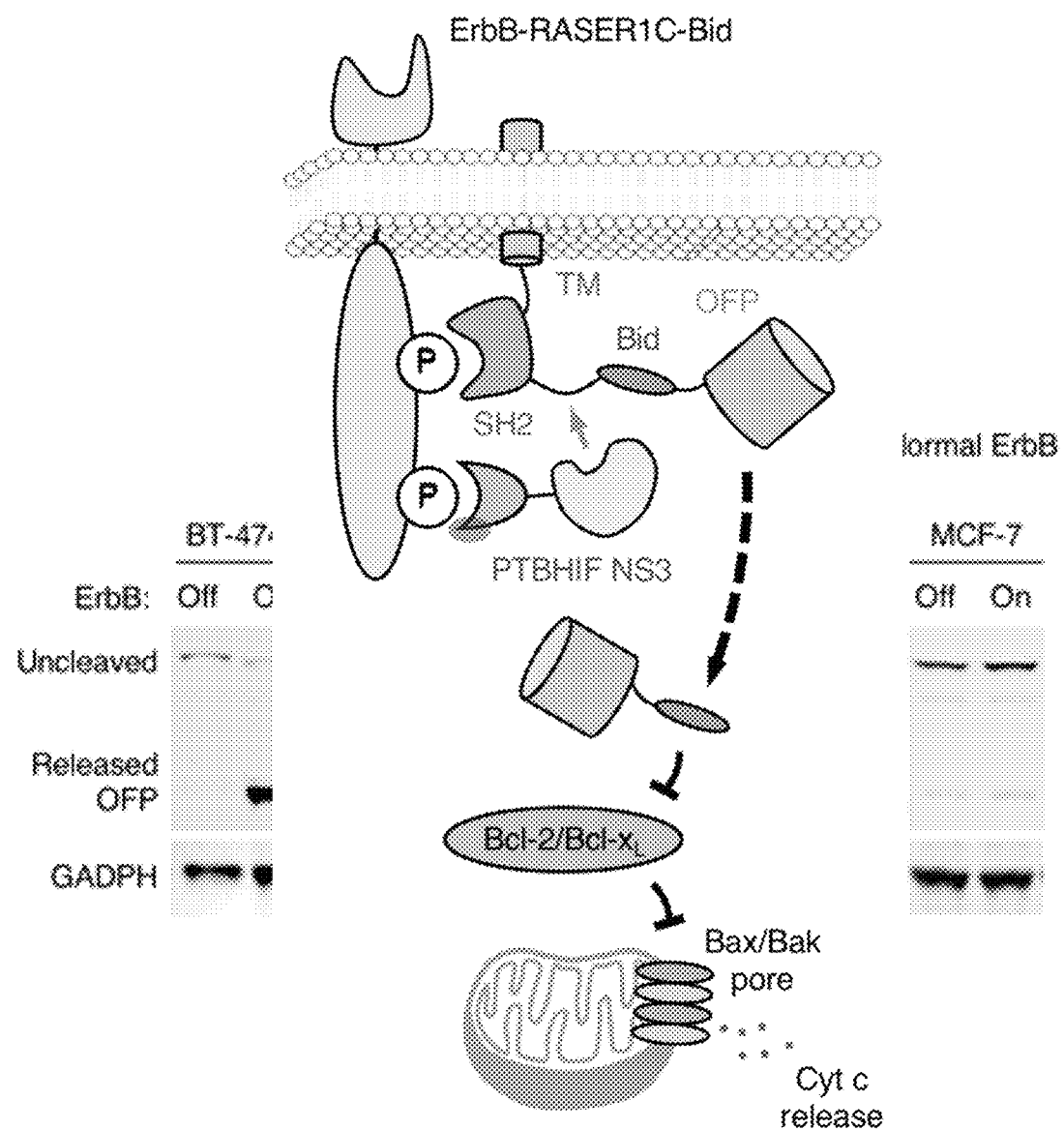
FIGS. 10A-10H show that RASER with C-terminally fused cargoes can be programmed to induce apoptosis selectively in ErbB-driven cancer cells.
Figure 10B:
Figure 10C:
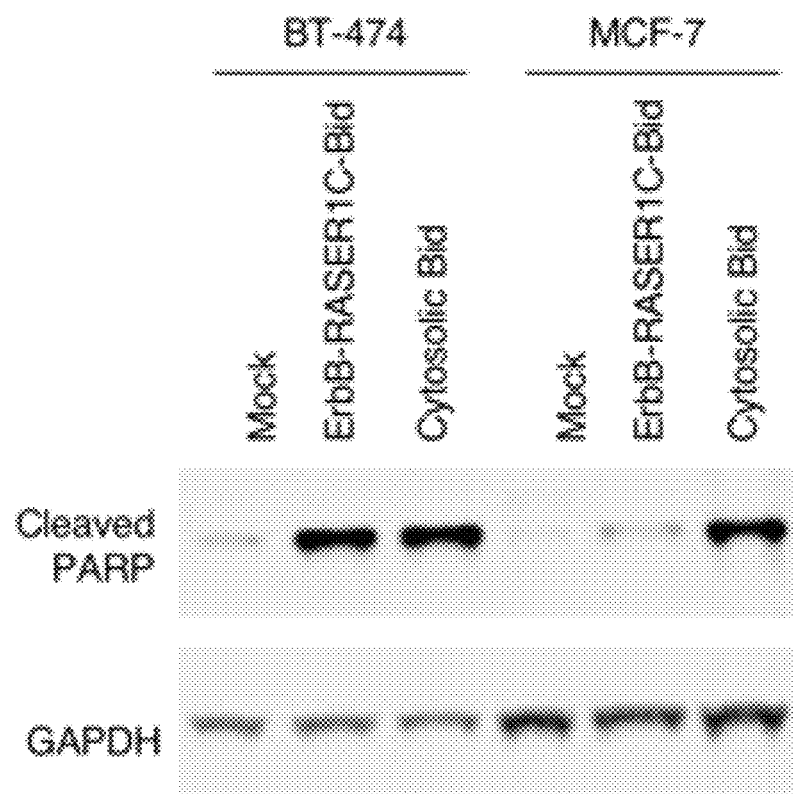
Figure 10D:
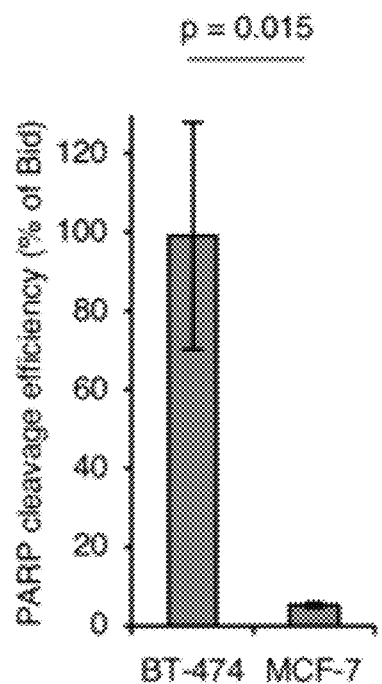
Figure 15A:
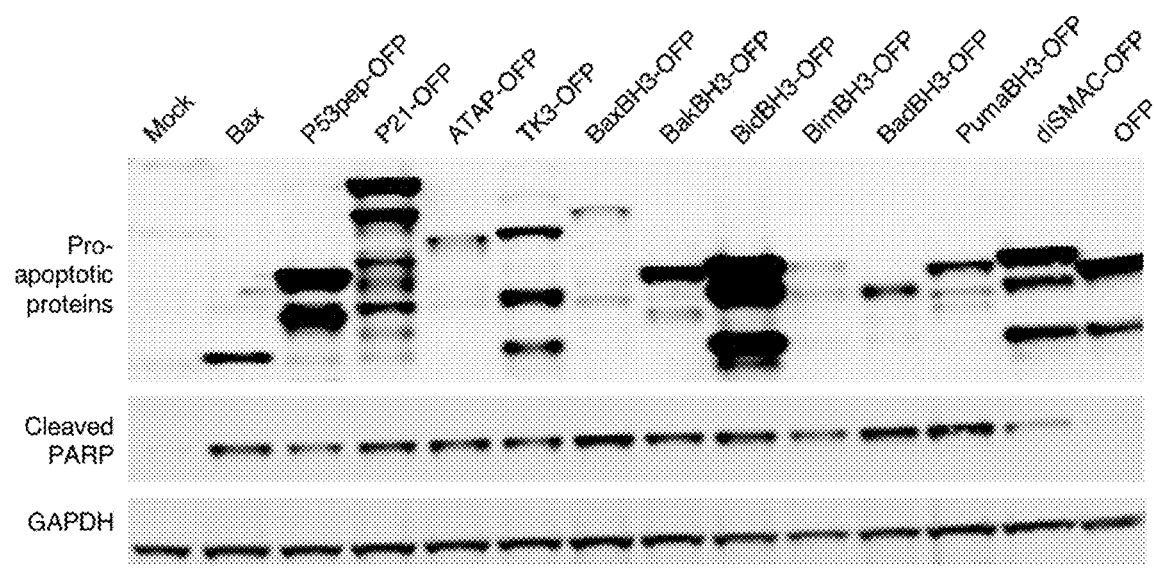
FIGS. 15A and 15B show programming of RASER outputs to rewire constitutive ErbB to apoptosis.
Figure 15B:
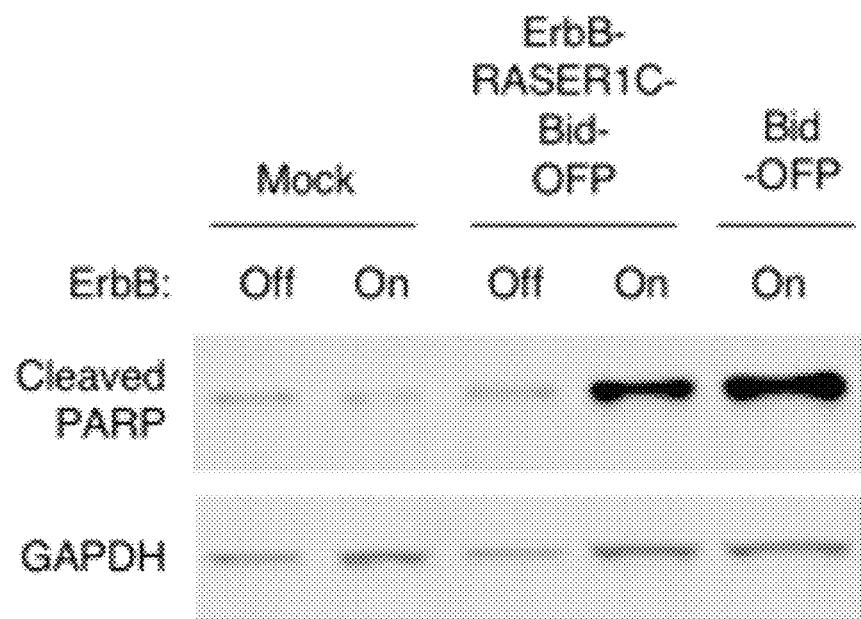

We found various BH3 domains fused to OFP were potent apoptosis inducers (FIG. 15A). We then performed additional experiments using the BID BH3 domain fused to OFP (hereafter referred to as BID-OFP) as cargo to rewire oncogenic ErbB signaling to apoptosis (FIG. 10A). We created a single transcriptional unit co-expressing both substrate and protease components of ErbB-RASER to release BID-OFP, named ErbB-RASER1C-BID (FIG. 10B). Indeed, we found that in ErbB2-overexpressing BT-474 breast cancer cells, transfection of ErbB-RASER1C-BID induced PARP cleavage, a marker of apoptosis, to 99% of the levels induced by BID alone (FIGS. 10C, 10D). This effect was dependent on ErbB activity, as it was blocked by lapatinib (FIG. 15B). If RASER were to be clinically useful, then ErbB-RASER1C-BID should not kill cells without hyperactive ErbB. Indeed, expression of ErbB-RASER1C-BID induced apoptosis in ErbB-normal MCF-7 cells with only 5% efficiency compared to BID alone (FIGS. 10C, 10D).

Figure 10E:
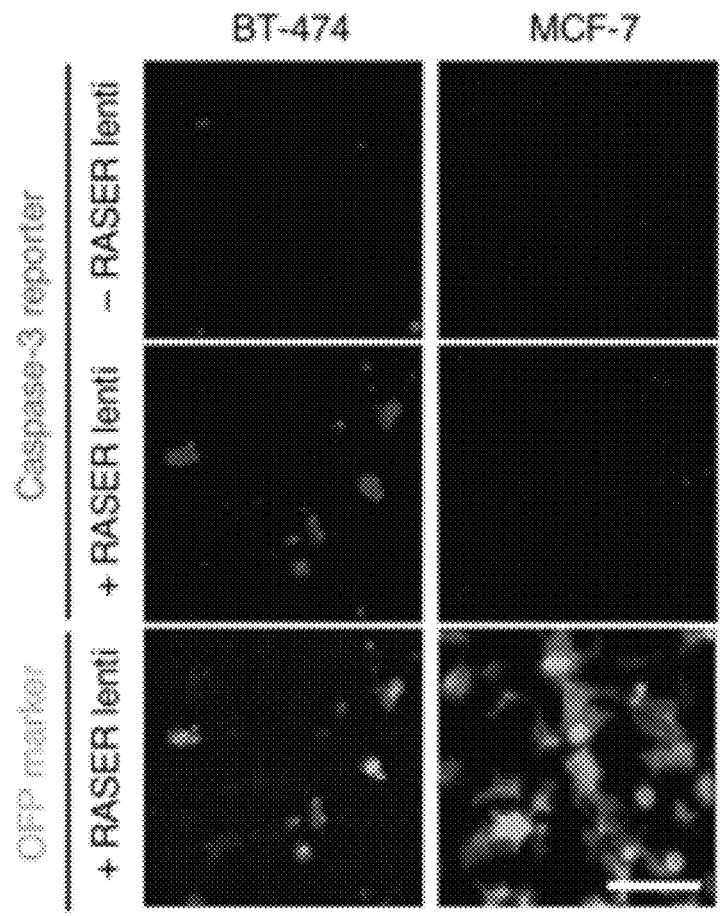
Figure 10F:
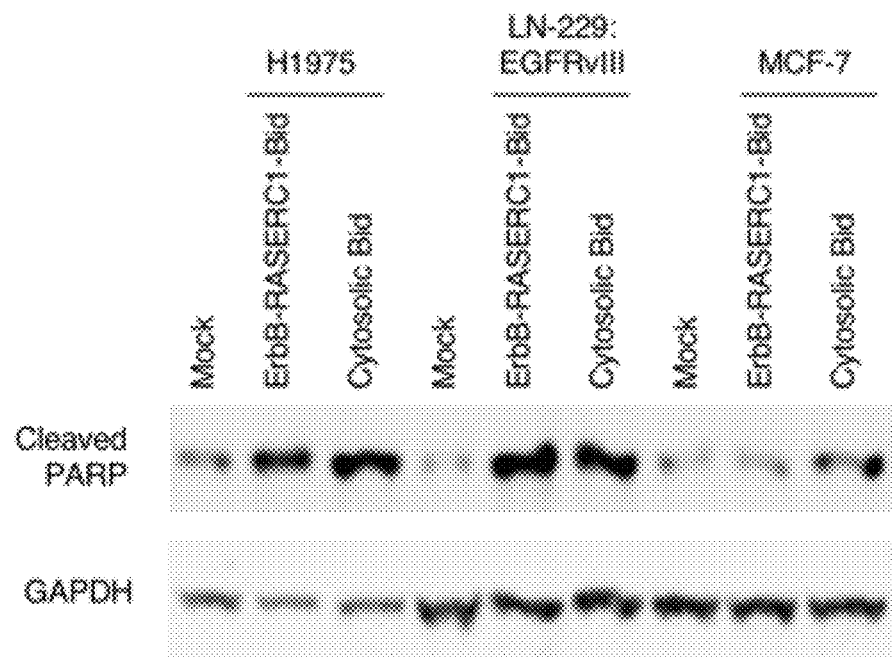
Figure 10G:
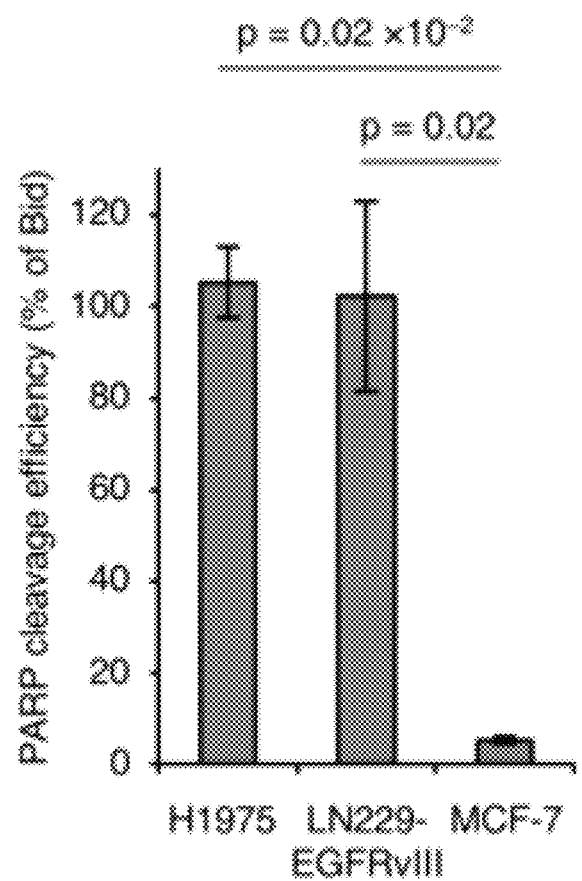
Figure 10H:
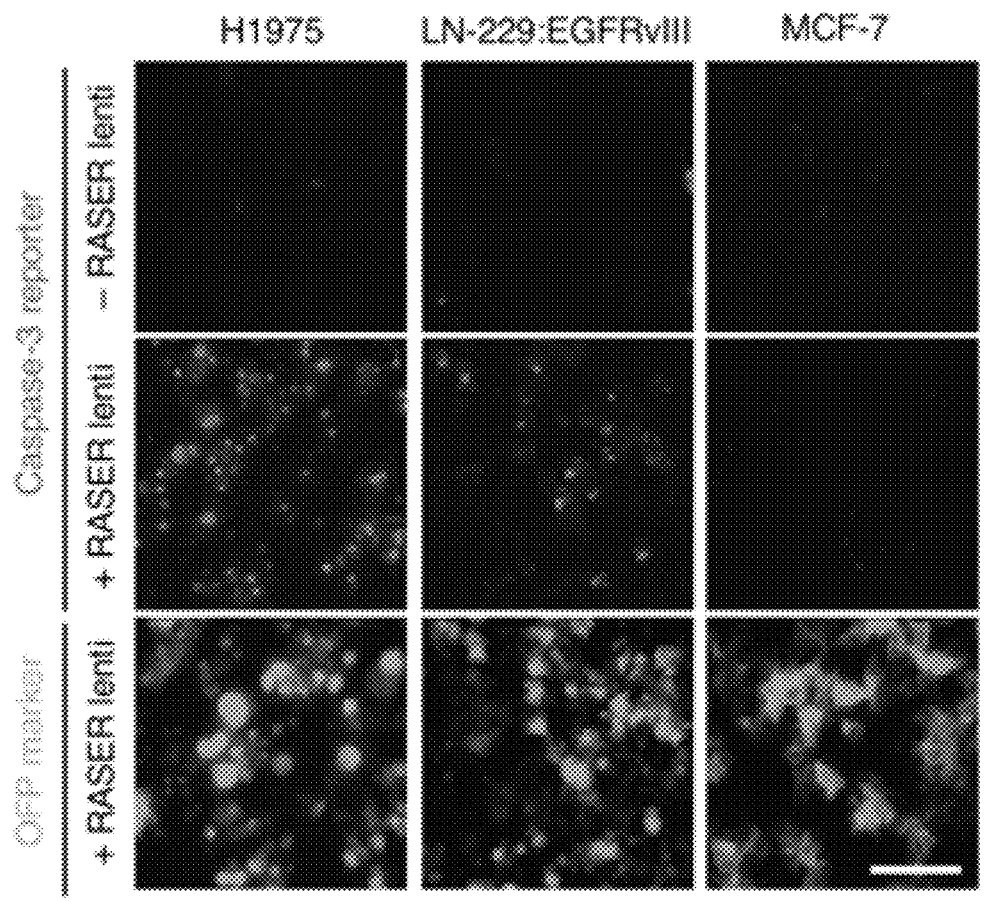

As RASER would need to be delivered by viruses for in vivo applications, we also tested RASER performance under viral expression conditions. Lentiviral transduction of ErbB-RASER1C-BID efficiently induced apoptosis in BT-474 cells but not MCF-7 cells, as visualized by a caspase-activated fluorescent dye (FIG. 10E). Indeed, apoptosis occurred in nearly all transduced BT-474 cells, but no transduced MCF-7 cells. ErbB-RASER1C-BID also caused apoptosis in the ErbB1-dependent lines H1975 and LN-229: EGFRvIII (FIGS. 10F-10H). These results demonstrate that RASER can be programmed to directly induce apoptosis in response to constitutive ErbB activity, and that virally delivered RASER can selectively kill ErbB-driven cancer cells.

Example 3

Efficacy and Specificity of the RASER-Induced Apoptosis

Figure 11A:
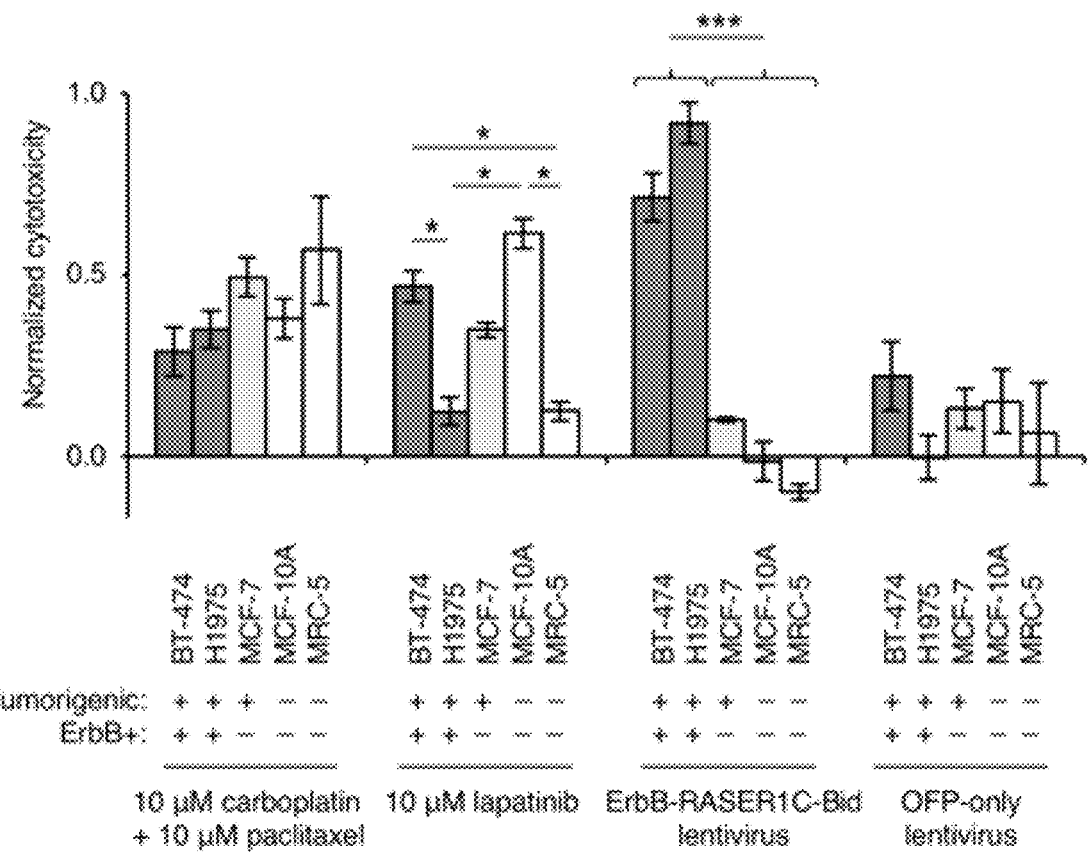
Figure 11B:
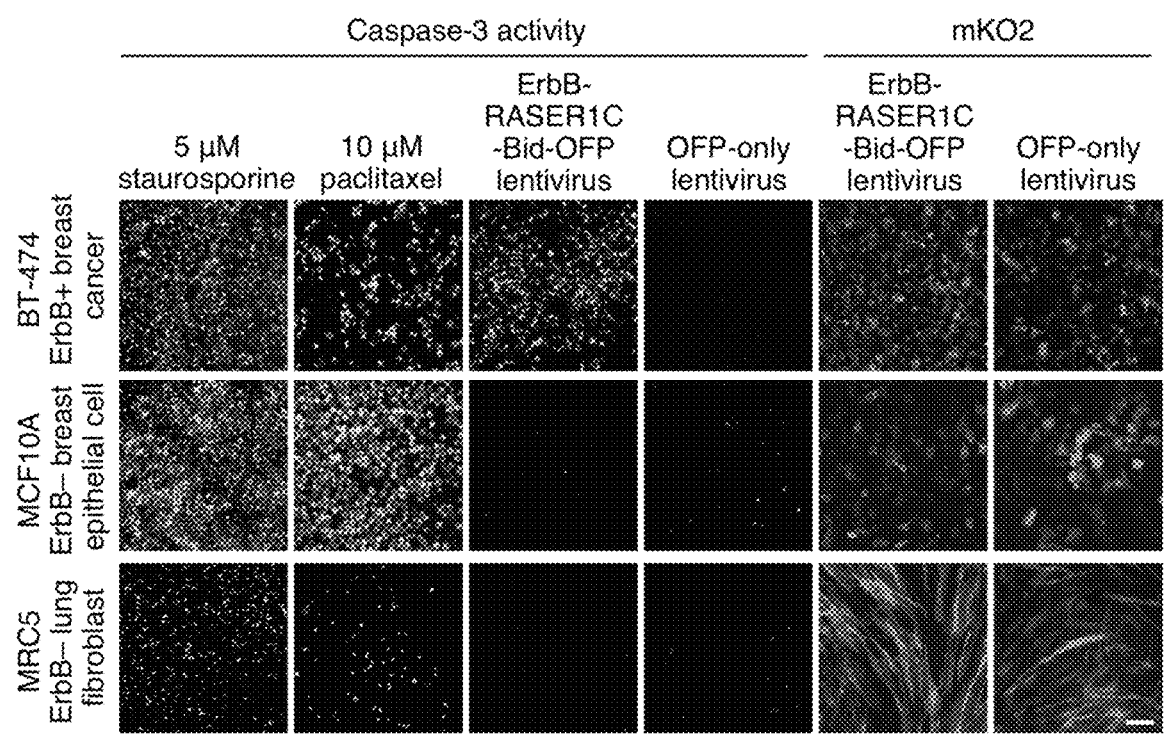

To explore the potential utility of RASER for cancer treatment, we compared it to standards of care for efficacy and specificity in killing cancer cells. Two ErbB-hyperactive cancer lines (BT-474 breast cancer and H1975 lung cancer), an ErbB-negative cancer line (MCF-7 breast cancer), and two non-cancerous cell lines (MCF-10A breast epithelium and MRC5 lung fibroblast) were each treated with carboplatin and paclitaxel combination chemotherapy, targeted ErbB inhibitor lapatinib, or a lentivirus expressing ErbB-RASER1C-Bid. The first two treatments are first-line standards of care for metastatic breast and lung cancer, with lapatinib reserved for ErbB-positive cases (Alsharedi et al. (2016) Med. Oncol. 33:27, Boyd et al. (2018) Oncology (Williston Park) 32:418, Socinski (2014) Curr. Oncol. 21:e691, Pimenta et al. (2016) N. Engl. J. Med. 374:2602). We found that carboplatin and paclitaxel killed cells non-selectively, regardless of tumorigenicity or ErbB status (FIG. 11A). Lapatinib cytotoxicity varied by cell line, but did not consistently correlate with ErbB status (FIG. 11A). In contrast, lentivirus-mediated transduction of ErbB-RASER1C-BID induced high rates of cell death in the two ErbB-hyperactive tumor cell lines while having negligible effects on any of the ErbB-normal cells, as desired (FIG. 11A). Imaging experiments confirmed that RASER exhibited superior selectivity and higher cytotoxicity in ErbB-hyperactive cancer cells than paclitaxel (FIG. 11B). Thus, RASER demonstrated greater specificity and efficacy compared to current clinical treatments for ErbB-positive cancers.

Figure 17A:
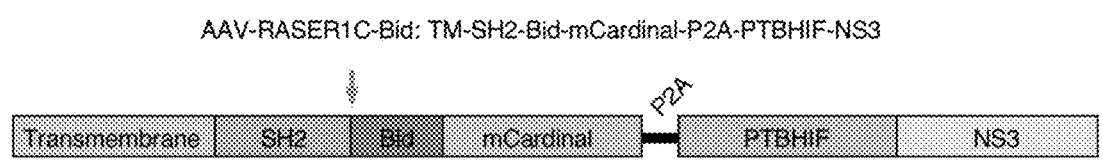
FIGS. 17A-17C show that rAAV-RASER1C-BID releases the cargo mCardinal-BID in an ErbB-dependent manner.
Figure 17B:
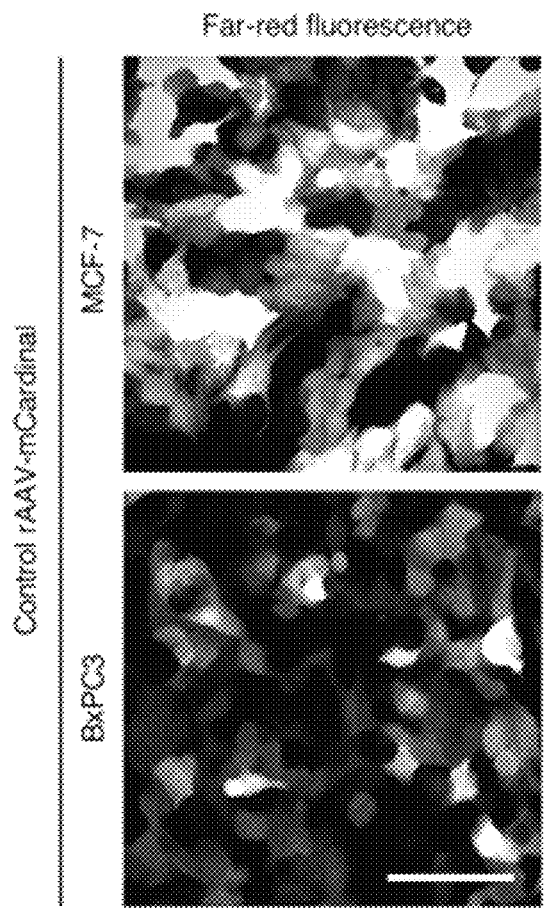
Figure 17C:
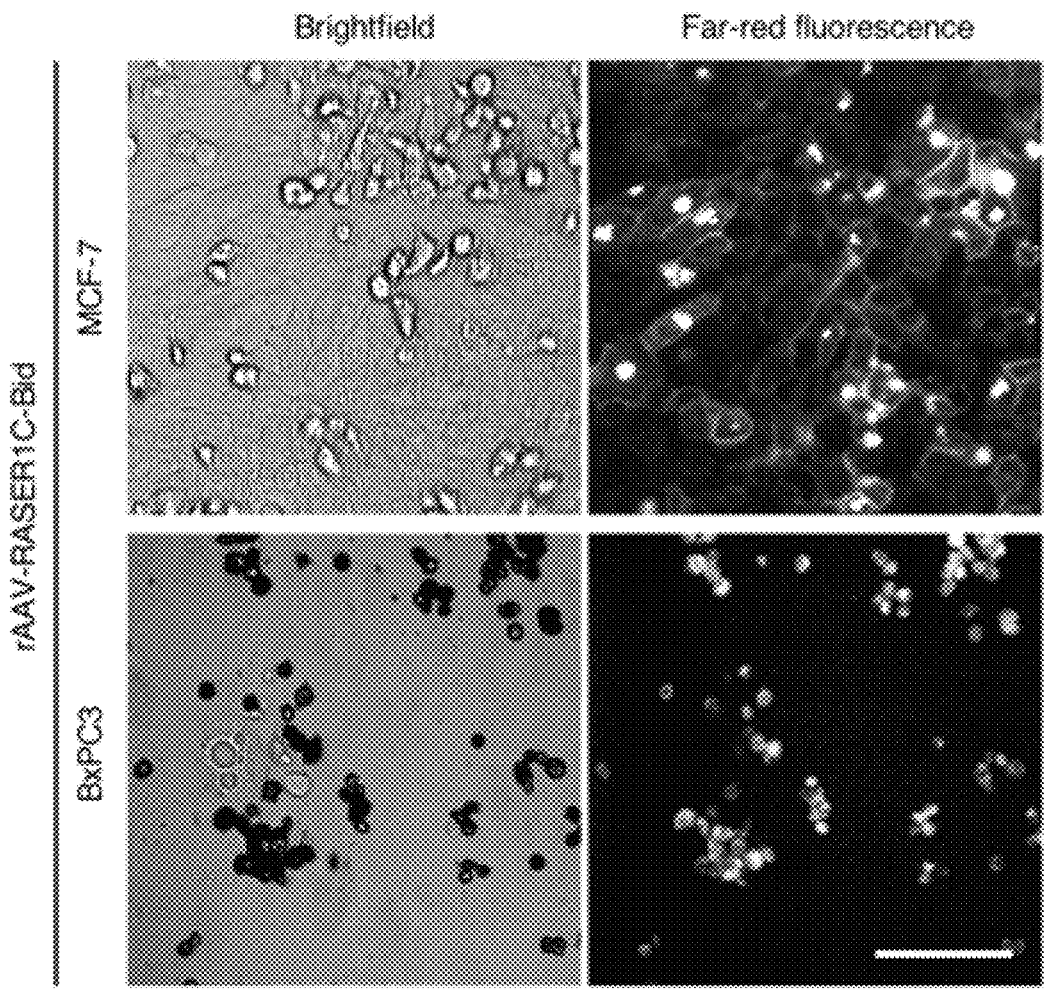
Figure 18A:
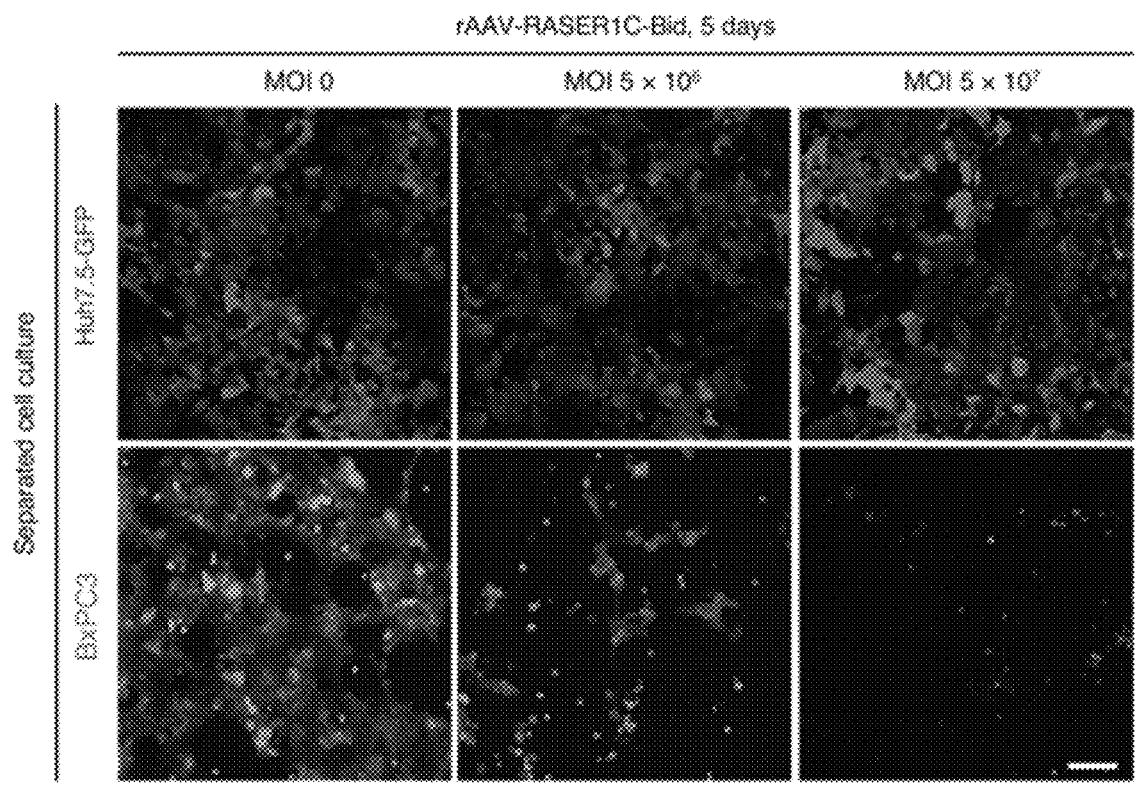
FIGS. 18A-18D show that rAAV-RASER1C-BID induces death of ErbB-hyperactive cells selectively.
Figure 18B:
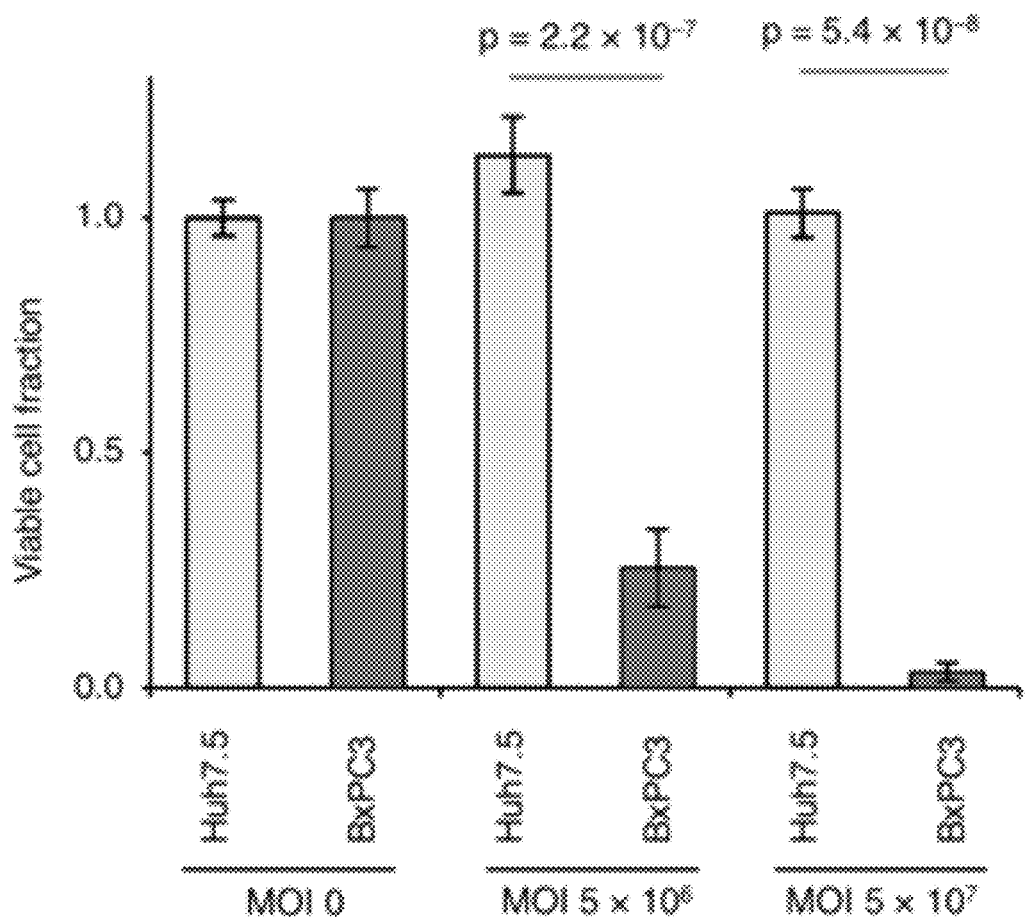

To further demonstrate its therapeutic potential, we tested RASER in a co-culture model of disseminated cancer with delivery by recombinant adeno-associated virus (rAAV). To model liver dissemination of pancreatic cancer, which carries a poor prognosis and for which surgical resection is not possible (Yamada et al. (2006) HPB (Oxford) 8:85), we differentiated human Huh7.5-GFP cells, which express normal levels of ErbB, into hepatocyte-like cells (Choi et al. (2009) Xenobiotica 39:205), then overlaid either ErbB1-hyperactive human BxPC3 pancreatic cancer cells (Walsh et al. (2013) Invest. New Drugs 31:558) or, for comparison, ErbB-normal MCF-7 cancer cells. To maximize translational potential, we used rAAV to deliver ErbB-RASER1C-BID (FIG. 17A), as rAAV is the only viral vector currently approved for gene delivery to normal tissues in the body, due to its lack of pathogenicity and genotoxicity (Naso et al. (2017) BioDrugs 31:317). mCardinal-expressing control rAAVs alone were not toxic to either BxPC3 or MCF-7 cells (FIG. 17B), and ErbB-RASER-BID-expressing and control mCardinal-expressing rAAVs were similarly infectious (FIGS. 17B, 17C). As expected, while rAAV-ErbB-RASER1C-Bid had no effect on MCF-7 cells, with the OFP-BID cargo retained at the cell membrane (FIG. 17C), rAAV-ErbB-RASER1C-BID released OFP-BID and induced apoptosis in BxPC3 cells (FIGS. 17C, 18A).

Figure 11C:
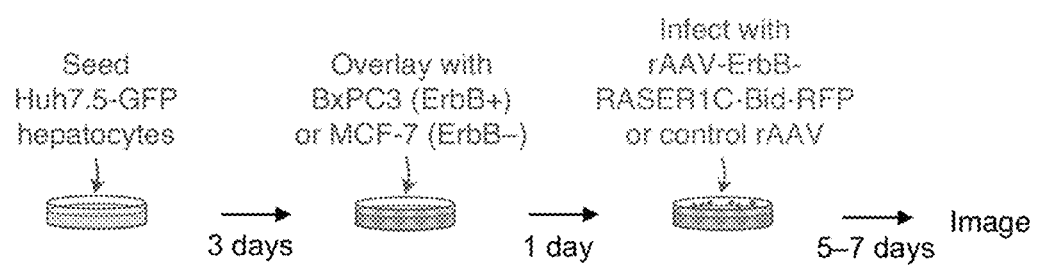
Figure 11D:
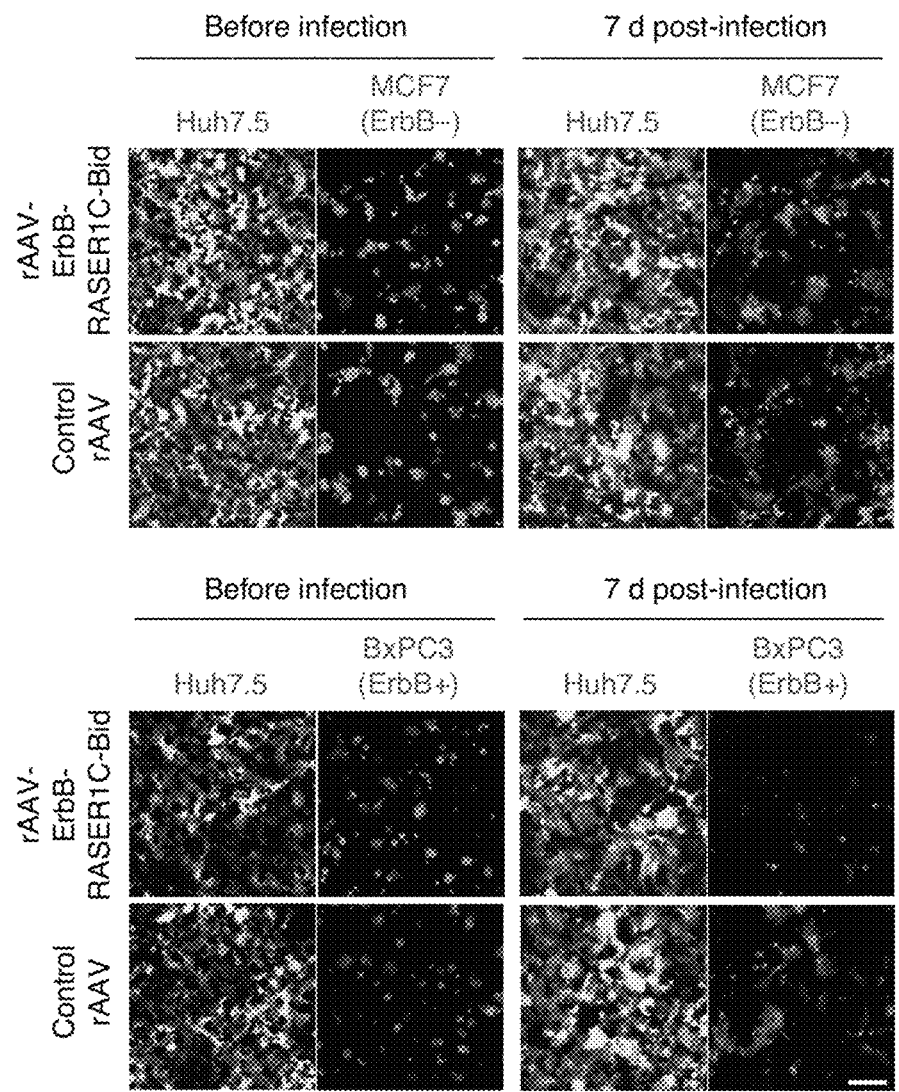
Figure 11E:
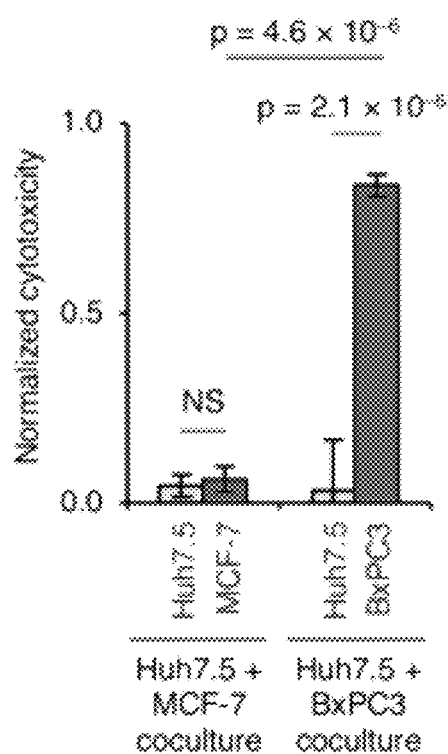
Figure 18C:
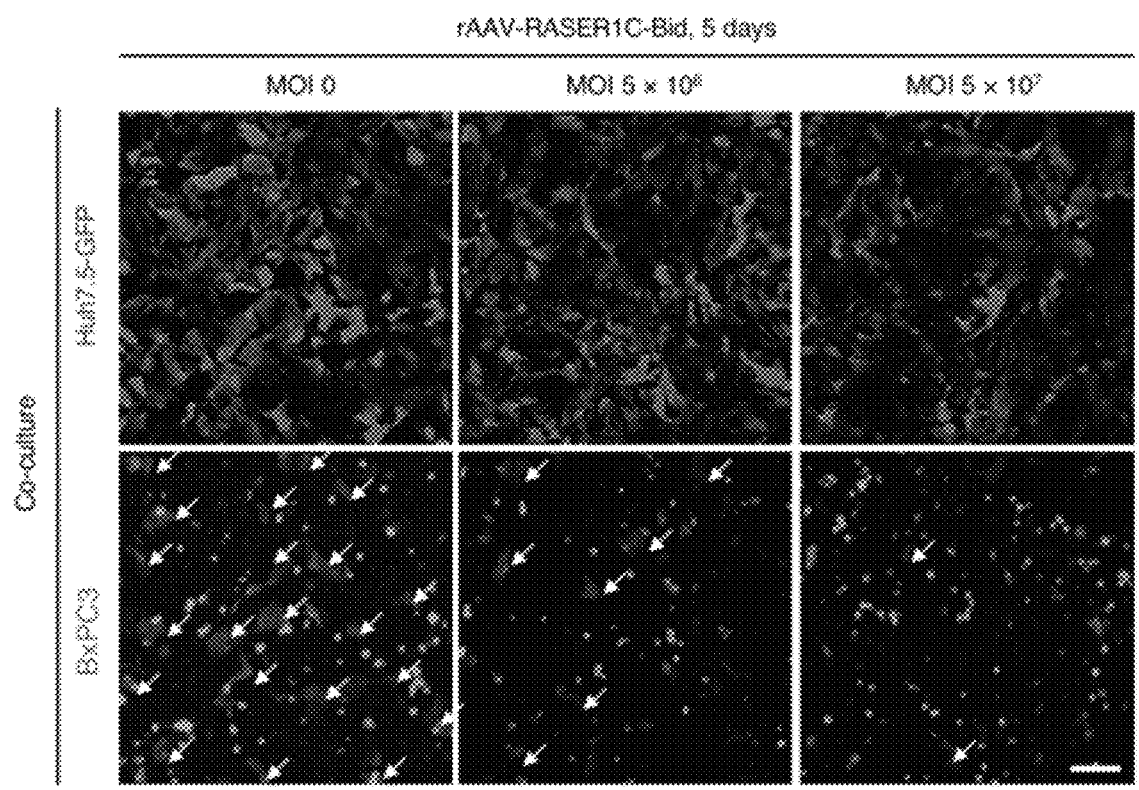
Figure 18D:
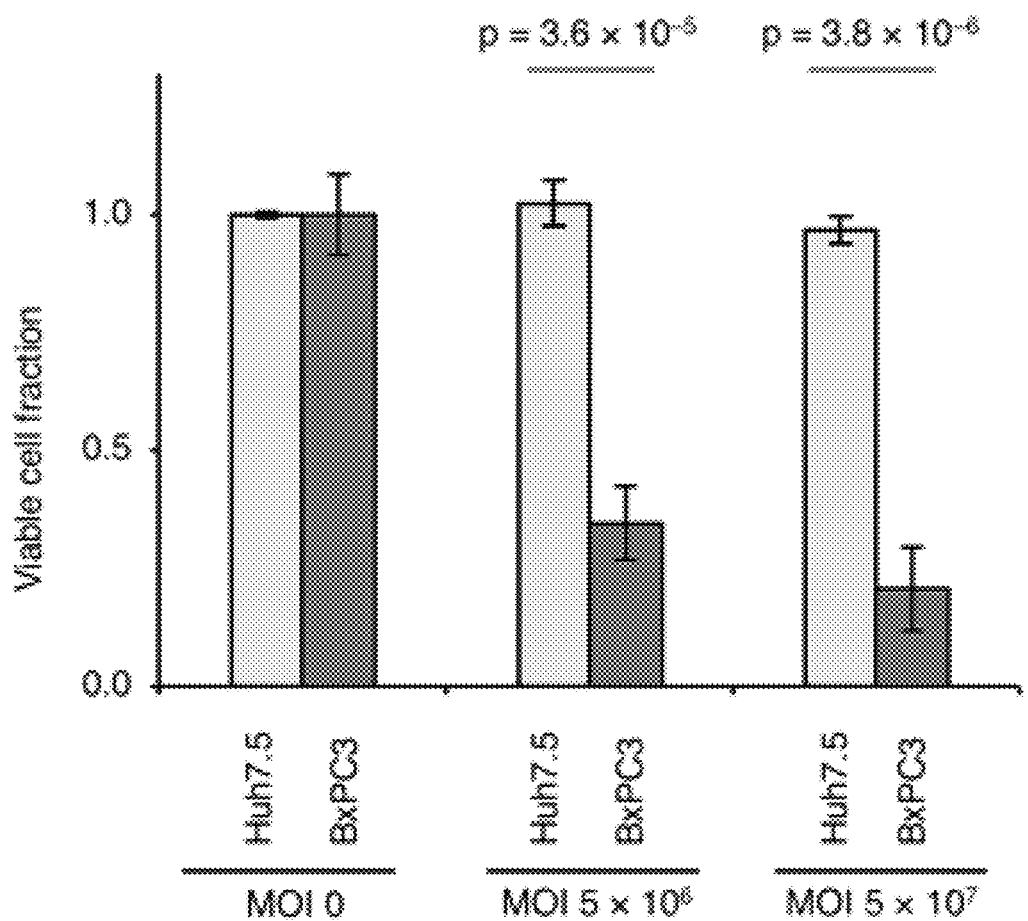

Finally, we treated the Huh7.5-BxPC3 cocultures with rAAV-ErbB-RASER1C-BID or control rAAV (FIG. 11C). As desired, rAAV-ErbB-RASER1C-Bid selectively killed the ErbB-hyperactive BxPC3 cells while sparing the cocultured Huh7.5 hepatocytes (FIGS. 11D, 11E and 18C). In contrast, when the ErbB-normal MCF-7 cells were cocultured with Huh7.5 hepatocytes, rAAV-ErbB-RASER1C-BID killed neither cell type (FIGS. 11D, 11E), confirming the specificity of ErbB-RASER1C-BID output for ErbB-hyperactive cells. Thus, ErbB-RASER-BID delivered by rAAV selectively ablates ErbB-positive pancreatic cancer cells in a co-culture model of disseminated cancer, demonstrating that RASER indeed exhibits highly selective anticancer activity.

Discussion

An intriguing possible implementation of RASER may be to generate pathway-specific oncolytic viruses, taking advantage of the ability of viruses to penetrate solid tumors more effectively than cell-based therapies (Fountzilas et al. (2017) Oncotarget 8:102617). We demonstrated that ErbB-RASER-BID delivery by nonpathogenic viral vector rAAV can specifically kill ErbB-positive cancer cells and spare normal cells. As rAAV does not naturally have tumor-selective tropism or lytic ability, these results can be viewed as converting the non-pathogenic rAAV into to a tumor-selective cytotoxic virus by expressing ErbB-RASER-BID. We also demonstrated the ability of RASER to induce cytokine release. Interestingly, systemic anti-tumor effects can be elicited by cytokine release from a subset of tumor cells (Nissim et al. (2017) Cell 171:1138), so RASER may not need to be delivered to every tumor cell in therapeutic applications if programmed to induce immunostimulation. In such a context, RASER may benefit from combination with current immunotherapies. However, while RASER viruses may function well against cancer cells in culture, additional modifications may be required for them to be efficacious and non-toxic in vivo. Some well-known challenges common to virotherapy that need to be overcome, for example, include producing sufficient viral titers, obtaining high-efficiency infections of tumors, and avoiding premature immune clearance. Solving these issues may benefit from systematic testing in immunocompetent animal cancer models of multiple parameters including viral vector types, administration routes and doses, methods to target viruses to specific cell-surface receptors, and treatments to suppress humoral immunity.

Example 4

Building and Testing a Mathematical Model of RASER

Figure 12A:
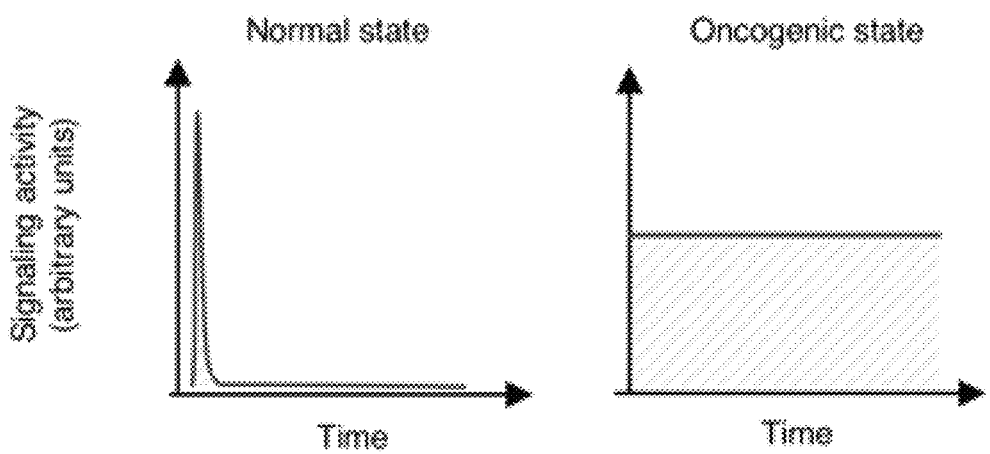
Figure 12B:
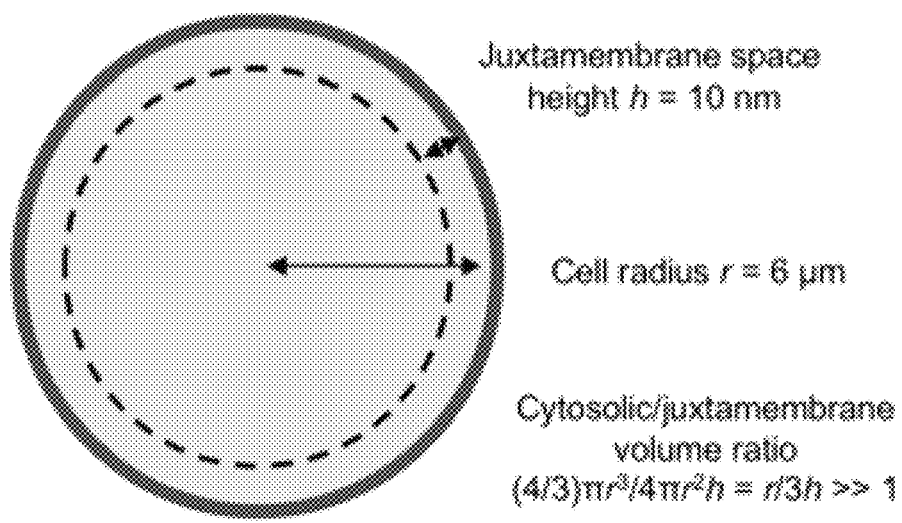

To enable rational optimization of RASER systems, we created a dynamic model of ErbB-RASER0.1 that predicts cargo accumulation over time in ErbB-off and ErbB-on states. The model required 11 parameters (FIG. 12D)—production and degradation rate constants for protease and substrate components and for substrate fragments after cleavage, pErbB abundance (DeFazio-Eli et al. (2011) Breast Cancer Res. 13:R44, Friedrich et al. (2013) Mol. Ther. 21:849, Okabe et al. (2007) Cancer Res. 67:2046, Zhang et al. (2015) Anal Chem 87, 9960), the $k_{on}$ and $k_{off}$ of the PTB-pErbB interaction (Jones et al. (2006) Nature 439:168), $K_M$ and $k_{cat}$ of the NS3-substrate reaction (Landro et al. (1997) Biochemistry 36:9340, Tong et al. (2006) Antiviral Res 70:28), and the juxtamembrane volume in which ErbB cytosolic domains reside (FIG. 12B).

Mathematical Modeling of RASER

To predict the effect of ErbB hyperactivity on rates of substrate cleavage, we consider the action of ErbB as redistributing protease and, as relevant, substrate molecules to different subcellular spaces, in two RASER configurations described below.

(i) RASER system with only protease recruited to receptor: In the absence of phosphorylated ErbB (pErbB), PTB-fused protease (PTB-pro) diffuses throughout the whole cell, leading to a low background cleavage rate of membrane-tethered substrates (Supplementary Note 1). In the presence of pErbB, some molecules of PTB-pro would be recruited to the same juxtamembrane space (jm-space) as membrane-tethered substrate. Rates of cleavage of a given number of membrane-tethered substrate molecules by a given number of pErbB-bound protease molecules in one unit of time in the kinetic model (1 s) can be calculated using the Michaelis-Menten rate equation using enzyme and substrate concentrations at that time point. The presence of long linkers between the protease domain and the PTB recruitment domain, and between the substrate sequence and the farnesylation site, suggests unrestricted movement within the jm-space. We thus assume that tethering does not alter the conformation or orientation of either enzyme or substrate in a manner that affects the binding equilibrium. Thus, as in the case of membrane-tethered substrate and cytosolic protease, we do not assume any difference in binding free-energies for enzyme and substrate in the juxtamembrane space compared to the cytosol, and thereby use $K_M$ values measured for the protease and substrates in solution. Note in the presence of pErbB, the fraction of PTB-pro remaining in the cytosol can still contribute to substrate cleavage at the background cleavage rate. Throughout one time point, the system is assumed to be in equilibrium maintained by multiple binding and unbinding events, so that overall distribution of receptor species (bound to PTB-pro vs. unbound) is unchanged.

Because all substrate molecules are tethered in the membrane, they can only produce product when they bind to protease molecules within the jm-space. The rate of product formation in this jm-space, $d[P]_{jm}/dt$, which has units of concentration per time, is given by:

$$d[P]_{jm}/dt = d[P]_{bound}/dt + d[P]_{unbound}/dt, \quad \text{(Eqn. 1)}$$

where $d[P]_{bound}/dt$ is the rate of product formation in the jm-space by protease bound to phospho-ErbB (pErbB) cleaving membrane-tethered substrate, and $d[P]_{unbound}/dt$ is the rate of product formation in the jm-space by free protease diffusing throughout the cell cleaving membrane-tethered substrate.

Per the Michaelis-Menten equation, $$d[P]_{bound}/dt = k_{cat} \cdot [\text{pErbB:PTB-pro}]_{jm} \cdot [S]_{jm}/([S]_{jm} + K_M),$$

where $[\text{pErbB:PTB-pro}]_{jm}$ is the concentration of pErbB:PTB-pro complexes in the jm-space, and $[S]_{jm}$ is the concentration of substrate in the jm-space. Also, $$d[P]_{unbound}/dt = k_{cat} \cdot [\text{PTB-pro}]_{cell,free} \cdot [S]_{jm}/([S]_{jm} + K_M),$$

where $[\text{PTB-pro}]_{cell,free}$ is the concentration of unbound protease in the cell, which is the same as the concentration of unbound protease in jm-space due to rapid exchange as jm-space is continuous with the rest of the cell. Then, $$d[P]_{jm}/dt = d[P]_{bound}/dt + d[P]_{unbound}/dt =$$
$$k_{cat} \cdot ([\text{pErbB:PTB-pro}]_{jm} + [\text{PTB-pro}]_{cell,free}) \cdot [S]_{jm}/([S]_{jm} + K_M) =$$
$$k_{cat} \cdot [\text{PTB-pro}]_{jm,total} \cdot [S]_{jm}/([S]_{jm} + K_M),$$

where $[\text{PTB-pro}]_{jm,total} = [\text{pErbB:PTB-pro}]_{jm} + [\text{PTB-pro}]_{jm,free}$ and represents the total effective concentration of protease in the juxtamembrane space.

$[\text{PTB-pro}]_{cell,total}$, the average concentration of total PTB-pro throughout the cell, is equivalent to $[\text{pErbB:PTB-pro}]_{jm}$ diluted into the whole cell plus $[\text{PTB-pro}]_{cell,free}$ or $[\text{PTB-pro}]_{jm,free}$:

$$[\text{PTB-pro}]_{cell,total} = [\text{pErbB:PTB-pro}]_{jm}/C_{jm} + [\text{PTB-pro}]_{cell,free}$$

where $C_{jm}$ is a juxtamembrane space concentration conversion factor, calculated as the ratio of the volume of a cell of radius r to the volume of a juxtamembrane space of height h. As h<<r, the volume of the juxtamembrane space can be estimated as $4\pi r^2 h$, resulting in $$C_{jm} = (4/3\pi r^3)/4\pi r^2 h = r/3h.$$

We use a typical human epithelial cell radius of 6 μm and a jm-space height of 10 nm based on the length of the ErbB cytosolic segment, so $C_{jm}=200$. $[\text{PTB-pro}]_{cell,free}$ can then be expressed in terms of $[\text{pErbB:PTB-pro}]_{jm}$ and $[\text{PTB-pro}]_{cell,total}$:

$$[\text{PTB-pro}]_{cell,free} = [\text{PTB-pro}]_{cell,total} - [\text{pErbB:PTB-pro}]_{jm}/C_{jm}. \quad \text{(Eqn. 2)}$$

Thus, the effective concentration of protease in the juxtamembrane space is:

$$[\text{PTB-pro}]_{jm,total} = [\text{pErbB:PTB-pro}]_{jm} + [\text{PTB-pro}]_{cell,free} = [\text{pErbB:PTB-pro}]_{jm} \cdot (1 - 1/C_{jm}) + [\text{PTB-pro}]_{cell,total}.$$

As $C_{jm}=200$, we can approximate $1-1/C_{jm}$ as simply 1, and the effective concentration of protease in the juxtamembrane space simplifies to:

$$[\text{PTB-pro}]_{jm,total} = [\text{pErbB:PTB-pro}]_{jm} + [\text{PTB-pro}]_{cell,total},$$

so that $$d[P]_{jm}/dt = k_{cat} \cdot [\text{PTB-pro}]_{jm,total} \cdot [S]_{jm}/([S]_{jm}+K_M) = k_{cat} \cdot ([\text{pErbB:PTB-pro}]_{jm} + [\text{PTB-pro}]_{cell,total}) [S]_{jm}/([S]_{jm}+K_M). \quad \text{(Eqn.3)}$$

The quantity $[\text{PTB-pro}]_{cell,total}$ will be modelled from measured protein production and degradation rates, and $[S]_{jm}$ will be modelled from production, degradation, and cleavage rates, so the only remaining variable to calculate is $[\text{pErbB:PTB-pro}]_{jm}$. We can relate $[\text{pErbB:PTB-pro}]_{jm}$ to the known dissociation constant for pErbB:PTB-pro and the modelled $[\text{PTB-pro}]_{cell,total}$ as follows. Defining $[\text{pErbB}]_{jm,free}$ and $[\text{pErbB}]_{jm,total}$ as the concentrations of unbound and total pErbB in jm-space, respectively, then $$[\text{pErbB}]_{jm,free} = [\text{pErbB}]_{jm,total} - [\text{pErbB:PTB-pro}]_{jm}, \quad \text{(Eqn. 4)}$$

where $[\text{pErbB}]_{jm,total}$ will be calculated from published measurements of total pErbB numbers per cell (DeFazio-Eli et al. (2011) Breast Cancer Res 13:R44).

Assuming binding of pErbB and PTB is at equilibrium with a dissociation constant of $K_{D,PTB}$, then:

$$K_{D,PTB} = [\text{pErbB}]_{jm,free} \cdot [\text{PTB-pro}]_{cell,free}/[\text{pErbB:PTB-pro}]_{jm},$$

or $[\text{pErbB:PTB-pro}]_{jm} = [\text{pErbB}]_{jm,free} \cdot [\text{PTB-pro}]_{cell,free}/K_{D,PTB}. \quad \text{(Eqn.5)}$ Substitution of Eqns. 2 and 4 into Eqn. 5 produces $$[\text{pErbB:PTB-pro}]_{jm} = ([\text{pErbB}]_{jm,total} - [\text{pErbB:PTB-pro}]_{jm}) \cdot ([\text{PTB-pro}]_{cell,total} - [\text{pErbB:PTB-pro}]_{jm}/C_{jm})/K_{D,PTB}.$$

Using x to represent $[\text{pErbB:PTB-pro}]_{jm}$, p to represent $[\text{pErbB}]_{jm,total}$, and q to represent $[\text{PTB-pro}]_{cell,total}$, $$x=(p-x)\cdot(q-x/C_{jm})/K_{D,PTB},$$

or $K_{D,PTB}\cdot x = x^2/C_{jm} - q\cdot x - p\cdot x/C_{jm} + p\cdot q,$ or $C_{jm}\cdot K_{D,PTB}\cdot x = x^2 - C_{jm}\cdot q\cdot x - p\cdot x + C_{jm}\cdot p\cdot q,$ or $0 = x^2 - (p + C_{jm}\cdot q + C_{jm}\cdot K_{D,PTB})\cdot x + C_{jm}\cdot p\cdot q.$ Per the quadratic formula, $$x = (y \pm (y^2 - 4C_{jm}\cdot p\cdot q)^{1/2})/2, \text{ where } y = (p + C_{jm}\cdot q + C_{jm}\cdot K_{D,PTB}).$$

Restoring full names for x, p, and q, $$[\text{pErbB:PTB-pro}]_{jm} = (y + (y^2 - 4C_{jm}\cdot[\text{pErbB}]_{jm,total}\cdot[\text{PTB-pro}]_{cell,total})^{1/2})/2, \text{ where } y = [\text{pErbB}]_{jm,total} + C_{jm}\cdot[\text{PTB-pro}]_{cell,total} + C_{jm}\cdot K_{D,PTB}.$$

Of the two possible solutions, only the following one converges to $[\text{pErbB}]_{jm,total}$ when $[\text{PTB-pro}]_{cell,total}$ approaches infinity and is therefore valid:

$$[\text{pErbB:PTB-pro}]_{jm} = (y - (y^2 - 4C_{jm}\cdot[\text{pErbB}]_{jm,total}\cdot[\text{PTB-pro}]_{cell,total})^{1/2})/2, \text{ where } y = [\text{pErbB}]_{jm,total} + C_{jm}\cdot[\text{PTB-pro}]_{cell,total} + C_{jm}\cdot K_{D,PTB}. \quad \text{(Eqn. 6)}$$

Returning to the rate of product formation in terms of concentration in the jm-space (Eqn. 3), we can now enter values for $[\text{pErbB-PTB-pro}]_{jm}$ as calculated by Eqn. 6 and for $[\text{PTB-pro}]_{cell,total}$ as modelled from protein synthesis and degradation rates. To convert this to product formation rate in terms of concentration in the entire cell, we divide by $C_{jm}$, i.e.

$$d[P]_{cell}/dt = (d[P]_{jm}/dt)/C_{jm}.$$

Finally, the change over time in released cargo concentration in the cell ($[\text{released cargo}]_{cell}$) is described by $$d[\text{released cargo}]_{cell}/dt = d[P]_{cell}/dt - k_{deg,released\ cargo}[\text{released cargo}]_{cell},$$

with $[\text{released cargo}]_{cell} = 0$ M at $t=0$.

Changes in $[\text{PTB-pro}]_{cell,total}$ and $[S]_{cell}$ over time are described by $$d[\text{PTB-pro}]_{cell,total}/dt = k_{syn} - k_{deg,PTB-pro}[\text{PTB-pro}]_{cell,total}, \text{ with } [\text{PTB-pro}]_{cell,total} = 0 \text{ M at } t=0$$

and $d[S]_{cell}/dt = k_{syn} - k_{deg,S}[S]_{cell} - d[P]_{cell}/dt,$ with $[S]_{cell} = 0$ M at $t=0$.

The above ordinary differential equations were solved with MATLAB (Mathworks) using the function ode15s to obtain instantaneous values for $[\text{released cargo}]_{cell}$, $[\text{PTB-pro}]_{cell,total}$, and $[S]_{cell}$ at times following introduction of RASER components into cells. Data from MATLAB were exported to Excel (Microsoft) to generate graphs.

(ii) RASER system with substrate and protease recruited to receptor: ErbB dimerizes upon overexpression or oncogenic mutation, followed by autophosphorylation (Brennan et al. (2000) Oncogene 19:6093), so for simplicity we assume all pErbB molecules are dimerized. If substrate can also associate directly with pErbB, then some of the PTB-pro bound at a pErbB dimer will be in the immediate vicinity of a SH2-substrate (SH2-sub) molecule bound to the dimer. For a single molecule each of PTB-pro and SH2-sub binding to a pErbB dimer, assuming confinement within a volume of radius 5 nm, the effective [E] and [S] each exceed 3 mM. As $[S] \gg K_M$, the enzyme should be fully occupied by substrate. Product formation rate will then be the slower of $k_{cat}$ or the time for cleaved SH2 to unbind from receptor and be replaced with another SH2-sub molecule. For HCV protease, $k_{cat}$ is <0.2 s$^{-1}$, while SH2 dwell time has been measured at 0.5 s$^{-1}$ in the context of intact transmembrane receptor in living cells (Oh et al. (2012) Proc. Natl. Acad. Sci. U.S.A.). Thus $k_{cat}$ and not dissociation of cleaved SH2 is limiting for product formation, and we can estimate product formation rate as $k_{cat}$ for each SH2-sub molecule bound to a pErbB dimer that also binds 1 or 2 molecules of PTB-pro. In addition, the remaining fraction of ErbB-bound PTB-pro will still be able to interact with the fraction of substrate molecules in the juxtamembrane space (unbound to ErbB, or bound to ErbB molecules that are not also bound to PTB-pro), at the rate described in (i) above. The fraction of PTB-pro remaining in the cytosol can also still contribute to substrate cleavage at the background cleavage rate described in (i) above. Note that throughout one unit time, the system is assumed to be in equilibrium maintained by multiple binding and unbinding events, so that overall distribution of receptor species is unchanged.

The above concepts were used to establish a model for the dually targeted RASER as follows. The rate of product formation in the jm-space, $d[P]_{jm}/dt_{dual}$, which has units of concentration per time, is given by $$d[P]_{jm}/dt_{dual} = d[P]_{bound,bound}/dt + d[P]_{bound,unbound}/dt + d[P]_{unbound,unbound}/dt,$$

where $d[P]_{bound,bound}/dt$ is the rate of product formation by protease bound to phosphorylated ErbB (pErbB) cleaving pErbB-bound substrate, $d[P]_{bound,unbound}/dt$ is the rate of product formation by protease bound to pErbB cleaving unbound membrane-tethered substrate, and $d[P]_{unbound,unbound}/dt$ is the rate of product formation by free protease diffusing throughout the cell cleaving unbound membrane-tethered substrate, with all concentrations calculated in the jm-space. The last two terms, $d[P]_{bound,unbound}/dt$ and $d[P]_{unbound,unbound}/dt$, are identical to the terms of Eqn. 1 in part (i). Therefore, per Eqns. 3 and 6, $$d[P]_{jm}/dt_{dual} = d[P]_{bound,bound}/dt + k_{cat}\cdot([\text{pErbB:PTB-pro}]_{jm} + [\text{PTB-pro}]_{cell,total})\cdot[\text{SH2-sub}]_{jm,free}/([\text{SH2-sub}]_{jm,free} + K_M),$$

with $[\text{pErbB:PTB-pro}]_{jm} = (y - (y^2 - 4C_{jm}\cdot[\text{pErbB}]_{jm,total}\cdot[\text{PTB-pro}]_{cell,total})^{1/2})/2,$ where $y = [\text{pErbB}]_{jm,total} + C_{jm}\cdot[\text{PTB-pro}]_{cell,total} + C_{jm}\cdot K_{D,PTB}.$ (Eqn. 7)

To calculate $d[P]_{bound,bound}/dt$, we modelled the distribution of all possible species of pErbB dimers bound to PTB-pro and/or SH2-sub. We assumed independent association of PTB and SH2, and define the fraction of pErbB bound by PTB-pro as:

$$F_{pErbB:PTB-pro/pErbB} = [\text{pErbB:PTB-pro}]_{jm}/[\text{pErbB}]_{jm,total}. \quad \text{(Eqn. 8)}$$

Substituting the expression for $[\text{pErbB:PTB-pro}]_{jm}$ from Eqn. 7 into Eqn. 8 yields $$F_{pErbB:PTB-pro/pErbB} = (y - (y^2 - 4C_{jm}\cdot[\text{pErbB}]_{jm,total}\cdot[\text{PTB-pro}]_{cell,total})^{1/2})/2[\text{pErbB}]_{jm,total},$$

where $y = [\text{pErbB}]_{jm,total} + C_{jm}\cdot[\text{PTB-pro}]_{cell,total} + C_{jm}\cdot K_{D,PTB}.$ (Eqn. 9)

We define the fraction of pErbB bound by SH2-sub as:

$$F_{pErbB:SH2-sub/pErbB} = [\text{pErbB:SH2-sub}]_{jm}/[\text{pErbB}]_{jm,total}. \quad \text{(Eqn. 10)}$$

Unfused SH2 domains produced from earlier cleavage of SH2-sub can also associate with pErbB, but only pErbB:SH2-sub complexes contribute to product formation. Assuming cleaved SH2 and SH2-sub have the same $K_D$, the fraction of productive pErbB:SH2 complexes out of those involving all SH2 domains will be equivalent to the fraction of all SH2 domains consisting of uncleaved SH2-sub. For purposes of simplifying the calculation of [pErbB:SH2-sub]$_{jm}$, we will first calculate [pErbB:anySH2]$_{jm}$, the concentration of pErbB bound to any SH2 domain (cleavedSH2 or SH2-sub) in the jm-space, which can then yield [pErbB:SH2-sub]$_{jm}$ by proportionality:

[pErbB:SH2-sub]$_{jm}$=[pErbB:anySH2]$_{jm}$·
[SH2-sub]$_{jm,total}$/[anySH2]$_{jm,total}$, where
[anySH2]$_{jm,total}$=[SH2-sub]$_{jm,total}$+
[cleavedSH2]$_{jm,total}$. (Eqn. 11)

Substituting this new definition into Eqn 10 yields $F_{pErbB:SH2-sub/pErbB}$=([pErbB:anySH2]$_{jm}$·
[SH2-sub]$_{jm,total}$)/([pErbB]$_{jm,total}$·
[anySH2]$_{jm,total}$). (Eqn. 12)

To calculate [pErbB:anySH2]$_{jm}$, we take the same approach as in (i):

[pErbB]$_{jm,free}$=[pErbB]$_{jm,total}$−[pErbB:anySH2]$_{jm}$ (Eqn. 13)

and [anySH2]$_{jm,free}$=[anySH2]$_{jm,total}$−[pErbB:anySH2]$_{jm}$, (Eqn. 14)

where [pErbB]$_{jm,free}$ in this case refers to pErbB that is not bound to any SH2 domain.

Assuming binding of pErbB and SH2 is at equilibrium with a dissociation constant of $K_D$,SH2, then:

$K_{D,SH2}$=[pErbB]$_{jm,free}$[anySH2]$_{jm,free}$/[pErbB:anySH2]$_{jm}$, or $K_{D,SH2}$·[pErbB:anySH2]$_{jm}$=[pErbB]$_{jm,free}$
[anySH2]$_{jm,free}$. (Eqn. 15)

Substitution of Eqns. 13 and 14 into Eqn. 15 produces:

$K_{D,SH2}$[pErbB:anySH2]$_{jm}$=([pErbB]$_{jm,total}$−[pErbB:anySH2]$_{jm}$)([anySH2]$_{jm,total}$−[pErbB:anySH2]$_{jm}$).

Using x to represent [pErbB:anySH2]$_{jm}$, p to represent [pErbB]$_{jm,total}$, and q to represent [anySH2]$_{jm,total}$, $K_{D,SH2}$·x=(p−x)·(q−x), or $K_{D,SH2}$·x=$x^2$−q·x−p·x+p·q, or 0=$x^2$−(p+q+$K_{D,PTB}$)·x+p·q.

Per the quadratic formula, x=(z±$(z^2−4pq)^{1/2}$)/2, where z=(p+q+$K_{D,SH2}$).

Restoring full names for x, p, and q,

[pErbB:anySH2]$_{jm}$=(z±$(z^2$−4[pErbB]$_{jm,total}$
[anySH2]$_{jm,total})^{1/2}$)/2, where z=[pErbB]$_{jm,total}$+
[anySH2]$_{jm,total}$+$K_{D,SH2}$.

Of the two solutions, only one converges to [pErbB]$_{jm,total}$ when [anySH2]$_{jm,total}$ approaches infinity and is therefore valid:

[pErbB:anySH2]$_{jm}$=(z−$(z^2$−4[pErbB]$_{jm,total}$·
[anySH2]$_{jm,total})^{1/2}$)/2, where z=[pErbB]$_{jm,total}$+[anySH2]$_{jm,total}$+$K_{D,SH2}$. (Eqn.16)

Note per Eqn. 11,

[pErbB:SH2-sub]$_{jm}$=[pErbB:anySH2]$_{jm}$·
[SH2-sub]$_{jm,total}$/[anySH2]$_{jm,total}$=(z−$(z^2$−4
[pErbB]$_{jm,total}$·[anySH2]$_{jm,total})^{1/2}$
[SH2-sub]$_{jm,total}$)/2[anySH2]$_{jm,total}$,
where z=[pErbB]$_{jm,total}$+[anySH2]$_{jm,total}$+
$K_{D,SH2}$. (Eqn.17)

Substituting Eqn. 16 into Eqn. 12, or Eqn. 17 into Eqn. 10, yields:

$F_{pErbB:SH2-sub/pErbB}$=(z−$(z^2$−4[pErbB]$_{jm,total}$
[anySH2]$_{jm,total})^{1/2}$)·[SH2-sub]$_{jm,total}$/
(2[anySH2]$_{jm,total}$[pErbB]$_{jm,total}$), where z=[pErbB]$_{jm,total}$+[anySH2]$_{jm,total}$+$K_{D,SH2}$. (Eqn. 18)

To calculate the number of cleavage events in j-space in the ErbB-on state, we considered four states of an individual pErbB chain. The fractions of each state are:

$F_{pE:p,s}$:=Fraction of pErbB chains bound to both PTB-pro and SH2-sub=
$F_{pErbB:PTB-pro/pErbB}$·$F_{pErbB:SH2-sub/pErbB}$, $F_{pE:p,0}$:=Fraction of pErbB chains bound to PTB-pro only=$F_{pErbB:PTB-pro/pErbB}$·(1−
$F_{pErbB,SH2-sub/pErbB}$), $F_{pE:0,s}$:=Fraction of pErbB chains bound to SH2-sub only=$F_{pErbB,SH2-sub/pErbB}$·
(1−$F_{pErbB,PTB-pro/pErbB}$), $F_{pE:0,0}$:=Fraction of pErbB chains bound to neither=
(1−$F_{pErbB,PTB-pro/pErbB}$)·(1−$F_{pErbB,SH2-sub/pErbB}$).

Four states of pErbB dimers contain at least one molecule each of bound PTB-pro or SH2-sub, thereby mediating product formation at a rate limited by SH2 exchange. These four states occur at the following frequencies:

$F_{2pE:1p,1s}$:=Fraction of pErbB dimers bound to 1 PTB-pro and 1 SH2-sub=$F_{pE:p,s}$·$F_{pE:0,0}$+$F_{pE:p,0}$·$F_{pE:0,s}$, $F_{2pE:1p,2s}$:=Fraction of pErbB dimers bound to 1 PTB-pro and 2 SH2-sub=$F_{pE:p,s}$·$F_{pE:0,s}$, $F_{2pE:2p,1s}$:=Fraction of pErbB dimers bound to 2 PTB-pro and 1 SH2-sub=$F_{pE:p,s}$·$F_{pE:p,0}$, $F_{2pE:2p,2s}$:=Fraction of pErbB dimers bound to 2 PTB-pro and 2 SH2-sub=$F_{pE:p,s}$·$F_{pE:p,s}$.

When pErbB dimers bind PTB-pro and SH2-sub simultaneously, we can assume full enzyme occupancy. The rate of product formation per pErbB dimer will be limited by the number of PTB-pro or SH2-sub molecules, whichever is fewer. Among pErbB dimers binding both PTB-pro and SH2-sub, product formation rate will be $k_{cat}$ if either one PTB-pro or one SH2-sub molecule is bound, and 2$k_{cat}$ if two PTB-pro and two SH2-sub molecules are bound.

Because the concentration of dimers in the jm-space is [pErbB]$_{jm,total}$/2, the total product formation rate from cleavage of pErbB-bound SH2-sub molecules is given by:

$d[P]_{bound,bound}/dt=k_{cat}$[pErbB]$_{jm,total}$·($F_{2pE:1p,1s}$+
$F_{2pE:1p,2s}$+$F_{2pE:2p,1s}$+2$F_{2pE:2p,2s}$)/2. (Eqn. 19)

Substituting Eqns. 16 into Eqn. 7, the total rate of cleavage is given by $$d[P]_{jm}/dt_{dual} = k_{cat} \cdot [pErbB]_{jm,total} \cdot$$ (Eqn. 20)

$$(F_{2pE:1p,1s} + F_{2pE:1p,2s} + F_{2pE:2p,1s} + 2F_{2pE:2p,2s})/2 +$$

$$k_{cat} \cdot ([pErbB:PTB\text{-}pro]_{jm} + [PTB\text{-}pro]_{cell,total}) \cdot$$

$$\frac{[SH2\text{-}sub]_{jm,free}}{([SH2\text{-}sub]_{jm,free} + K_M)}.$$

Substituting $[SH2\text{-}sub]_{jm,free}=[SH2\text{-}sub]_{jm,total}-[pErbB:SH2\text{-}sub]_{jm}$ yields:

$$d[P]_{jm}/dt_{dual} = k_{cat} \cdot [pErbB]_{jm,total} \cdot \quad \text{(Eqn. 21)}$$
$$(F_{2pE:1p,1s} + F_{2pE:1p,2s} + F_{2pE:2p,1s} + 2F_{2pE:2p,2s})/2 +$$
$$k_{cat} \cdot ([pErbB:PTB\text{-}pro]_{jm} + [PTB\text{-}pro]_{cell,total}) \cdot$$
$$\frac{([SH2\text{-}sub]_{jm,total} - [pErbB:SH2\text{-}sub]_{jm})}{([SH2\text{-}sub]_{jm,total} - [pErbB:SH2\text{-}sub]_{jm} + K_M)},$$

where the two concentrations $[pErbB:PTB\text{-}pro]_{jm}$ and $[pErbB:SH2\text{-}sub]_{jm}$ are as described by Eqns. 6 and 17:

$[pErbB:PTB\text{-}pro]_{jm}=(y-(y^2-4C_{jm}\cdot[pErbB]_{jm,total}\cdot[PTB\text{-}pro]_{cell,total})^{1/2})/2$, where $y=[pErbB]_{jm,total}+C_{jm}\cdot[PTB\text{-}pro]_{cell,total}+C_{jm}\cdot K_{D,PTB}$, and $[pErbB:SH2\text{-}sub]_{jm}=(z-(z^2-4[pErbB]_{jm,total}[anySH2]_{jm,total})^{1/2}[SH2\text{-}sub]_{jm,total})/2[anySH2]_{jm,total}$, where $z=[pErbB]_{jm,total}+[anySH2]_{jm,total}+K_{D,SH2}$ and $[anySH2]_{jm,total}=[SH2\text{-}sub]_{jm,total}+[cleavedSH2]_{jm,total}$.

To convert this to product formation rate in whole-cell concentration terms, we divide by $C_{jm}$, i.e.

$$d[P]_{cell}/dt_{dual}=(d[P]_{jm}/dt_{dual})/C_{jm}.$$

Finally, the change over time in released cargo concentration in the cell ($[released\ cargo]_{cell}$) is described by:

$$d[released\ cargo]_{cell}=d[P]_{cell}/dt_{dual}-k_{deg,\ released\ cargo}[released\ cargo]_{cell},$$

with $[released\ cargo]_{cell}=0$ at $t=0$.

Changes in $[PTB\text{-}pro]_{cell,total}$, $[SH2\text{-}sub]_{cell,total}$, and $[cleavedSH2]_{cell,total}$ over time are described by:

$$d[PTB\text{-}pro]_{cell,total}/dt=k_{syn}-k_{deg,PTB\text{-}pro}[PTB\text{-}pro]_{cell,total},$$

with $[PTB\text{-}pro]_{cell,total}=0$ at $t=0$, $$d[SH2\text{-}sub]_{cell,total}/dt=k_{syn}-k_{deg,SH2\text{-}sub}[SH2\text{-}sub]_{cell,total}-d[P]_{cell}/dt_{dual},$$

with $[SH2\text{-}sub]_{cell,total}=0$ at $t=0$, and $d[cleavedSH2]_{cell,total}/dt=d[P]_{cell}/dt_{dual}-k_{deg,cleavedSH2}[cleavedSH2]_{cell,total}$, with $[cleavedSH2]_{cell,total}=0$ at $t=0$.

$[SH2\text{-}sub]_{jm,total}$ was then calculated as $C_{jm}\cdot[SH2\text{-}sub]_{cell,total}$, and $[cleavedSH2]_{jm,total}$ as $C_{jm}\cdot[cleavedSH2]_{cell,total}$.

The above ordinary differential equations were solved with MATLAB using the function ode15s to obtain values for $[released\ cargo]_{cell}$, $[PTB\text{-}pro]_{cell}$, total, and $[S]_{cell}$ at times following introduction of RASER components into cells. Data from MATLAB were exported to Excel to generate graphs.

Calculating the Effect of Membrane Tethering of Substrate in Suppressing Cleavage by Protease To determine the effectiveness of membrane tethering of substrate in suppressing basal cleavage by a cytosolic protease, we calculated cleavage rates when substrate is either cytosolic or membrane-bound. If both protease and substrate are diffusely cytosolic, cleavage rate according to the Briggs and Haldane formulation of the Michaelis-Menten equation is $$dP_{free,free}/dt=k_{cat}[E][S]_{jm}/([S]+K_M),$$

where $dP/dt_{free,free}$ is the product formation rate assuming free cytosolic localization of substrate and protease, $[E]$ is mean enzyme concentration throughout the cytosol, $[S]$ is mean substrate concentration throughout the cytosol, and $K_M$ is the Michaelis constant measured under standard-conditions, equal to $(k_{off}+k_{cat})/k_{on}$.

If enzyme remains free in the cytosol while the same total amount of substrate becomes membrane-bound, cleavage occurs only by protease in a juxtamembrane space (jm-space), which can be estimated as $$dP_{free,memb}/dt=k_{cat}[E][S]_{jm}/([S]_{jm}+K_M)$$

where $[S]_{jm}=C_{jm}[S]$.

Here, $C_{jm}$ is a juxtamembrane space concentration conversion factor, calculated as the ratio of the volume of a cell of radius r to the volume of a jm-space volume of height h, estimated as $$C_{jm}=(4/3\pi r^3)/4\pi r^2 h=r/3h.$$

We estimate a cell radius of 6 μm and a jm-space height of 10 nm, so $C_{jm}=200$.

We considered whether enzyme-substrate pairs would exhibit a different apparent $K_M$ when the substrate is membrane-tethered compared to the value measured with freely diffusing substrate. For instance, almost all enzyme-substrate collisions will involve enzyme diffusing from the cytosolic side of the substrate, so the 2-fold reduction in possible approach angles can be expected to lead to a 2-fold reduction in the frequency of collisions between enzyme and substrate and a corresponding decrease in $k_{on}$. As $K_M=(k_{off}+k_{cat})/k_{on}$, this might be expected to increase $K_M$. However, the same membrane that prevents approach from one side will also reduce $k_{off}$, by either sterically preventing dissociation from one side, or restricting diffusion immediately after dissociation and allowing re-association. These individual changes are impossible to predict with certainty a priori, but whether overall $K_M$ is likely to change can be considered in energetic terms. For sequence-specific viral proteases HCV NS3 and TEV, $k_{off} \gg k_{cat}$ (for HCV NS3 protease with NS4a cofactor and an optimal substrate, $k_{cat}=0.6$ s while $k_{off}=86$ s$^{-1}$, where $k_{off}$ was calculated from the equation $k_{off}=k_{on}\cdot K_M-k_{cat}$ using measured values for $k_{on}$, $K_M$, and $k_{cat}$ of 2.7 μM$^{-1}$ s$^{-1}$, 32 μM, and 0.6 s$^{-1}$, respectively (Landro et al. (1997) Biochemistry 36:9340, Fattori et al. (2000) J. Biol. Chem. 275:15106). $K_M$ is therefore essentially equivalent to $K_D$. The $K_D$ of an interaction is eJG/RT where ΔG is the free energy change upon enzyme-substrate binding. Given that the substrate is tethered via a flexible linker, there is no reason to expect a change in the ΔG of enzyme-substrate binding. For example, there is no reason to expect that the substrate sequence assumes a different conformation after tethering in a way that affects enzyme binding, or that it is located close enough to the membrane to hinder enzyme access. Thus we assume energetics are not changed by membrane tethering, which would suggest that $K_D$ (and thereby $K_M$) are also not changed. Assumptions of unaltered energetics when tethers are added or removed is standard in the field, and are why the $K_D$ between a phosphorylated transmembrane receptor and cytosolic SH2- or PTB-containing proteins in a cell is assumed to be well represented by the $K_D$ between a soluble phosphopeptide and a surface-bound SH2 or PTB domain (Laminet et al. (1996) J. Biol. Chem. 271:264).

In the case where enzyme is cytosolic while substrate is membrane-bound, cleavage only occurs in 1/C of the cell volume, so the relative total cleavage in a cell with membrane vs cytosolic localization of substrate, for the same total number of substrate molecules per cell, is $$(1/C_{jm})(dP_{free,memb}/dt)/(dP_{free,free}/dt)=([S]+K_M)/([S]_{jm}+K_M)=([S]+K_M)/(C_{jm}[S]+K_M).$$

This equation shows that total cleavage with membrane-bound substrate will be lower than with the same amount of cytosolic substrate across all possible substrate numbers, confirming membrane tethering suppresses substrate cleavage by cytosolic protease. The suppressing effect becomes negligible as [S] approaches zero, and approaches $1/C_{jm}$ for $[S]\gg K_M$.

Figure 12C:
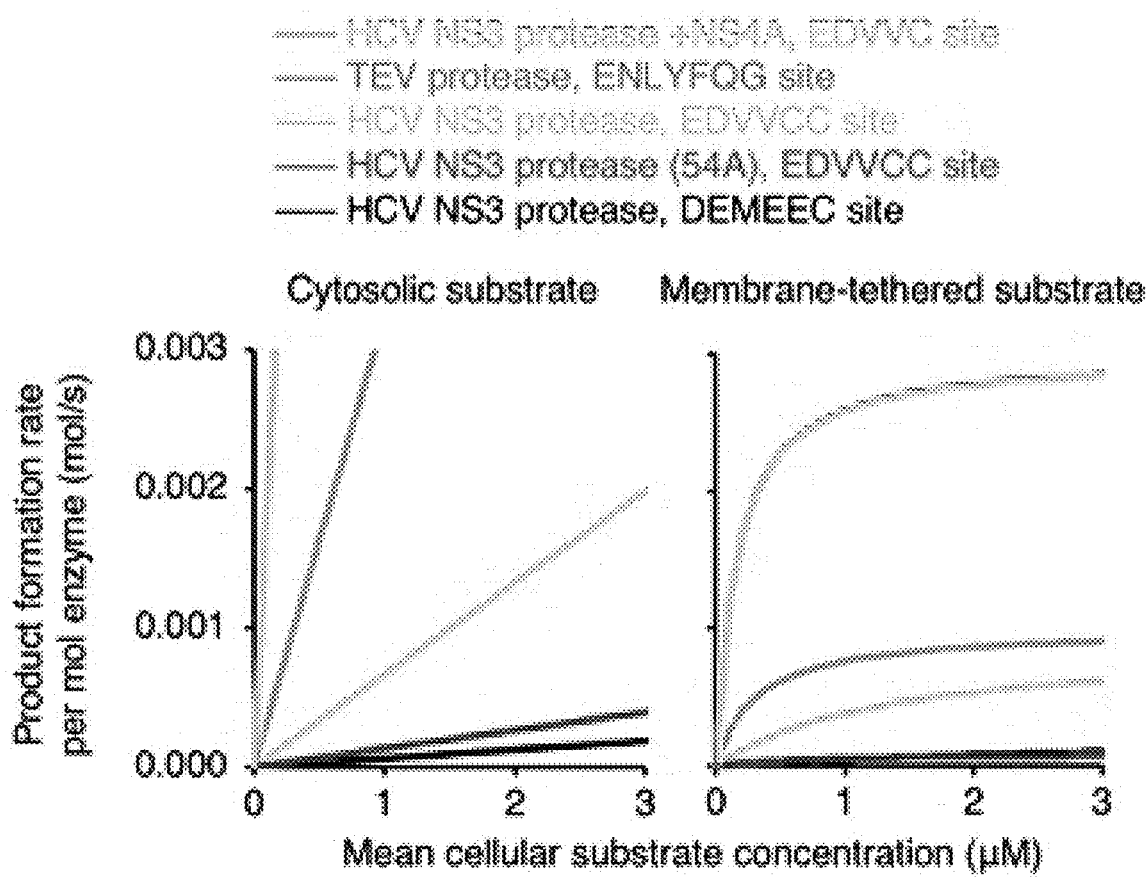

We plotted $dP/dt_{cyto,cyto}$ and $dP/dt_{jm,memb}$ using $k_{cat}$ and $K_M$ values for the site-specific tobacco etch virus (TEV) protease and hepatitis C virus (HCV) NS3 protease (with or without the NS4A cofactor). The results confirmed that membrane sequestration should reduce basal cleavage by a cytosolic protease, especially as substrate amounts increase (FIG. 12C).

Calculating Protein Degradation and Production Rates

Figure 13A:
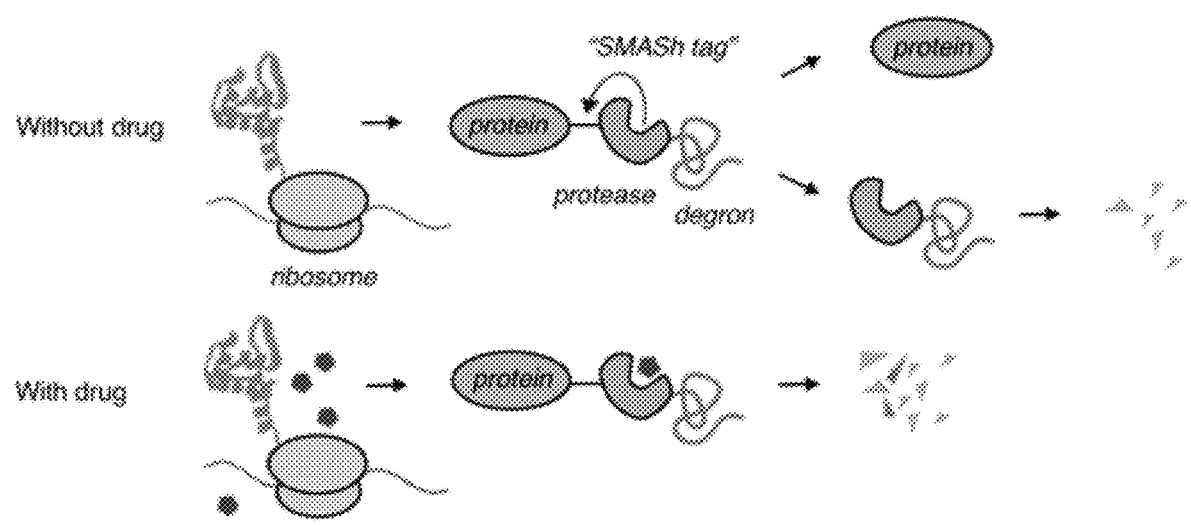
Figure 13B:
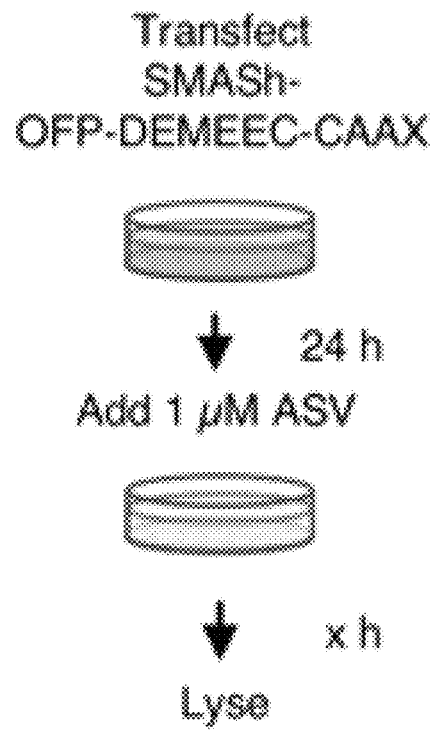
Figure 13C:
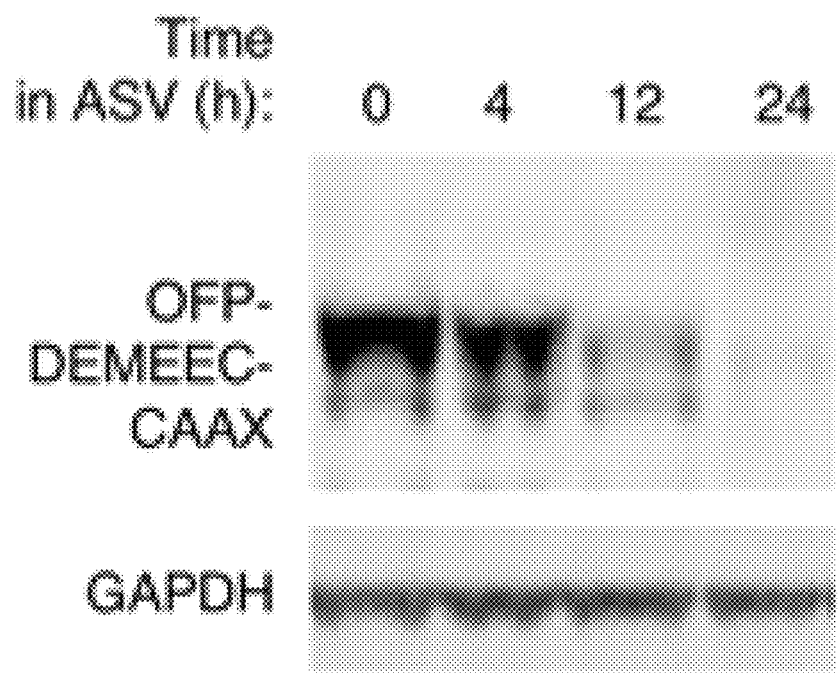
Figure 13D:
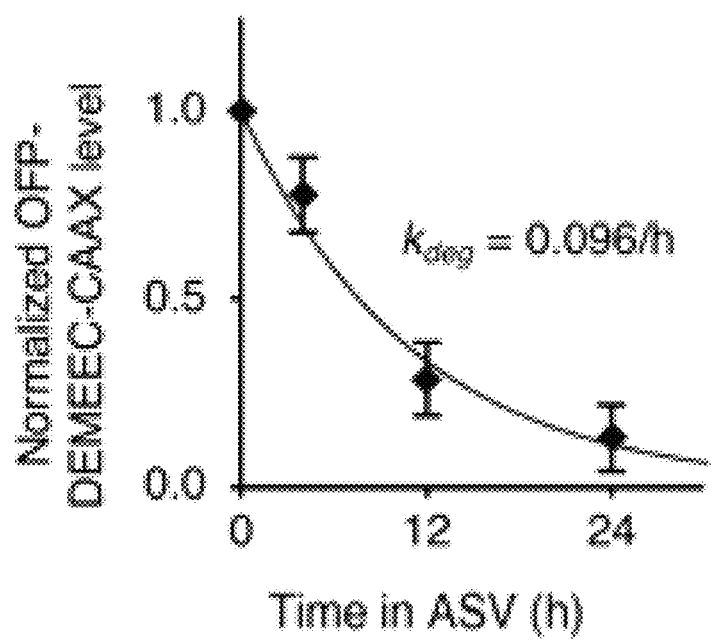

To calculate protein degradation and production rates, we used the SMASh tag (Chung et al. (2015) Nat. Chem. Biol. 11:713). This polypeptide tag contains a degron that is removed by cis-proteolysis by a linked NS3 protease. In the absence of a drug, NS3 protease activity causes the SMASh tag to be removed from proteins as they are produced, so the proteins are not degraded. Addition of a NS3 protease inhibitor, such as asunaprevir (ASV), blocks tag removal on subsequently synthesized proteins, causing effective shutoff of further protein production. The degradation of protein copies produced before drug application can then be followed over time immunoblotting (FIG. 13B-3D). The decay rates of all components were experimentally determined using this method (FIG. 13E).

Figure 13F:
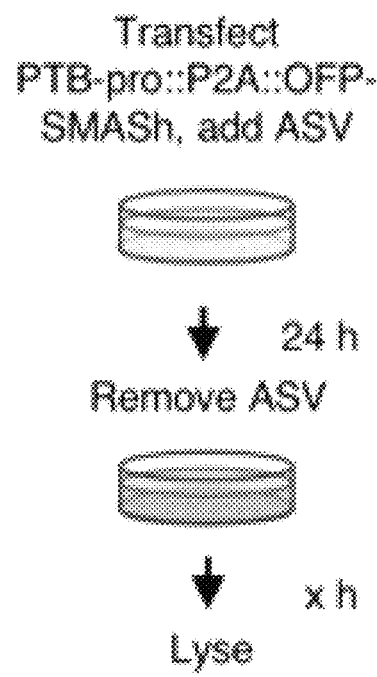
Figure 13G:
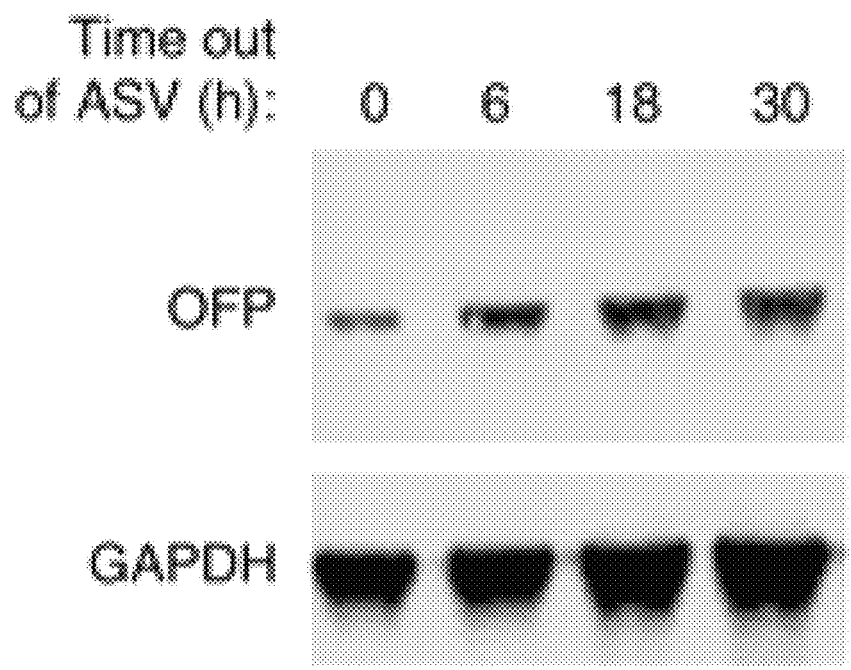
Figure 13H:
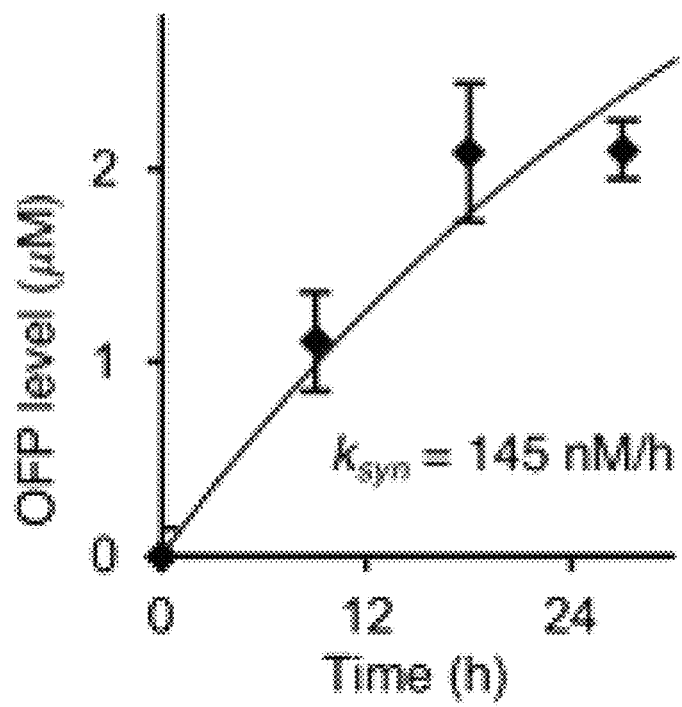
Figure 14B:
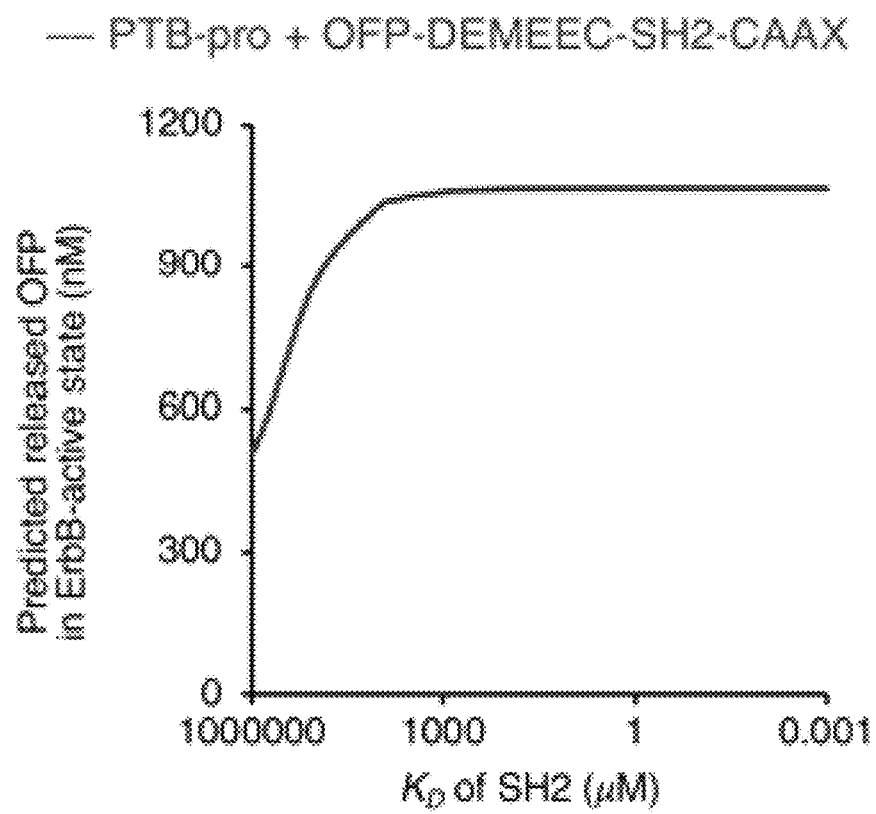

Translation kinetics were measured using a reverse SMASh technique, in which protein accumulation is first suppressed by ASV. ASV is then washed out and immunoblotting performed at various times afterwards. Measurements of band intensities relative to concentration standards allows quantitation of the amount of protein synthesized over time (FIGS. 13F to 13G).

Application of Mathematical Model

Figure 8A:
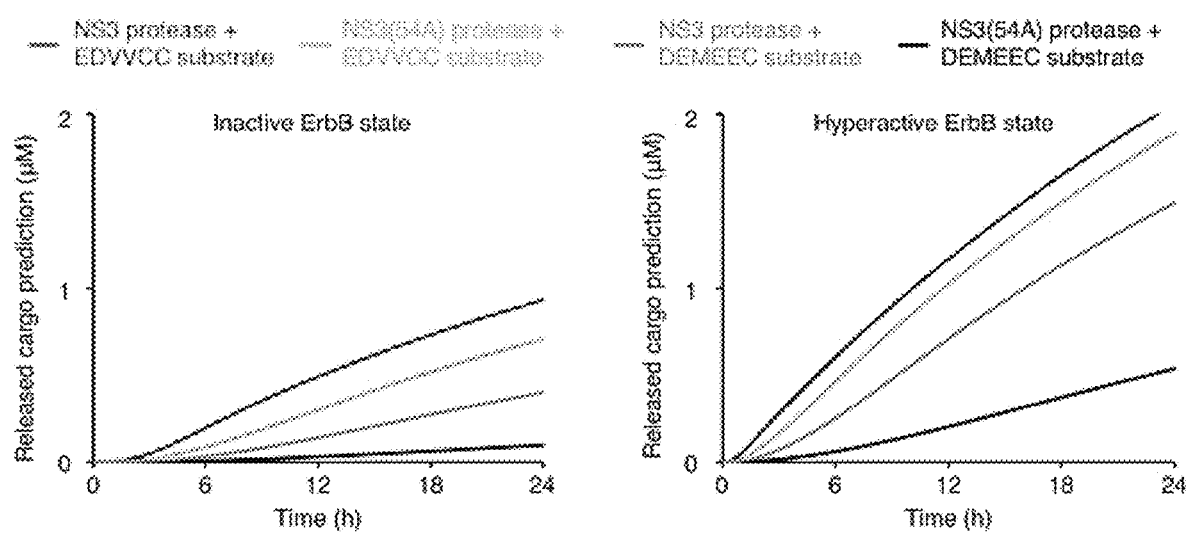
FIGS. 8A-8D show modeling of the molecular integrator of ErbB signaling.
Figure 8B:
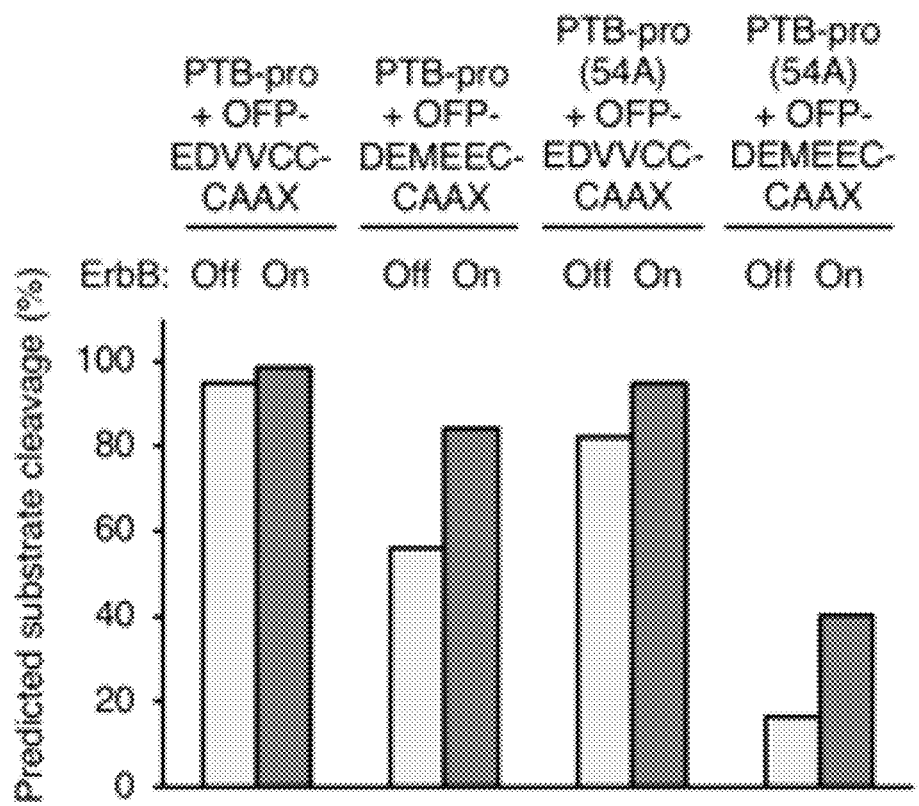

While we could obtain or estimate some parameters from published reports (FIGS. 12E and 12F), we calculated juxtamembrane volume from a molecular model (FIG. 1C), and measured component synthesis and degradation rates using our previously described Small Molecule-Assisted Shutoff (SMASh) tag (Chung et al. (2015) Nat. Chem. Biol. 11:713). SMASh tags shut off protein production upon drug addition and permit protein production when drug is removed, enabling measurement of protein decay or accumulation by immunoblotting (FIG. 13). We then used the Haldane-Briggs implementation of Michaelis-Menten kinetics to calculate substrate cleavage rates from concentrations of protease and substrate, accounting for concentration of protease at the membrane and basal cleavage by unbound protease. The model predicted that cargo release should be enhanced in BT-474 cells, which express constitutively active ErbB2 (FIG. 12F), compared to cells without ErbB2 activity. The degree of enhancement depended on protease speed (medium-cleaving NS3 or slow-cleaving NS3 with 54A mutation) and substrate affinity (high-affinity EDVVCC or medium-affinity DEMEEC), but in all cases was modest (FIGS. 8A and 8B).

Figure 8C:
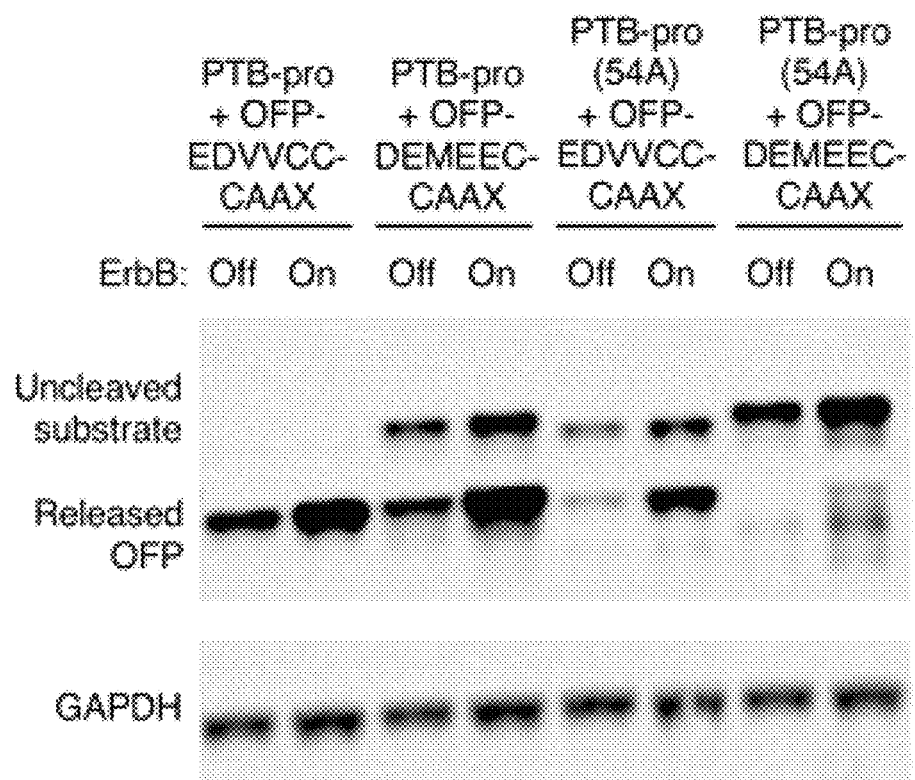
Figure 8D:
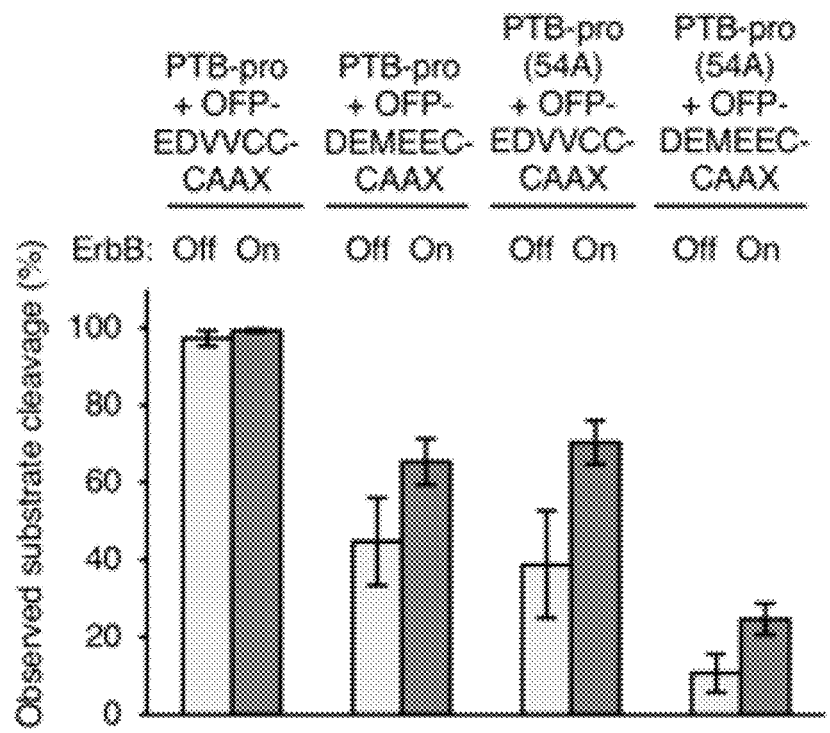

To test these predictions, we constructed and tested ErbB-RASER0.1. We tested both PTB-pro and PTB-pro(54A) protease components and OFP-EDVVCC-CAAX and OFP-DEMEEC-CAAX substrate components in BT-474 breast cancer cells that naturally overexpress ErbB2. Protease and substrate components were coexpressed from one transcriptional unit via a P2A ribosomal skipping sequence. For a matched ErbB-inactive control, we treated the same cells with the ErbB kinase inhibitor, lapatinib. By immunoblotting, we found that differences in product accumulation between ErbB-on and ErbB-off states closely matched those predicted by the model for PTB-pro (FIGS. 8C and 8D), suggesting the usefulness of the model. However, cleavage rates for PTB-pro(54A) were lower in the experiment than in the model. This discrepancy may be a due to inaccuracy of the inputted $K_M$ or $k_{cat}$ values for pro(54A), which is NS3 protease with a 54A mutation and without the NS4A cofactor. Those values were estimated by combining the known individual effects of 54A mutation and NS4A loss (Landro et al. (1997) Biochemistry 36:9340, Tong et al. (2006) Antiviral Res. 70:28), but they may be inaccurate if the effects of these changes are not additive.

By confirming the model prediction of high basal cleavage with medium-speed protease and high-affinity substrate, these results also allowed us to further rule out the use of TEV protease, which exhibits even faster cleavage of its substrate. These results also confirmed that effector release was only weakly dependent on ErbB hyperactivity in ErbB-RASER0.1, indicating that further enhancement of ErbB-dependent release was needed.

Example 5

Materials and Methods

DNA Constructs.

Plasmids encoding RASER cassettes were cloned by standard molecular biology techniques including PCR, restriction enzyme digestion and ligation or In-Fusion enzyme (Clontech). All subcloned fragments were sequenced in their entirety to confirm successful construction. Full sequences of all plasmids used in this study are available upon request.

Chemical Reagents.

ErbB tyrosine kinase inhibitors lapatinib (TSZ Chem), afatinib (TSZ Chem), and osimertinib (Selleckchem) were purchased from commercial sources. HCV NS3 inhibitor asunaprevir (ASV) was obtained by custom synthesis (Acme Bioscience). For each chemical, a 1-mM stock solution in dimethylsulfoxide (Thermo Fisher) was prepared and stored at −20° C. Stock solutions were diluted into cell culture media to achieve final treatment concentrations of 0.5 µM for lapatinib, 1 µM for afatinib, 0.1 µM for osimertinib, or 1 µM for ASV. For cancer cell treatment in FIG. 11, 10 µM of lapatinib was used.

Antibodies.

The following primary antibodies were used for immunoblotting at the indicated dilutions: mouse monoclonal anti-v5 (Thermo Scientific, R960-25), 1:2000; mouse monoclonal anti-GAPDH (Santa Cruz Biotechnology, clone G-9, sc-365062), 1:4000; rabbit polyclonal anti-GAPDH (Abcam, ab9485), 1:1000; mouse monoclonal anti-GAPDH (Pierce, clone GA1R, MA5-15738), 1:1000; rabbit monoclonal anti-phospho-EGFR/ErbB 1 Tyr1173 (Cell Signaling, clone 53A5, 4407S), 1:1000; rabbit monoclonal anti-phospho-HER2/ErbB2 Tyr1221/1222 (Cell Signaling, clone 6B 12, 2243S), 1:1000; rabbit monoclonal anti-cleaved PARP (Abcam, clone E51, ab32064), 1:1000; rabbit polyclonal anti-tdTomato (OriGene, TA150128), 1:2000; mouse monoclonal anti-p27 Kip1 (Cell Signaling, clone SX53G8.5, 3698T), 1:1000; rabbit monoclonal anti-Bim (Cell Signaling, clone C34C5, 2933T), 1:1000; rabbit polyclonal anti-phospho-Akt1/2/3-473 (Santa Cruz Biotechnology, sc-7985), 1:100; mouse monoclonal anti-phospho-ERK1/2 (Santa Cruz Biotechnology, clone E-4, sc-7383), 1:200. Secondary antibodies were LI-COR 680RD goat-anti-mouse, 680RD goat-anti-rabbit, 800CW goat-anti-mouse, and 800CW goat-anti-rabbit, used at 1:5000 dilution each.

Cell Culture and Transfection.

BT-474 (ATCC), SK-BR-3 (ATCC), 4T-1 (gift from Dr. Ronald Levy at Stanford University) cell lines were cultured at 37° C. in 5% C02 in RPMI 1640 medium (Life Technoloiges) supplemented with 10% FBS (Gibco), and 100 U/mL penicillin and 100 µg/mL streptomycin (Life Technologies). MCF-7 (gift from Dr. Howard Chang at Stanford University), SK-OV-3 (gift from Dr. Hongjie Dai at Stanford University), and LN-229 EGFRvIII (gift from Xiaokun Shu at UCSF) cell lines were cultured at 37° C. in 5% $CO_2$ in Dulbecco's Modified Eagle's Medium (DMEM, HyClone) supplemented with 10% FBS (Gibco) and 100 U/mL penicillin and 100 µg/mL streptomycin (Life Technologies). Cells were transfected using Lipofectamine 3000 (Life Technologies) in Opti-MEM (Life Technologies) according to the manufacturer's recommended protocol.

Microscopy.

Fluorescence imaging was performed on a Zeiss Axiovert 200M with a 10×/0.25-numerical aperture (NA) objective. Cells were cultured in 12-well plates (Greiner) and imaged in culture media. The microscope was connected to Hamamatsu ORCA-ER cameras and controlled by Micro-Manager software. Image processing was performed in ImageJ.

Immunoblotting.

After washing twice with PBS, cells were lysed with 50-100 µl of hot SDS lysis buffer (100 mM Tris HCl pH 8.0, 4% SDS, 20% glycerol, 0.2% bromo-phenol blue, 10% 2-mercaptoethanol) and DNA was sheared by sonication. After heating to 80-90° C. for several minutes, cell lysates were loaded onto 4%-12% Bis-Tris gels (NuPAGE, Life Technologies) along with Novex Sharp pre-stained protein standard (Life Technologies) or Precision Plus Protein Dual Color Standards (Bio-Rad). Gels were transferred to nitrocellulose membranes using Trans-Blot Turbo Transfer System (Bio-Rad). Membranes were probed with primary and secondary antibodies, and imaged using LI-COR Odyssey imaging system. Quantification of immunoblots was performed in ImageJ.

Generation of the Molecular Integrator Structural Model.

Using UCSF Chimera (Pettersen et al. (2004) *J. Comput. Chem.* 25:1605), a 3D model was constructed comprising a ErbB1 cytosolic segment (PDB entry 2GS2), the SHC PTB domain interacting with pTyr-1173 (PDB entry 1SHC), NS3 (PDB entry 3M50), the Crk SH2 domain interacting with pTyr-1016 (1JU5), mKO2 (PDB entry 2H5Q), and a modelled phospholipid bilayer interacting with the ErbB1 kinase domain (Arkhipov et al. (2013) *Cell* 152:557). First, the C-terminal flexible region of ErbB1 was loop-modeled and docked with the SH2 and PTB domains, and energy minimization was performed. Docking sites were adapted from Hsieh et al. (BMC Syst Biol (2010) 4:57). Finally, a published model of the complex of ErbB1 and the phospholipid bilayer (Arkhipov et al. (2013) Cell 152:557) was imposed onto the 2GS2-1JU5-1SHC model.

Calculating Synthesis and Degradation Rates of RASER Components Using the SMASh Technique.

To measure the half-lives of the SMASh-tagged RASER components, we assumed that the protein production rate is constant at the time ASV is added to induce destruction of newly synthesized protein copies (24-28 h post-transfection). The decay of previously synthesized protein copies from the time of ASV addition can be modeled with the differential equations where P(t) is protein concentration of SMASh-tagged protein at time t and $k_{deg}$ is decay rate constants of the SMASh-tagged protein:

$$dP(t)/dt = -k_{deg} \cdot P(t),$$

with P(0) set to the protein amount at time zero. Integration yields:

$$P(t) = P(0) \cdot e^{-k_{deg} \cdot t}.$$

We measured half-lives ($t_{1/2}$) of the RASER components by fitting the protein band intensities of different time points to the above mono-exponential decay curve (n=3). We then determined the decay rate constant ($k_{deg}$).

To determine $k_{syn}$, the protein production rate constant, the rate of changes in the protein concentrations were modeled with the following differential equation:

$$dP(t)/dt = k_{syn} - k_{deg} \cdot P(t),$$

with P(0)=0. Integration yields:

$$P(t) = (k_{syn}/k_{deg}) \cdot (1 - e^{k_{deg} \cdot t})$$

We assumed that the production rates of all RASER components are the same in the absence of lapatinib. This is because the RASER system was constructed in the bicistronic vector with a P2A ribosomal skipping sequence, which allows production of upstream and downstream proteins at approximately the same level (55). The translation rate of OFP-V5 was measured by the following process. PTBHIF-Pro::P2A::OFP-V5-SMASh was transiently transfected in the presence of ASV to block protein accumulation. After 24 h, ASV was washed out to initiate protein accumulation, and then cells were lysed for immunoblotting at various times afterwards. Amounts of detected OFP-V5 were obtained by interpolating anti-V5 band intensities to those of known amounts of purified OFP-V5. Volumes of cell lysates loaded was estimated by interpolating anti-GAPDH band intensities to those from known volumes of cell lysate, then these were multiplied by the estimated transfection efficiency to obtain the volumes of transfected cell lysates loaded. The calculated concentrations of OFP-V5 over time were fitted to the above equation with $k_{deg, mKO2-V5}$ previously measured as 0.026/h. $k_{syn}$ was then calculated as 145 nM/h. All curve fits were performed in MATLAB_R2015b. The $k_{syn}$ and $k_{deg}$ values of each RASER components are listed in FIG. 13E.

Imaging of Cargo Release and Transcriptional Reporter Expression.

Cells were cultured in 12-well plastic-bottom plates or 96-well glass-bottom plates (Greiner) and imaged in culture media using an Axiovert 200M inverted epifluorescence microscope (Zeiss) with a 10×0.5-NA or a 20×0.57-NA air objective and a Texas Red filter set connected to an ORCA-ER camera (Hamamatsu) and controlled by Micro-Manager software as previously described (Pimenta et al. (2016) *N. Engl. J. Med.* 374:2602). Image intensities were scaled to the same range for each channel within an experiment using ImageJ.

Virus Preparation and Infection.

To package lentivirus, HEK293T cells at ~70% confluency were transfected with psPAX2, pMD2.G, and pLL3.7 plasmids using Lipofectamine 2000 (Life Technologies).

Two days following transfection, viral supernatant was filtered with a 0.45 µm PES filter before using to infect target cells. rAAVdj-CAG-RASER1C-mCardinal-BID and rAAVdj-mCardinal were produced at the Stanford Gene Vector and Virus Core (Stanford University). Virus infected cells were neither sorted nor purified prior to obtaining the results shown, to remain close to the actual use scenario.

Caspase-3 Activity Assay.

NucView 488 Caspase-3 substrate (Biotium) and Hoechst 33342 (Invitrogen) were diluted into culture media to final concentrations of 1 µM each. After 1 h of incubation, cells were imaged with the Axiovert 200M with a 10×0.5-NA air objective.

Cell Viability Assay

The cytotoxicity of 5 µM staurosporine (Apex Bio, as a positive control for apoptosis), 10 µM carboplatin (Santa Cruz Biotechnology)+10 µM paclitaxel (Apex Bio), 10 µM lapatinib (TSZ Chem), ErbB-RASER1C-OFP-BID lentivirus (MOI 2), or control mKO2 lentivirus (MOI 2) were tested in BT-474, H1975, MCF-7, MCF-10A and MRC-5 cells. For each condition, relative viability was assessed using the fluorogenic live cell marker Gly-Phe-AFC (Cell-Titer-Fluor Cell Viability Assay kit, Promega) and an Infinite M1000 spectrofluorimeter (TECAN) according to the manufacturer's protocol. A cytotoxicity index was calculated by subtracting the Gly-Phe-AFC signal of each condition from that of the mKO2-only lentivirus condition, followed by normalization to the value for staurosporine.

RASER Testing in a Model of Disseminated Cancer.

GFP-expressing Huh7.5 cells were cultured in 1% DMSO+10% FBS+RPMI to differentiate into a non-proliferating mature hepatocyte phenotype that can be maintained for weeks in monolayer. At day 4 of differentiation, 20,000 of ErbB+ pancreatic cancer cell line (BxPC3) or ErbB− breast tumor cell line (MCF-7) were co-cultured. Both cancer cell lines were marked with CellTracker Orange CMTMR (Invitrogen). After 24 h of co-culture, either rAAV-RASER1C-BID or control rAAV were treated for a designated time with specified MOI. Viable cells were counted and expressed as a fraction of the number of cells in the negative control of the first experiment (MOI 0 condition for FIG. 18 and control rAAV infection for FIG. 11). The cytotoxic fraction was then calculated as 1 minus the viable fraction.

Guide RNA Sequences

The spacer (variable) sequences of guide RNAs tested for activation of the CSF2 (GM-CSF) promoter were:

```
gRNA 1:     GTGACCACAAAATGCCAGGG,        (SEQ ID NO: 7)

gRNA 2:     CGGGGGAACTACCTGAACTG,        (SEQ ID NO: 8)

gRNA 3:     GGCCCTTATCAGCCACACAT,        (SEQ ID NO: 9)

gRNA 4:     CGGTGAGCCTTTTCCCTAGG,        (SEQ ID NO: 10)

gRNA 5:     TTATCAGCCACACATGGGAA,        (SEQ ID NO: 11)

gRNA 6:     GCCAGGAGATTCCACAGTTC,        (SEQ ID NO: 12)

gRNA 7:     TGGGCTGTCGGTTCTTGGAA,        (SEQ ID NO: 13)

gRNA 8:     CCACCCACCCGCCTTCCTGA,        (SEQ ID NO: 14)

gRNA 9:     TGGAGAGCCCTCAGGAAGGC,        (SEQ ID NO: 15)
and gRNA 10:    GGCTGCCCCCTCCCTCTGAG.        (SEQ ID NO: 16)
```

The gRNAs 1-3 were from Doench et al. (Nat Biotechnol (2016) 34:184). The gRNAs 4-6 were from Konermann et al. (Nature (2015) 517:583). gRNAs 7-10 were from Horlbeck et al. (Elife (2016) 5).

Statistical Analyses.

Statistical analyses were performed using the Prism7 program (GraphPad). Given preliminary measurements of effect size and variability, we determined a sample size of 3 biological replicates would provide sufficient power to achieve an alpha level of 0.05. To test for significant differences between ErbB states or cell types for a given RASER variant, data distributions were first assessed for normality using the Anderson-Darling test. In all cases, data distributions fit a normal distribution except for the mCherry brightness measurements of FIGS. 7F and 16C. To assess the significance of differences in RASER output between EGF stimulation conditions in MCF-7 cells (FIG. 9B), one-way analysis of variance (ANOVA). To assess the significance of increased RASER output in an ErbB-on condition above the baseline (ErbB-off) condition in the same cell type (FIGS. 7F, 4B, and 16C), one-tailed unpaired t tests were performed. To detect any differences in endogenous Akt and Erk activation in RASER-expressing and RASER-nonexpressing conditions in the same cell type (FIG. 4C), two-tailed unpaired t tests were performed. To assess the significance of increased RASER output in ErbB-hyperactive cancer cells over an ErbB-normal control cell (FIGS. 7I, 10C, and 10F), one-tailed unpaired t tests were performed, with Bonferroni correction of p-values for multiple comparisons where appropriate (FIG. 10F). For FIGS. 10, 11, and 18, single-factor ANOVA followed by Holm-Sidak's multiple comparisons test was performed. To assess the significance of differences in mCherry expression in combinations of ErbB activity and RASER or dCas9VP64 expression (FIGS. 5C and 16C), differences between multiple conditions were assessed using the non-parametric Kruskal-Wallis test followed by a Dunn's posthoc test for pairwise comparisons.

Apoptosis Assay.

After washing twice with PBS, cells were lysed with 50-100 µl of hot SDS lysis buffer (100 mM Tris HCl pH 8.0, 4% SDS, 20% glycerol, 0.2% bromo-phenol blue, 10% 2-mercaptoethanol) and DNA was sheared by sonication. After heating to 80-90° C. for several minutes, cell lysates were loaded onto 4%-12% Bis-Tris gels (NuPAGE, Life Technologies) along with Novex Sharp pre-stained protein standard (Life Technologies) or Precision Plus Protein Dual Color Standards (Bio-Rad). Gels were transferred to nitrocellulose membranes using Trans-Blot Turbo Transfer System (Bio-Rad). Membranes were probed with primary and secondary antibodies, and imaged using LI-COR Odyssey imaging system. Quantification of immunoblots was performed in ImageJ.

While the preferred embodiments of the invention have been illustrated and described, it will be appreciated that various changes can be made therein without departing from the spirit and scope of the invention.

What is claimed is:

1. A vector system comprising one or more viral vectors comprising:
   a) a first expression cassette encoding a first fusion protein comprising a protease connected to a phosphotyrosine binding (PTB) domain capable of binding to a first constitutively phosphorylated tyrosine residue on an endogenous hyperactive receptor tyrosine kinase; and
   b) a second expression cassette encoding a second fusion protein comprising a sequence selected from the group consisting of SEQ ID NO:18, SEQ ID NO:19, SEQ ID NO:21, and SEQ ID NO:22, or a sequence having at least 90% identity to a sequence selected from the group consisting of SEQ ID NO:18, SEQ ID NO:19, SEQ ID NO:21, and SEQ ID NO:22.

2. The vector system of claim 1, wherein the one or more viral vectors comprise a bicistronic vector comprising the first expression cassette and the second expression cassette.

3. The vector system of claim 2, wherein the bicistronic vector comprises a viral T2A peptide or an internal ribosome entry site (IRES).

4. The vector system of claim 1, wherein said one or more viral vectors are selected from the group consisting of a lentivirus vector and an adeno-associated virus vector.

5. The vector system of claim 1, wherein the one or more viral vectors are non-integrating viral vectors.

6. The vector system of claim 1, wherein the protease is the hepatitis C virus (HCV) NS3 protease.

7. The vector system of claim 1, wherein the first fusion protein further comprises a degron, wherein degradation activity of the degron is inhibited by the binding of the PTB domain of the first fusion protein to the first constitutively phosphorylated tyrosine residue on the endogenous hyperactive receptor tyrosine kinase such that the first fusion protein accumulates preferentially in cancerous cells.

8. The vector system of claim 7, wherein the degron is located in a loop of the PTB domain.

9. The vector system of claim 7, wherein the degron is a HIF1a degron.

10. The vector system of claim 9, wherein the first fusion protein comprises the amino acid sequence of SEQ ID NO:17, or a sequence having at least 90% identity to the sequence of SEQ ID NO:17.

11. The vector system of claim 1, wherein the PTB is Shc PTB.

12. A vector system comprising a viral vector comprising a sequence selected from the group consisting of SEQ ID NO:23 and SEQ ID NO:24, or a sequence having at least 90% identity to the sequence selected from the group consisting of SEQ ID NO:23 and SEQ ID NO:24.

13. The vector system of claim 1, further comprising a third expression cassette encoding a viral capsid protein capable of assembly into a viral-like particle.

14. A composition comprising the vector system of claim 1 and a pharmaceutically acceptable excipient.

15. A virus-like particle comprising the vector system of claim 1 and a viral capsid protein.

16. The virus-like particle of claim 15, further comprising a viral envelope protein.

17. A composition comprising the virus-like particle of claim 15.

18. The composition of claim 17, further comprising a pharmaceutically acceptable excipient.

19. A method for producing viral-like particles (VLPs), the method comprising:
   a) transforming a host cell with the vector system of claim 13; and
   b) culturing the transformed host cell under conditions whereby capsid proteins are expressed and assembled into VLPs encapsulating the vector system.

20. A method for targeted treatment of a cancer associated with hyperactivity of a receptor tyrosine kinase, the method comprising administering to a subject in need thereof a therapeutically effective amount of the composition of claim 14.

21. The method of claim 20, wherein the hyperactive receptor tyrosine kinase is a hyperactive ErbB receptor tyrosine kinase.

22. The method of claim 20, wherein the cancer is selected from the group consisting of breast cancer, ovarian cancer, lung cancer, glioma, colorectal cancer, head and neck cancer, and brain cancer.

23. A method for targeted treatment of a cancer associated with hyperactivity of a receptor tyrosine kinase, the method comprising administering to a subject in need thereof a therapeutically effective amount of the composition of claim 18.

24. The method of claim 23, wherein the hyperactive receptor tyrosine kinase is a hyperactive ErbB receptor tyrosine kinase.

25. The method of claim 23, wherein the cancer is selected from the group consisting of breast cancer, ovarian cancer, lung cancer, glioma, colorectal cancer, head and neck cancer, and brain cancer.

26. A kit comprising the vector system of claim 1 and instructions for treating cancer.

27. A composition comprising the vector system of claim 12 and a pharmaceutically acceptable excipient.

28. A virus-like particle comprising the vector system of claim 12 and a viral capsid protein.

29. The virus-like particle of claim 28, further comprising a viral envelope protein.

30. A composition comprising the virus-like particle of claim 28.

31. The composition of claim 30, further comprising a pharmaceutically acceptable excipient.

32. A method for producing viral-like particles (VLPs), the method comprising:
   a) transforming a host cell with the vector system of claim 12; and
   b) culturing the transformed host cell under conditions whereby capsid proteins are expressed and assembled into VLPs encapsulating the vector system.

33. A method for targeted treatment of a cancer associated with hyperactivity of a receptor tyrosine kinase, the method comprising administering to a subject in need thereof a therapeutically effective amount of the composition of claim 27.

34. The method of claim 33, wherein the cancer is selected from the group consisting of breast cancer, ovarian cancer, lung cancer, glioma, colorectal cancer, head and neck cancer, and brain cancer.

35. A method for targeted treatment of a cancer associated with hyperactivity of a receptor tyrosine kinase, the method comprising administering to a subject in need thereof a therapeutically effective amount of the composition of claim 31.

36. The method of claim 35, wherein the cancer is selected from the group consisting of breast cancer, ovarian cancer, lung cancer, glioma, colorectal cancer, head and neck cancer, and brain cancer.

* * * * *